(12) United States Patent
Kubota et al.

(10) Patent No.: US 12,239,005 B2
(45) Date of Patent: Feb. 25, 2025

(54) DISPLAY DEVICE AND SYSTEM

(71) Applicant: Semiconductor Energy Laboratory Co., Ltd., Kanagawa-ken (JP)

(72) Inventors: Daisuke Kubota, Kanagawa (JP); Ryo Hatsumi, Kanagawa (JP); Taisuke Kamada, Saitama (JP); Yuji Iwaki, Kanagawa (JP); Junpei Momo, Kanagawa (JP); Shunpei Yamazaki, Tokyo (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 18/417,153

(22) Filed: Jan. 19, 2024

(65) Prior Publication Data

US 2024/0164196 A1  May 16, 2024

Related U.S. Application Data

(63) Continuation of application No. 17/299,403, filed as application No. PCT/IB2020/053037 on Mar. 31, 2020, now Pat. No. 11,882,755.

(30) Foreign Application Priority Data

Apr. 12, 2019 (JP) .................................. 2019-076318

(51) Int. Cl.
*H10K 65/00* (2023.01)
*A61B 5/00* (2006.01)
(Continued)

(52) U.S. Cl.
CPC ............ *H10K 65/00* (2023.02); *A61B 5/1172* (2013.01); *A61B 5/14532* (2013.01);
(Continued)

(58) Field of Classification Search
CPC ........ H10K 65/00; H10K 30/80; H10K 59/40; H10K 59/65; H10K 30/30; A61B 5/1172;
(Continued)

(56) References Cited

U.S. PATENT DOCUMENTS 8,860,696 B2  10/2014  Wassvik et al.
9,088,006 B2  7/2015  Yamazaki et al.
(Continued)

FOREIGN PATENT DOCUMENTS

CN  001853159 A  10/2006
CN  101211246 A  7/2008
(Continued)

OTHER PUBLICATIONS

International Search Report (Application No. PCT/IB2020/053037) Dated Jun. 23, 2020.

(Continued)

*Primary Examiner* — Abhishek Sarma
(74) *Attorney, Agent, or Firm* — Husch Blackwell LLP

(57) ABSTRACT

A display device having a photosensing function is provided. A display device having a biometric authentication function typified by fingerprint authentication is provided. A display device having a touch panel function and a biometric authentication function is provided. The display device includes a first substrate, a light guide plate, a first light-emitting element, a second light-emitting element, and a light-receiving element. The first substrate and the light guide plate are provided to face each other. The first light-emitting element and the light-receiving element are provided between the first substrate and the light guide plate. The first light-emitting element has a function of emitting first light through the light guide plate. The second light-emitting element has a function of emitting second light to a side surface of the light guide plate. The light-receiving element (Continued)

element has functions of receiving the first light and converting the first light into an electric signal and functions of receiving the second light and converting the second light into an electric signal. The first light includes visible light, and the second light includes infrared light.

17 Claims, 22 Drawing Sheets

(51) Int. Cl.
    *A61B 5/1172*    (2016.01)
    *A61B 5/145*     (2006.01)
    *A61B 5/1455*    (2006.01)
    *G06F 3/044*     (2006.01)
    *G06V 40/12*     (2022.01)
    *G06V 40/13*     (2022.01)
    *G09F 9/33*      (2006.01)
    *H01L 25/18*     (2023.01)
    *H10K 30/80*     (2023.01)
    *H10K 59/40*     (2023.01)

(52) U.S. Cl.
    CPC ........ *A61B 5/14552* (2013.01); *A61B 5/4872* (2013.01); *G06F 3/0443* (2019.05); *G06V 40/1318* (2022.01); *G06V 40/1365* (2022.01); *H01L 25/18* (2013.01); *H10K 30/80* (2023.02); *H10K 59/40* (2023.02); *G09F 9/33* (2013.01)

(58) Field of Classification Search
    CPC ............ A61B 5/14532; A61B 5/14552; A61B 5/4872; A61B 5/6898; A61B 5/1455; A61B 5/1171; A61B 5/14551; G06F 3/0443; G06F 3/0412; G06F 3/044; G06F 3/01; G06F 21/32; G06V 40/1318; G06V 40/1365; H01L 25/18; G09F 9/33; G09F 9/30; Y02E 10/549; G06T 1/00; G06T 7/00
    See application file for complete search history.

(56) References Cited

U.S. PATENT DOCUMENTS

| | | | |
|---|---|---|---|
| 9,155,498 | B2 | 10/2015 | Akiyama |
| 9,167,994 | B2 | 10/2015 | Akiyama |
| 9,368,541 | B2 | 6/2016 | Kurokawa. et al. |
| 9,489,088 | B2 | 11/2016 | Kurokawa. et al. |
| 9,627,648 | B2 | 4/2017 | Yamazaki et al. |
| 9,639,211 | B2 | 5/2017 | Kurokawa. et al. |
| 9,766,763 | B2 | 9/2017 | Jinbo. et al. |
| 10,003,047 | B2 | 6/2018 | Yamazaki et al. |
| 10,228,807 | B2 | 3/2019 | Jinbo. et al. |
| 10,381,599 | B2 | 8/2019 | Yamazaki et al. |
| 10,903,453 | B2 | 1/2021 | Yamazaki et al. |
| 2007/0084989 | A1 | 4/2007 | Lange et al. |
| 2008/0150848 | A1 | 6/2008 | Chung et al. |
| 2011/0216042 | A1 | 9/2011 | Wassvik et al. |
| 2012/0044444 | A1 | 2/2012 | Park et al. |
| 2015/0035803 | A1 | 2/2015 | Wassvik et al. |
| 2016/0361031 | A1 | 12/2016 | Kim. et al. |
| 2017/0046002 | A1 | 2/2017 | Kurokawa. et al. |
| 2018/0314379 | A1 | 11/2018 | Shen |
| 2019/0090818 | A1 | 3/2019 | Nakajima et al. |
| 2019/0110700 | A1 | 4/2019 | Nakajima et al. |
| 2019/0117084 | A1 | 4/2019 | Nakajima et al. |
| 2019/0117095 | A1 | 4/2019 | Nakajima et al. |
| 2019/0125252 | A1 | 5/2019 | Nakajima et al. |
| 2019/0150755 | A1 | 5/2019 | Nakajima et al. |
| 2019/0159682 | A1 | 5/2019 | Nakajima et al. |
| 2019/0159685 | A1 | 5/2019 | Nakajima et al. |
| 2019/0159722 | A1 | 5/2019 | Nakajima et al. |
| 2019/0159723 | A1 | 5/2019 | Nakajima et al. |
| 2019/0175027 | A1 | 6/2019 | Nakajima et al. |
| 2020/0395576 | A1 | 12/2020 | Yamazaki. et al. |
| 2021/0327979 | A1 | 10/2021 | Kamada et al. |

FOREIGN PATENT DOCUMENTS

| | | |
|---|---|---|
| CN | 102209949 A | 10/2011 |
| CN | 102376723 A | 3/2012 |
| CN | 110537186 A | 12/2019 |
| EP | 1668483 A | 6/2006 |
| EP | 2356551 A | 8/2011 |
| EP | 3427648 A | 1/2019 |
| EP | 3427649 A | 1/2019 |
| EP | 3427650 A | 1/2019 |
| EP | 3427651 A | 1/2019 |
| EP | 3427652 A | 1/2019 |
| EP | 3427653 A | 1/2019 |
| EP | 3427654 A | 1/2019 |
| EP | 3427655 A | 1/2019 |
| EP | 3427656 A | 1/2019 |
| EP | 3430989 A | 1/2019 |
| EP | 3440995 A | 2/2019 |
| JP | 2007-506178 | 3/2007 |
| JP | 2009-086565 A | 4/2009 |
| JP | 2010-020237 A | 1/2010 |
| JP | 2012-044143 A | 3/2012 |
| JP | 2012-508913 | 4/2012 |
| JP | 2013-033275 A | 2/2013 |
| JP | 2013-073965 A | 4/2013 |
| JP | 2013-257609 A | 12/2013 |
| JP | 2014-197522 A | 10/2014 |
| JP | 2014-238616 A | 12/2014 |
| JP | 2016-127018 A | 7/2016 |
| JP | 2017-189489 A | 10/2017 |
| JP | 2019-020687 A | 2/2019 |
| KR | 2006-0083420 A | 7/2006 |
| KR | 2008-0060127 A | 7/2008 |
| KR | 2011-0096041 A | 8/2011 |
| KR | 2012-0017943 A | 2/2012 |
| TW | 200513725 | 4/2005 |
| WO | WO-2005/029394 | 3/2005 |
| WO | WO-2010/056177 | 5/2010 |
| WO | WO-2011/055638 | 5/2011 |
| WO | WO-2013/047445 | 4/2013 |
| WO | WO-2017/179695 | 10/2017 |
| WO | WO-2018/203955 | 11/2018 |
| WO | WO-2020/053692 | 3/2020 |

OTHER PUBLICATIONS

Written Opinion (Application No. PCT/IB2020/053037) Dated Jun. 23, 2020.

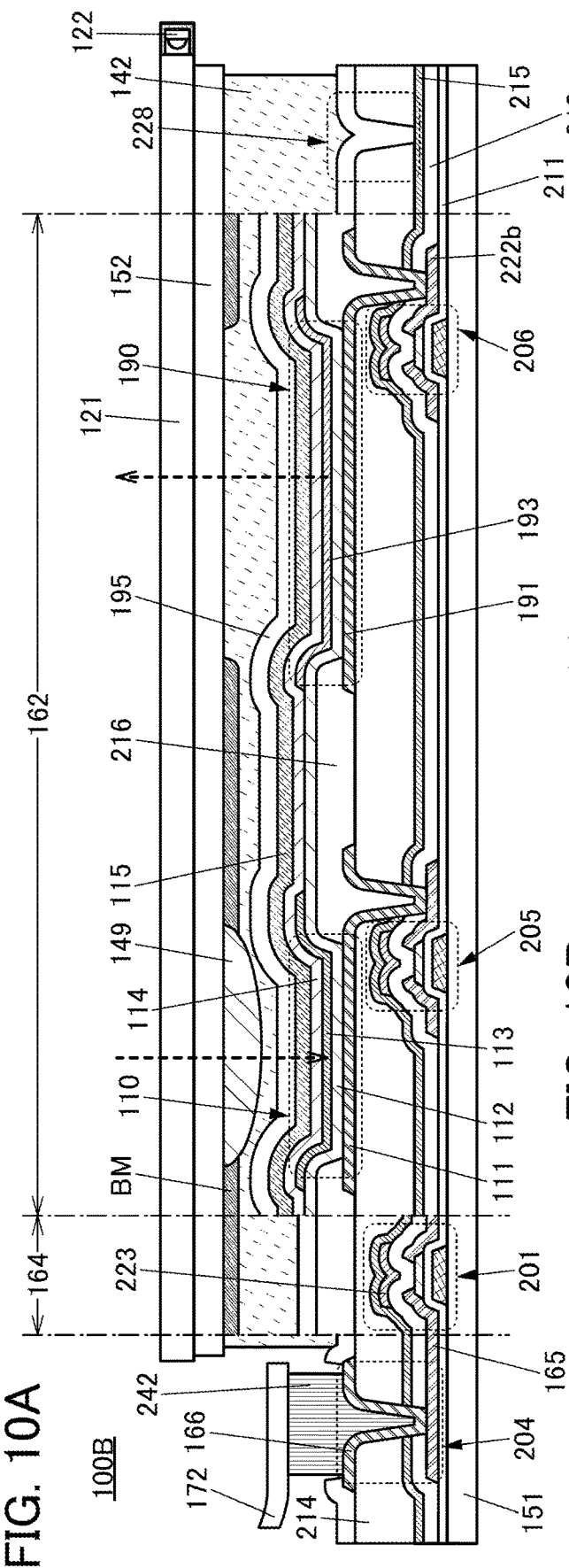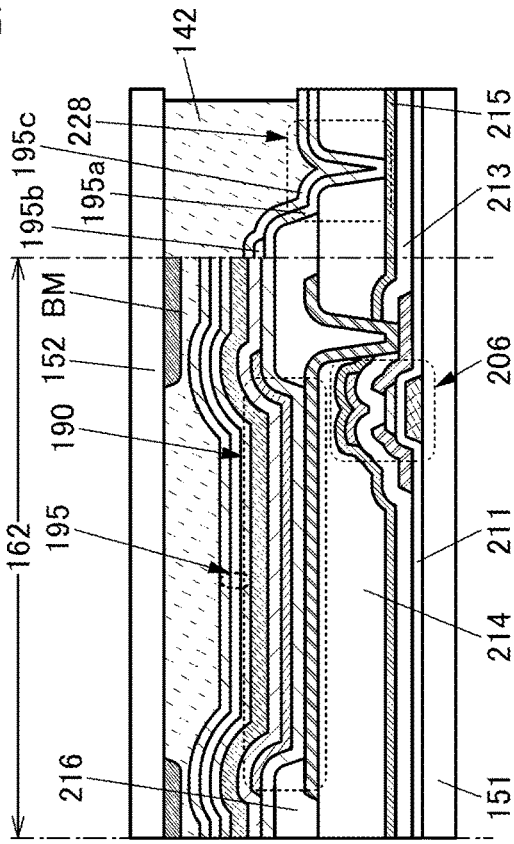
FIG. 10A
FIG. 10B

DISPLAY DEVICE AND SYSTEM

This application is a continuation of copending U.S. application Ser. No. 17/299,403, filed on Jun. 3, 2021 which is 371 of international application PCT/M2020/053037 filed on Mar. 31, 2020 which are all incorporated herein by reference.

TECHNICAL FIELD

One embodiment of the present invention relates to a display device. One embodiment of the present invention relates to a display device including a light-emitting element and a light-receiving element. One embodiment of the present invention relates to a display device having an authentication function. One embodiment of the present invention relates to a touch panel. One embodiment of the present invention relates to a system including a display device.

Note that one embodiment of the present invention is not limited to the above technical field. Examples of the technical field of one embodiment of the present invention disclosed in this specification and the like include a semiconductor device, a display device, a light-emitting device, a power storage device, a memory device, an electronic device, a lighting device, an input device (e.g., a touch sensor), an input/output device (e.g., a touch panel), a driving method thereof, and a manufacturing method thereof. A semiconductor device generally means a device that can function by utilizing semiconductor characteristics.

BACKGROUND ART

In recent years, application of display devices to a variety of uses has been expected. Examples of uses for a large display device include a television device for home use (also referred to as a TV or a television receiver), digital signage, and a PID (Public Information Display). In addition, a smartphone and a tablet terminal including a touch panel are being developed as portable information terminals.

Light-emitting devices including light-emitting elements have been developed, for example, as display devices. Light-emitting elements (also referred to as EL elements) utilizing an electroluminescence (hereinafter, referred to as EL) phenomenon have features such as ease of reduction in thickness and weight, high-speed response to an input signal, and driving with a direct-current low voltage source, and have been used in display devices. For example, Patent Document 1 discloses a flexible light-emitting device including an organic EL element.

REFERENCE

Patent Document

[Patent Document 1] Japanese Published Patent Application No. 2014-197522

SUMMARY OF THE INVENTION

Problems to be Solved by the Invention

An object of one embodiment of the present invention is to provide a display device having a photosensing function. Another object is to provide a display device having a biometric authentication function typified by fingerprint authentication. Another object is to provide a display device having both a touch panel function and a biometric authentication function. Another object is to provide a highly convenient display device. Another object is to provide a multifunctional display device. Another object is to provide a display device having a novel structure.

Another object of one embodiment of the present invention is to provide a display device having a function of obtaining user's health conditions. Another object is to provide a display device that can manage user's health.

Note that the description of these objects does not preclude the existence of other objects. One embodiment of the present invention does not have to achieve all of these objects. Objects other than these can be derived from the description of the specification, the drawings, the claims, and the like.

Means for Solving the Problems

One embodiment of the present invention is a display device including a first substrate, a light guide plate, a first light-emitting element, a second light-emitting element, and a light-receiving element. The first substrate and the light guide plate are provided to face each other. The first light-emitting element and the light-receiving element are provided between the first substrate and the light guide plate. The first light-emitting element has a function of emitting first light through the light guide plate. The second light-emitting element has a function of emitting second light to a side surface of the light guide plate. The light-receiving element has functions of receiving the first light and converting the first light into an electric signal and functions of receiving the second light and converting the second light into an electric signal. The first light includes visible light, and the second light includes infrared light.

Another embodiment of the present invention is a display device including a first substrate, a second substrate, a light guide plate, a first light-emitting element, a second light-emitting element, and a light-receiving element. The first substrate and the light guide plate are provided to face each other with the second substrate therebetween. The first light-emitting element and the light-receiving element are provided between the first substrate and the second substrate. The first light-emitting element has a function of emitting first light through the light guide plate. The second light-emitting element has a function of emitting second light to a side surface of the light guide plate. The light-receiving element has functions of receiving the first light and converting the first light into an electric signal and functions of receiving the second light and converting the second light into an electric signal. The first light includes visible light, and the second light includes infrared light. The second substrate has a lower refractive index with respect to light in a wavelength range from 800 nm to 1000 nm than the light guide plate.

Another embodiment of the present invention is a display device including a first substrate, a resin layer, a light guide plate, a first light-emitting element, a second light-emitting element, and a light-receiving element. The first substrate and the light guide plate are provided to face each other with the resin layer therebetween. The first light-emitting element and the light-receiving element are provided between the first substrate and the resin layer. The first light-emitting element has a function of emitting first light through the light guide plate. The second light-emitting element has a function of emitting second light to a side surface of the light guide plate. The light-receiving element has functions of receiving the first light and converting the first light into an electric signal and functions of receiving the second light and converting the second light into an electric signal. The first light includes visible light, and the second light includes infrared light. The resin layer is provided in contact with the light guide plate, has a function of attaching the first substrate to the light guide plate, and has a lower refractive index with respect to light in a wavelength range from 800 nm to 1000 nm than the light guide plate.

In the above, a conductive layer transmitting visible light is preferably included. In that case, it is preferable that the conductive layer be provided in contact with the light guide plate and have a higher refractive index with respect to light in a wavelength range from 800 nm to 1000 nm than the light guide plate. In addition, the conductive layer preferably functions as an electrode of a capacitive touch sensor.

In the above, the first light-emitting element preferably includes a first pixel electrode, a light-emitting layer, and a first electrode. The light-receiving element preferably includes a second pixel electrode, an active layer, and a second electrode. In that case, the light-emitting layer and the active layer preferably contain different organic compounds from each other. The first pixel electrode and the second pixel electrode are preferably provided over one plane.

Alternatively, in the above, the first light-emitting element preferably includes a first pixel electrode, a light-emitting layer, and a common electrode. The light-receiving element preferably includes a second pixel electrode, an active layer, and the common electrode. In that case, the light-emitting layer and the active layer preferably contain different organic compounds from each other. It is preferable that the first pixel electrode and the second pixel electrode be provided over one plane and the common electrode include a portion overlapping with the first pixel electrode with the light-emitting layer therebetween and a portion overlapping with the second pixel electrode with the active layer therebetween.

Alternatively, in the above, the first light-emitting element preferably includes a first pixel electrode, a common layer, a light-emitting layer, and a common electrode. The light-receiving element preferably includes a second pixel electrode, the common layer, an active layer, and the common electrode. In that case, the light-emitting layer and the active layer preferably contain different organic compounds from each other. The first pixel electrode and the second pixel electrode are preferably provided over one plane. The common layer preferably includes a portion overlapping with the first pixel electrode and the light-emitting layer and a portion overlapping with the second pixel electrode and the active layer. The common electrode preferably includes a portion overlapping with the first pixel electrode with the common layer and the light-emitting layer therebetween and a portion overlapping with the second pixel electrode with the common layer and the active layer therebetween.

Alternatively, in the above, the first light-emitting element preferably includes a first pixel electrode, a light-emitting layer, and a first electrode. The light-receiving element preferably includes a second pixel electrode, an active layer, and a second electrode. In that case, the first pixel electrode and the second pixel electrode are preferably provided over different planes. It is preferable that the light-emitting layer contain an organic compound and the active layer contain silicon.

One embodiment of the present invention is a system including any of the above-described display devices, an arithmetic portion, and a memory portion. The display device has a function of obtaining first biological data including data on a fingerprint or a vein of a user and a function of obtaining second biological data including data on oxygen saturation, a blood sugar level, or a neutral fat concentration of the user. The memory portion has a function of storing a first learning model and a second learning model. The arithmetic portion has a function of executing authentication on the basis of the first learning model and the first biological data and a function of executing anomaly detection on the basis of the second learning model and the second biological data.

Effect of the Invention

With one embodiment of the present invention, a display device having a photosensing function can be provided. A display device having a biometric authentication function typified by fingerprint authentication can be provided. A display device having both a touch panel function and a biometric authentication function can be provided. A highly convenient display device can be provided. A multifunctional display device can be provided. A display device having a novel structure can be provided.

With one embodiment of the present invention, a display device having a function of obtaining user's health conditions can be provided. A display device that can manage user's health can be provided.

Note that the description of these effects does not preclude the existence of other effects. One embodiment of the present invention does not have to have all of these effects. Effects other than these can be derived from the description of the specification, the drawings, the claims, and the like.

BRIEF DESCRIPTION OF THE DRAWINGS

FIG. 10A and FIG. 10B are diagrams illustrating structure examples of a display device.

MODE FOR CARRYING OUT THE INVENTION

Figure 1A:
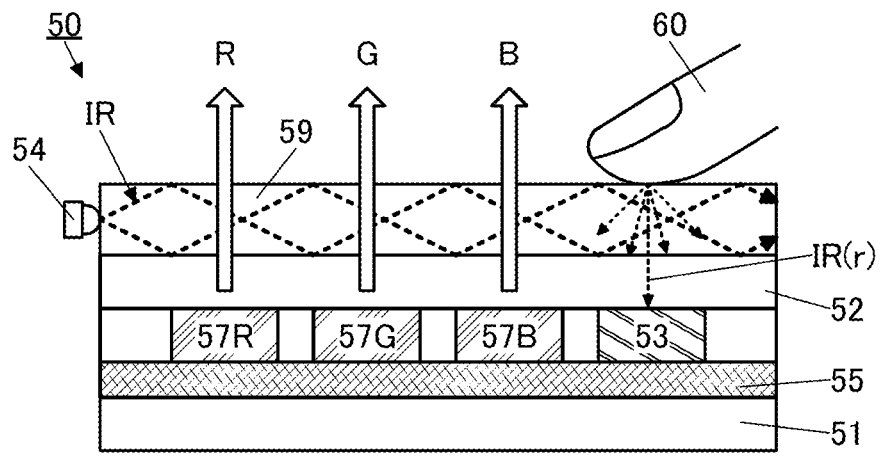
FIG. 1A, FIG. 1B, FIG. 1D, and FIG. 1F to FIG. 1H are diagrams illustrating structure examples of a display device.

Hereinafter, embodiments will be described with reference to the drawings. Note that the embodiments can be implemented in many different modes, and it will be readily understood by those skilled in the art that modes and details thereof can be changed in various ways without departing from the spirit and scope thereof. Thus, the present invention should not be construed as being limited to the following description of the embodiments.

Note that in structures of the invention described below, the same portions or portions having similar functions are denoted by the same reference numerals in different drawings, and description thereof is not repeated. Furthermore, the same hatch pattern is used for the portions having similar functions, and the portions are not especially denoted by reference numerals in some cases.

Note that in each drawing described in this specification, the size, the layer thickness, or the region of each component is exaggerated for clarity in some cases. Therefore, they are not limited to the illustrated scale.

Note that in this specification and the like, the ordinal numbers such as "first" and "second" are used in order to avoid confusion among components and do not limit the number.

In this specification and the like, a display panel that is one embodiment of a display device has a function of displaying (outputting) an image or the like on (to) a display surface. Therefore, the display panel is one embodiment of an output device.

In this specification and the like, a substrate of a display panel to which a connector such as an FPC (Flexible Printed Circuit) or a TCP (Tape Carrier Package) is attached, or a substrate on which an IC is mounted by a COG (Chip On Glass) method or the like is referred to as a display panel module, a display module, or simply a display panel or the like in some cases.

Note that in this specification and the like, a touch panel that is one embodiment of a display device has a function of displaying an image or the like on a display surface and a function of a touch sensor that senses the contact, press, approach, or the like of a sensing target such as a finger or a stylus with or to the display surface. Thus, the touch panel is one embodiment of an input/output device.

A touch panel can also be referred to as, for example, a display panel (or a display device) with a touch sensor, or a display panel (or a display device) having a touch sensor function. A touch panel can include a display panel and a touch sensor panel. Alternatively, a touch panel can have a function of a touch sensor in the display panel or on the surface of the display panel.

In this specification and the like, a substrate of a touch panel on which a connector and an IC are mounted is referred to as a touch panel module, a display module, or simply a touch panel or the like in some cases.

Embodiment 1

In this embodiment, structure examples of a display device of one embodiment of the present invention are described.

The display device of one embodiment of the present invention includes a display element that exhibits visible light and a light-receiving element (a light-receiving device) that receives infrared light. The display element is preferably a light-emitting element (also referred to as a first light-emitting element (device)). Furthermore, the light-receiving element is preferably a photoelectric conversion element.

The display device includes a substrate (also referred to as a first substrate) and a light guide plate. The display element and the light-receiving element are arranged between the first substrate and the light guide plate. In addition, the display device includes a light-emitting element (also referred to as a second light-emitting element) that emits infrared light to a side surface of the light guide plate.

Visible light is emitted from the display element to the outside through the light guide plate. A plurality of such display elements arranged in a matrix are included in the display device, so that an image can be displayed.

Infrared light incident on the side surface of the light guide plate diffuses while repeating total reflection inside the light guide plate. Here, when an object touches a surface of the light guide plate (a surface opposite to the surface on the first substrate side), infrared light is scattered at an interface between the light guide plate and the object, and part of the scattered light enters the light-receiving element. When receiving infrared light, the light-receiving element can convert the light into an electric signal in accordance with the intensity of the infrared light and output the electric signal. In the case where a plurality of light-receiving elements arranged in a matrix are included in the display device, positional data, shape, or the like of the object that touches the light guide plate can be sensed. That is, the display device can function as an image sensor panel, a touch sensor panel, or the like.

Furthermore, using infrared light, which cannot be seen by the user, as the light that diffuses inside the light guide plate enables image capturing or sensing by the light-receiving element without a reduction in visibility of a displayed image.

Light emitted by the second light-emitting element preferably includes infrared light, and further preferably includes near-infrared light. In particular, near-infrared light having one or more peaks in the range of a wavelength greater than or equal to 700 nm and less than or equal to 2500 nm can be suitably used. In particular, the use of light having one or more peaks in the range of a wavelength greater than or equal to 750 nm and less than or equal to 1000 nm is preferable because it permits an extensive choice of a material used for an active layer of the light-receiving element.

When a fingertip touches the light guide plate of the display device, an image of the shape of a fingerprint can be captured. A fingerprint has a depression and a projection. When a finger touches the light guide plate, infrared light is likely to be scattered by the projection of the fingerprint touching the light guide plate. Therefore, the intensity of infrared light that enters the light-receiving element overlapping with the projection of the fingerprint is high, and the intensity of infrared light that enters the light-receiving element overlapping with the depression is low. Utilizing this, a fingerprint image can be captured. A device including the display device of one embodiment of the present invention can perform fingerprint authentication, which is a kind of biometric authentication, by utilizing a captured fingerprint image.

In addition, the display device can also capture an image of a blood vessel, especially a vein of a finger, a hand, or the like. For example, light having a wavelength of 760 nm and its vicinity is not absorbed by reduced hemoglobin in a vein, so that the position of the vein can be sensed by making an image from reflected light from a palm, a finger, or the like that is received by the light-receiving element. A device including the display device of one embodiment of the present invention can perform vein authentication, which is a kind of biometric authentication, by utilizing a captured vein image.

In addition, the device including the display device of one embodiment of the present invention can also perform fingerprint authentication and vein authentication at the same time. Thus, biometric authentication with higher level of security can be executed without increasing the number of components.

In particular, the light-receiving element is preferably an element that can receive not only infrared light but also visible light. Accordingly, light emitted by the first light-emitting element is reflected by a user's finger and the reflected light is received by the light-receiving element, so that an image of the shape of a fingerprint can be captured. Furthermore, an image of the shape of a vein can be captured with infrared light. Accordingly, both fingerprint authentication and vein authentication can be executed in one display device. Moreover, fingerprint image capturing and vein image capturing may be executed either at different timings or at the same time. In the case where fingerprint image capturing and vein image capturing are performed at the same time, image data including both data on the shape of a fingerprint and data on the shape of a vein can be obtained, so that biometric authentication with higher accuracy can be achieved.

The display device of one embodiment of the present invention may have a function of sensing user's health conditions. For example, by utilizing changes in reflectance and transmittance with respect to visible light and infrared light in accordance with a change in blood oxygen saturation, temporal modulation of the oxygen saturation is obtained, from which a heart rate can be measured. Furthermore, a glucose concentration in dermis, a neutral fat concentration in the blood, or the like can also be measured with infrared light or visible light. The device including the display device of one embodiment of the present invention can be used as a health care device capable of obtaining index data on user's health conditions.

Furthermore, a second substrate may be provided between the first substrate and the light guide plate. As the second substrate, a sealing substrate for sealing the light-emitting element, a protective film, or the like can be used, for example. In addition, a resin layer may be provided between the first substrate and the light guide plate to attach the first substrate and the light guide plate to each other. Using, as the resin layer, a material having a lower refractive index with respect to infrared light emitted by the second light-emitting element than the light guide plate can inhibit infrared light that diffuses inside the light guide plate from reaching the resin layer side and entering the light-receiving element.

A conductive layer that transmits visible light may be provided in contact with the light guide plate. In this case, it is preferable to use, as the conductive layer, a material having a higher refractive index with respect to infrared light emitted by the second light-emitting element than the light guide plate in order that the infrared light can also diffuse into the conductive layer. The conductive layer provided in contact with the light guide plate can be used as an electrostatic shielding film, for example. The conductive layer can also function as an electrode of a capacitive touch sensor, for example. Furthermore, the conductive layer can also be used as electrodes or wirings of a variety of sensors or functional elements.

Here, in the case where a light-emitting element is used as the display element, an EL element such as an OLED (Organic Light Emitting Diode) or a QLED (Quantum-dot Light Emitting Diode) is preferably used. As a light-emitting substance included in the EL element, a substance which emits fluorescence (a fluorescent material), a substance which emits phosphorescence (a phosphorescent material), a substance which exhibits thermally activated delayed fluorescence (a thermally activated delayed fluorescent (TADF) material), an inorganic compound (e.g., a quantum dot material), and the like can be given. Alternatively, an LED such as a micro-LED (Light Emitting Diode) can be used as the light-emitting element.

As the light-receiving element, a pn photodiode or a pin photodiode can be used, for example. The light-receiving element functions as a photoelectric conversion element that senses light incident on the light-receiving element and generates charge. The amount of generated charge in the photoelectric conversion element is determined depending on the amount of incident light. It is particularly preferable to use an organic photodiode including a layer containing an organic compound as the light-receiving element. An organic photodiode, which is easily made thin, lightweight, and large in area and has a high degree of freedom for shape and design, can be used in a variety of display devices.

The light-emitting element can have a stacked-layer structure including a light-emitting layer between a pair of electrodes, for example. The light-receiving element can have a stacked-layer structure including an active layer between a pair of electrodes. A semiconductor material can be used for the active layer of the light-receiving element. For example, an inorganic semiconductor material such as silicon can be used.

An organic compound is preferably used for the active layer of the light-receiving element. In that case, one electrode of the light-emitting element and one electrode of the light-receiving element (the electrodes are also referred to as pixel electrodes) are preferably provided on the same plane. It is further preferable that the other electrode of the light-emitting element and the other electrode of the light-receiving element be an electrode (also referred to as a common electrode) formed using one continuous conductive layer. It is still further preferable that the light-emitting element and the light-receiving element include a common layer. Thus, the manufacturing process of the light-emitting element and the light-receiving element can be simplified, so that the manufacturing cost can be reduced and the manufacturing yield can be increased.

More specific examples are described below with reference to drawings.

Structure Example 1 of Display Device

Structure Example

A schematic view of a display device 50 is illustrated in FIG. 1A. The display device 50 includes a substrate 51, a substrate 52, a light guide plate 59, a light-receiving element 53, a light-emitting element 54, a light-emitting element 57R, a light-emitting element 57G, a light-emitting element 57B, a functional layer 55, and the like.

The light-emitting element 57R, the light-emitting element 57G, the light-emitting element 57B, and the light-receiving element 53 are provided between the substrate 51 and the substrate 52.

The light-emitting element 57R, the light-emitting element 57G, and the light-emitting element 57B emit red (R) light, green (G) light, and blue (B) light, respectively.

The display device 50 includes a plurality of pixels arranged in a matrix. One pixel includes one or more subpixels. One subpixel includes one light-emitting element. For example, the pixel can have a structure including three subpixels (e.g., three colors of R, G, and B or three colors of yellow (Y), cyan (C), and magenta (M)) or four subpixels (e.g., four colors of R, G, B, and white (W) or four colors of R, G, B, and Y). The pixel further includes the light-receiving element 53. The light-receiving element 53 may be provided in all the pixels or may be provided in some of the pixels. In addition, one pixel may include a plurality of light-receiving elements 53.

The light guide plate 59 is provided over the substrate 52. As the light guide plate 59, a material having a high light-transmitting property with respect to visible light and infrared light is preferably used. For example, a material whose light-transmitting property with respect to both light having a wavelength of 600 nm and light having a wavelength of 800 nm is 80% or more, preferably 85% or more, further preferably 90% or more, still further preferably 95% or more and 100% or less can be used.

Furthermore, as the light guide plate 59, a material having a high refractive index with respect to light emitted by the light-emitting element 54 is preferably used. For example, a material whose refractive index with respect to light having a wavelength of 800 nm is higher than or equal to 1.2 and lower than or equal to 2.5, preferably higher than or equal to 1.3 and lower than or equal to 2.0, further preferably higher than or equal to 1.4 and lower than or equal to 1.8 can be used.

Moreover, it is preferable that the light guide plate 59 and the substrate 52 be provided in contact with each other or be attached to each other with a resin layer or the like. In this case, the substrate 52 or the resin layer in contact with the light guide plate 59 preferably has a lower refractive index with respect to light in a wavelength range from 800 nm to 1000 nm than the light guide plate 59, in at least a portion in contact with the light guide plate 59.

The light-emitting element 54 is provided in the vicinity of a side surface of the light guide plate 59. The light-emitting element 54 can emit infrared light IR to the side surface of the light guide plate 59. As the light-emitting element 54, a light-emitting element that can emit infrared light including light having the above-described wavelength can be used. As the light-emitting element 54, an EL element such as an OLED or a QLED or an LED can be used. A plurality of light-emitting elements 54 may be provided along the side surface of the light guide plate 59.

FIG. 1A illustrates a finger 60 touching a surface of the light guide plate 59. Part of the infrared light IR that diffuses inside the light guide plate 59 is reflected or scattered by a contact portion between the light guide plate 59 and the finger 60. Then, part of scattered light IR(r) of the infrared light IR enters the light-receiving element 53, and the contact of the finger 60 with the light guide plate 59 can be sensed. That is, the display device 50 can function as a touch panel.

The functional layer 55 includes a circuit that drives the light-emitting element 57R, the light-emitting element 57G, and the light-emitting element 57B and a circuit that drives the light-receiving element 53. The functional layer 55 is provided with a switch, a transistor, a capacitor, a wiring, and the like. Note that in the case where the light-emitting element 57R, the light-emitting element 57G, the light-emitting element 57B, and the light-receiving element 53 are driven by a passive-matrix method, a structure not provided with a switch or a transistor may be employed.

Figure 1B:
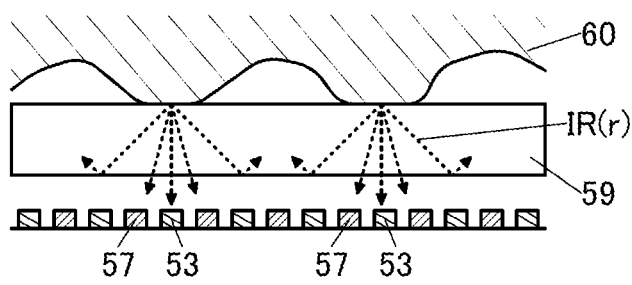

The display device 50 may have a function of sensing a fingerprint of the finger 60. FIG. 1B schematically illustrates an enlarged view of the contact portion in a state where the finger 60 touches the light guide plate 59. FIG. 1B illustrates light-emitting elements 57 and the light-receiving elements 53 that are alternately arranged.

The fingerprint of the finger 60 is formed of depressions and projections. Therefore, as illustrated in FIG. 1B, the projections of the fingerprint touch the light guide plate 59, and the scattered light IR(r) is generated at the contact surfaces.

As illustrated in FIG. 1B, the scattered light IR(r), which is scattered at the contact surface between the finger 60 and the light guide plate 59, can be scattered isotropically from the contact surface. In the intensity distribution of the scattered light IR(r), the intensity in an almost perpendicular direction to the contact surface is the highest, and the intensity becomes lower as the angle becomes larger to an oblique direction. Thus, the intensity of light received by the light-receiving element 53 positioned directly below the contact surface (i.e., overlapping with the contact surface) is the highest. Of the scattered light IR(r), light at greater than or equal to a predetermined scattering angle is totally reflected at the other surface (a surface opposite to the contact surface) of the light guide plate 59 and does not reach the light-receiving element 53 side, as illustrated in FIG. 1B.

In the case where an arrangement interval between the light-receiving elements 53 is smaller than a distance between two projections of a fingerprint, preferably smaller than a distance between a depression and a projection adjacent to each other, a clear fingerprint image can be obtained. The distance between a depression and a projection of a human's fingerprint is approximately 200 μm; thus, the arrangement interval between the light-receiving elements 53 is, for example, less than or equal to 400 μm, preferably less than or equal to 200 μm, further preferably less than or equal to 150 μm, still further preferably less than or equal to 100 μm, even still further preferably less than or equal to 50 μm and greater than or equal to 1 μm, preferably greater than or equal to 10 μm, further preferably greater than or equal to 20 μm.

At the contact surface between the finger 60 and the light guide plate 59, not only scattering but also reflection of the infrared light IR might occur. The reflection angle of the reflected light changes depending on the incident angle of the infrared light IR; therefore, the intensity distribution might differ between the reflected light and the scattered light IR(r). However, in the case where the distance between the contact surface and the light-receiving element 53 is short enough with respect to the arrangement interval between the light-receiving elements 53, the difference in intensity distribution between the scattered light IR(r) and the reflected light is negligible and hardly influences the clarity of a captured image.

Figure 1C:
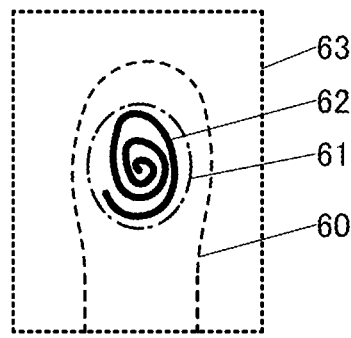
FIG. 1C and FIG. 1E are diagrams illustrating examples of images.

FIG. 1C illustrates an example of a fingerprint image captured with the display device 50. In an image-capturing range 63 in FIG. 1C, the outline of the finger 60 is indicated by a dashed line and the outline of a contact portion 61 is indicated by a dashed-dotted line. In the contact portion 61, a high-contrast image of a fingerprint 62 can be captured owing to a difference in the amount of light incident on the light-receiving elements 53.

Figure 1D:
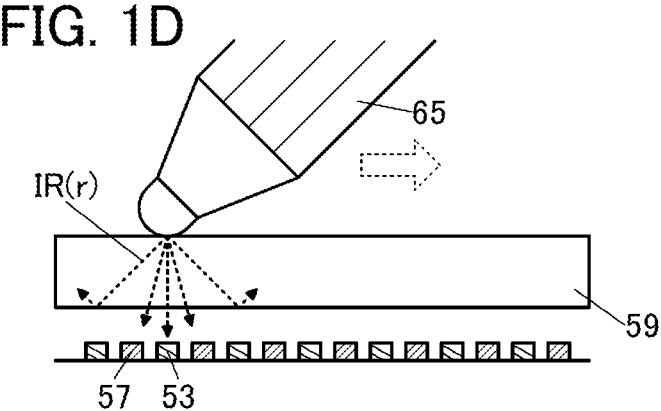

The display device 50 can also function as a touch panel or a pen tablet. FIG. 1D shows a state in which a tip of a stylus 65 slides in a direction indicated by a dashed arrow while the tip of the stylus 65 touches the light guide plate 59.

As shown in FIG. 1D, when the scattered light IR(r) scattered by the contact surface between the tip of the stylus 65 and the light guide plate 59 enters the light-receiving element 53 that is positioned in a portion overlapping with the scattering surface, the position of the tip of the stylus 65 can be sensed with high accuracy.

Figure 1E:
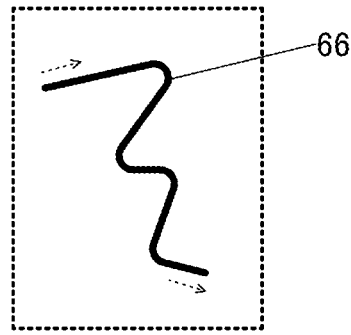

FIG. 1E illustrates an example of a path 66 of the stylus 65 that is sensed by the display device 50. The display device 50 can sense the position of a sensing target, such as the stylus 65, with high position accuracy, so that high-definition drawing can be performed using a drawing application or the like.

Figure 1F:
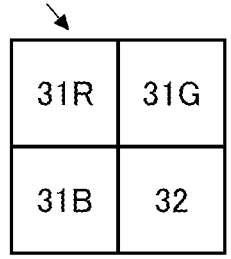
Figure 1G:
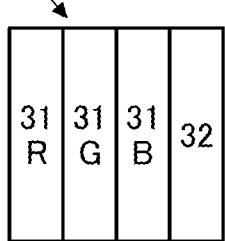
Figure 1H:
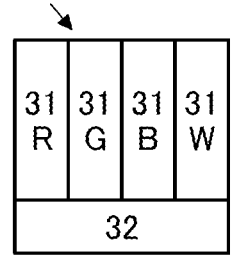

Here, FIG. 1F to FIG. 1H illustrate examples of a pixel 30 that can be used in the display device 50.

The pixel 30 illustrated in FIG. 1F and FIG. 1G includes a red (R) pixel 31R, a green (G) pixel 31G, and a blue (B) pixel 31B, each of which functions as a subpixel for display, and a pixel 32 functioning as a light-receiving pixel. The pixel 31R, the pixel 31G, and the pixel 31B include one or more light-emitting elements 57R, one or more light-emitting elements 57G, and one or more light-emitting elements 57B, respectively. The pixel 32 includes one or more light-receiving elements 53.

FIG. 1F illustrates an example in which three subpixels and the pixel 32 are provided in a matrix of 2×2. FIG. 1G illustrates an example in which the three subpixels and the pixel 32 are laterally arranged in a line.

The pixel 30 illustrated in FIG. 1H is an example including a white (W) pixel 31W. The pixel 31W includes one or more white light-emitting elements. Here, the four subpixels are laterally arranged in a line and the pixel 32 is provided below the four subpixels.

Note that the pixel structure is not limited to the above structure, and a variety of arrangement methods can be employed.

Application Example

An example of a case where an image of a user's fingerprint and an image of a user's blood vessel are captured is described below. The display device can execute a mode of performing image capturing of a fingerprint with the use of visible light, a mode of performing image capturing of a blood vessel with the use of infrared light, and a mode of performing image capturing of a fingerprint and a blood vessel as one image with the use of both visible light and infrared light.

Figure 2A:
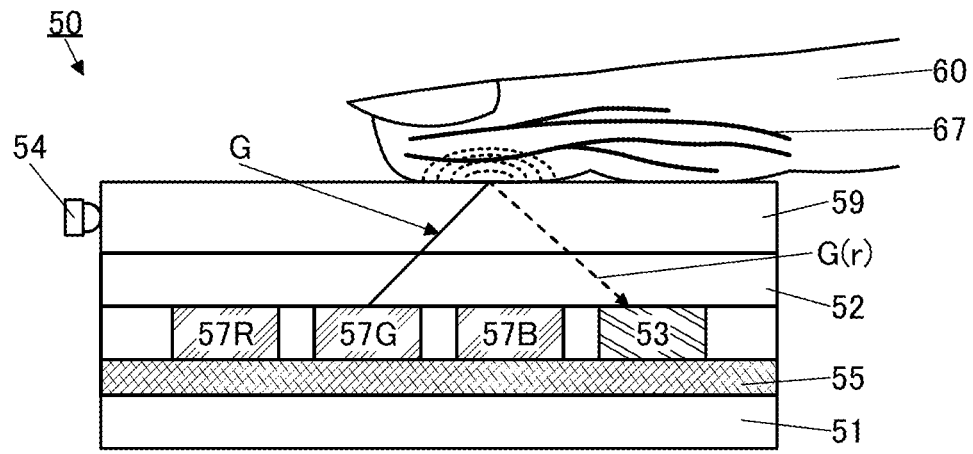
FIG. 2A to FIG. 2C are diagrams illustrating a structure example of a display device.

FIG. 2A illustrates a state in which image capturing of a fingerprint is performed with the use of visible light. In this case, the light-emitting element 54 is not made to emit light, and the light-emitting element 57G is made to emit light. Green light G emitted by the light-emitting element 57G is delivered to a surface of the finger 60, and part of the light is reflected or scattered. Then, part of the scattered light G(r) enters the light-receiving element 53. Since the light-receiving elements 53 are arranged in a matrix, an image of the fingerprint of the finger 60 can be obtained by mapping the intensity of the scattered light G(r) sensed by each light-receiving element 53.

Figure 2B:
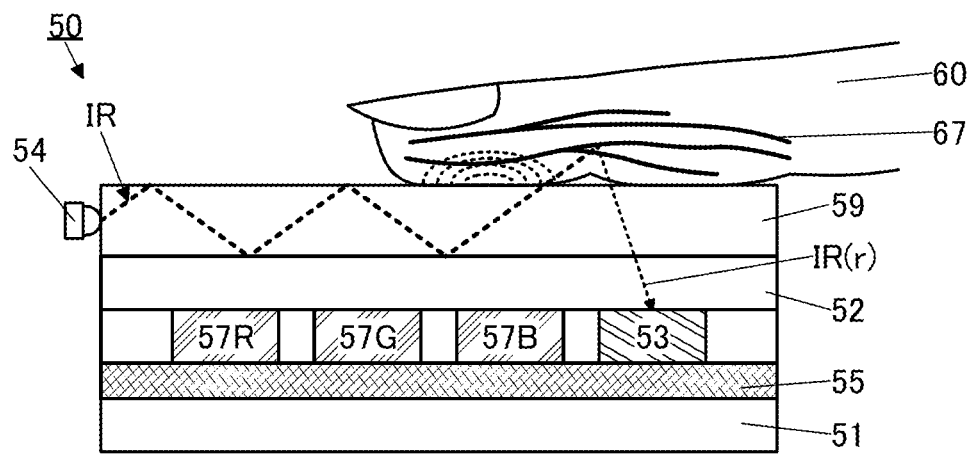

FIG. 2B illustrates a state in which image capturing of a blood vessel is performed with the use of infrared light. In this case, the light-emitting element 57R, the light-emitting element 57G, and the light-emitting element 57B are not made to emit light; and the light-emitting element 54 is made to emit light. Part of the infrared light IR which diffuses inside the light guide plate 59 passes through the contact portion between the light guide plate 59 and the finger 60 and reaches the inside of the finger 60. Then, part of the infrared light IR is reflected or scattered by a blood vessel 67 positioned inside the finger 60, and the reflected light IR(r) enters the light-receiving element 53. By mapping the intensity of the incident light IR(r) in a manner similar to that described above, an image of the blood vessel 67 can be obtained.

Figure 2C:
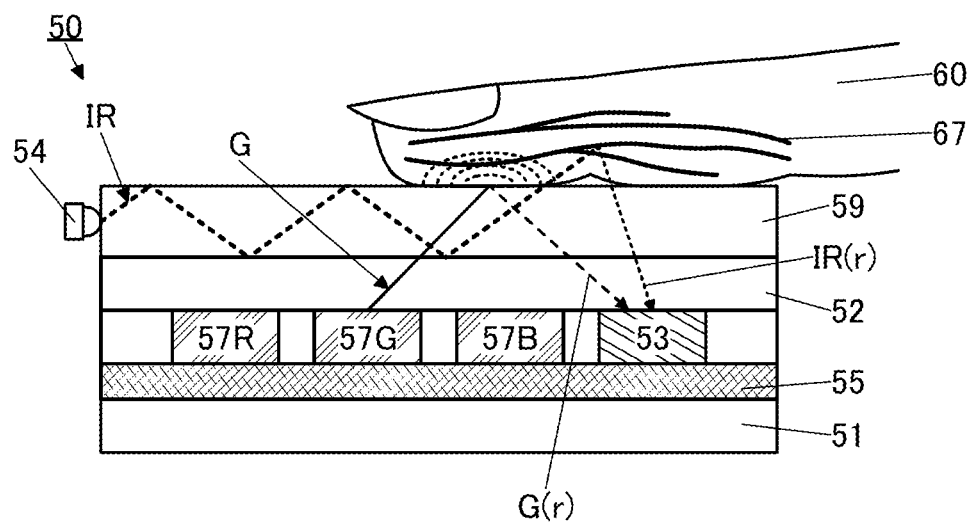

FIG. 2C illustrates a state in which image capturing with the use of visible light and image capturing with the use of infrared light are concurrently performed. The scattered light G(r) and the scattered light IR(r) enter the light-receiving element 53. By performing mapping in a manner similar to that described above without discriminating between the intensities of two kinds of scattered light obtained by the light-receiving element 53, an image reflecting both the shape of the fingerprint and the shape of the blood vessel 67 can be obtained.

Here, the blood vessel 67 includes a vein and an artery. In the case of obtaining an image of a vein inside the finger 60, the image can be used for vein authentication.

Furthermore, the reflectance with respect to infrared light or visible light of an artery (arteriole) inside the finger 60 changes in accordance with a change in blood oxygen saturation. By obtaining this change over time, i.e., temporal modulation of blood oxygen saturation, data on the pulse wave can be obtained. Thus, the user's heart rate can be measured. Although an example in which data on the pulse wave is obtained with the infrared light IR is described here, measurement is possible with the use of visible light.

The data obtained by capturing images of the inside of the finger 60 and the blood vessel 67 can be oxygen saturation in blood, a neutral fat concentration in blood, a glucose concentration in blood or dermis, and the like. The blood sugar level can be estimated from the glucose concentration. This kind of data is an indicator of user's health conditions; changes of daily health conditions can be monitored by measuring the data once or more a day. A device including the display device of one embodiment of the present invention can obtain biological data at the same time when the device executes fingerprint authentication or vein authentication; accordingly, management of user's health is unconsciously possible without troubling the user.

Note that although the light-emitting element 57G that emits green light is used as a light source of visible light in the above description, without limitation thereto, the light-emitting element 57R or the light-emitting element 57B may be used or two or more of the three light-emitting elements may be used. As the light-emitting element 54, as well as one kind of light-emitting element, a plurality of light-emitting elements that emit infrared light with different wavelengths or a light-emitting element that emits continuous-wavelength infrared light may be used. As a light source used for fingerprint authentication, vein authentication, or obtainment of biological data, a light source that emits light of a wavelength appropriate for the uses can be selected and used.

Structure Example 2 of Display Device

A structure example of a display device whose structure is partly different from that of the above-described structure example is described below.

Structure Example 2-1

Figure 3A:
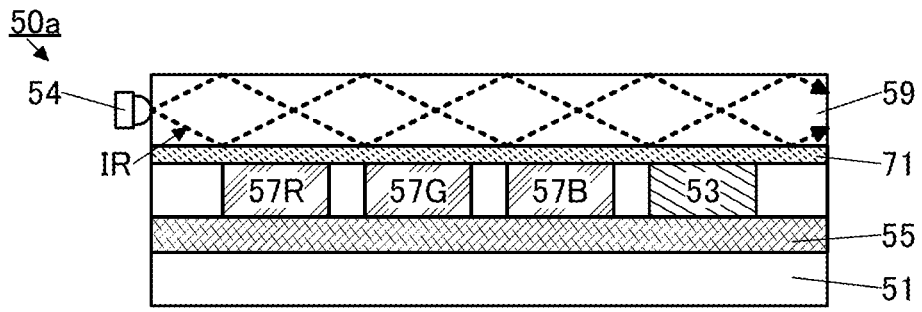
FIG. 3A to FIG. 3D are diagrams illustrating structure examples of a display device.

A display device 50a illustrated in FIG. 3A is chiefly different from the above-described display device 50 in including a resin layer 71 instead of the substrate 52.

For the resin layer 71, a material that transmits visible light can be used. Furthermore, the resin layer 71 may have a function of attaching the substrate 51 and the light guide plate 59.

The resin layer 71 is provided in contact with the light guide plate 59. Here, the refractive index with respect to light in a wavelength range from 800 nm to 1000 nm of at least a portion in contact with the light guide plate 59 of the resin layer 71 is preferably lower than that of the light guide plate 59. Thus, as illustrated in FIG. 3A, the infrared light IR can be totally reflected at an interface between the light guide plate 59 and the resin layer 71.

Structure Example 2-2

Figure 3B:
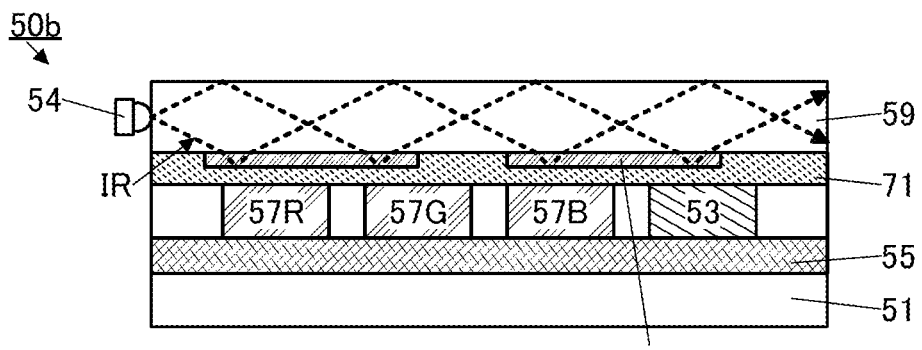

A display device 50b illustrated in FIG. 3B is chiefly different from the above-described display device 50a in including a conductive layer 72.

The conductive layer 72 is provided in contact with the light guide plate 59. Here, an example in which the conductive layer 72 is positioned between the light guide plate 59 and the resin layer 71 is illustrated.

By being applied with a predetermined potential, the conductive layer 72 can function as an electrostatic shielding film. The conductive layer 72 can suitably prevent electric noise input from the outside through the light guide plate 59 from reaching a circuit or the like included in the display device 50b.

Furthermore, the conductive layer 72 can also function as an electrode of a sensor element such as a touch sensor. The conductive layer 72 is particularly preferably used as an electrode of a capacitive touch sensor.

For the conductive layer 72, a conductive material that transmits visible light can be used. Furthermore, a conductive material that transmits the infrared light IR, which is emitted by the light-emitting element 54, can be suitably used for the conductive layer 72.

A conductive material having a higher refractive index with respect to light in a wavelength range from 800 nm to 1000 nm than the light guide plate 59 is preferably used for at least a portion in contact with the light guide plate 59 of the conductive layer 72. Thus, as illustrated in FIG. 3B, a structure can be employed in which the infrared light IR diffuses into not only the light guide plate 59 but also the conductive layer 72. In addition, because the refractive index with respect to light in the above-described wavelength range of the conductive layer 72 is higher than that of the resin layer 71, the infrared light IR can be totally reflected at an interface between the conductive layer 72 and the resin layer 71.

Although an example including the resin layer 71 is described here, a structure including the substrate 52 may be used as well.

Structure Example 2-3

Figure 3C:
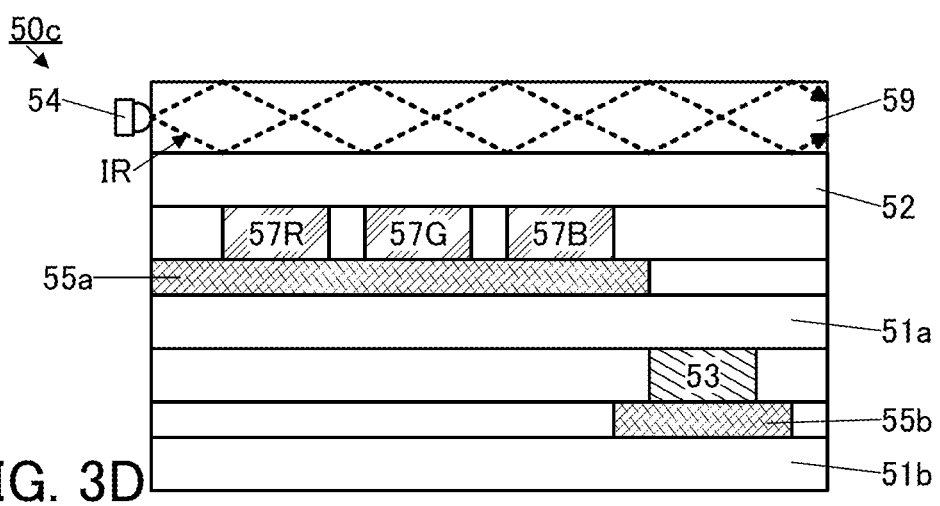

A display device 50c illustrated in FIG. 3C is an example in which the light-emitting element 57R and the like are provided on a surface different from a surface on which the light-receiving element 53 is provided. The display device 50c includes a substrate 51a, a substrate 51b, a functional layer 55a, a functional layer 55b, and the like.

The functional layer 55a is a layer including a circuit that drives the light-emitting element 57R and the like and is provided over the substrate 51a. Furthermore, the functional layer 55b is a layer including a circuit that drives the light-receiving element 53 and is provided over the substrate 51b. The substrate 51a and the substrate 51b are preferably fixed with an adhesive layer (not illustrated) or the like.

In this case, an inorganic semiconductor material such as silicon can be used for an active layer included in the light-receiving element 53. In this case, single crystal silicon, polycrystalline silicon, amorphous silicon, or the like can be selected and used for the active layer in accordance with the wavelength of the infrared light IR. Note that an example in which the functional layer 55b and the light-receiving element 53 are stacked over the substrate 51b is described here; in the case where a semiconductor substrate is used as the substrate 51b, the substrate 51b may form a part of the functional layer 55b and a part of the light-receiving element 53.

Structure Example 2-4

Figure 3D:
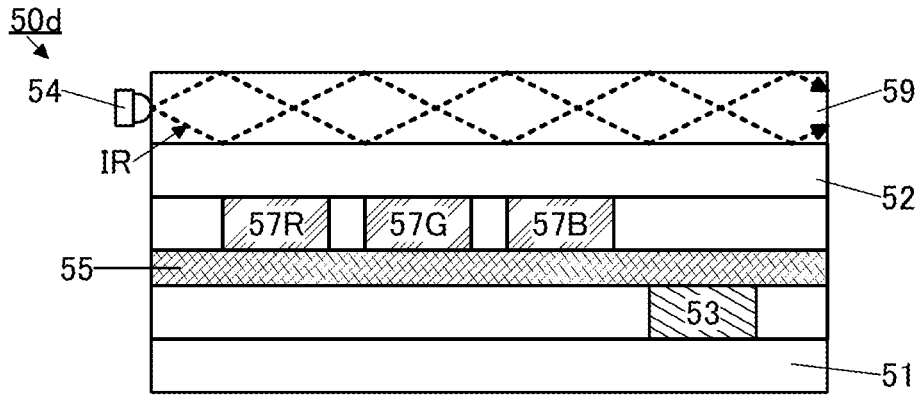

A display device 50d illustrated in FIG. 3D is chiefly different from the above-described structure example in that the light-emitting element 57R and the like and the light-receiving element 53 are provided with the functional layer 55 therebetween.

The inorganic semiconductor material described above, such as silicon, can be used for the active layer included in the light-receiving element 53. Furthermore, in the case where a semiconductor substrate is used as the substrate 51, the substrate 51 may form a part of the active layer or the like of the light-receiving element 53.

In the display device 50c and the display device 50d, a structure in which the resin layer 71 is provided instead of the substrate 52 may be used; or a structure including the conductive layer 72 may be used.

Structure Example of Light Guide Plate

The light guide plate that can be used in the display device of one embodiment of the present invention is provided in a display portion of an electronic device and can also serve as part of a housing functioning as a display surface or a touch surface, for example. In this case, the light guide plate functions as a protective member that protects the light-emitting elements, the light-receiving element, the functional layer, and the like. For example, tempered glass, a flexible film, or the like can be used as the light guide plate.

Figure 4A:
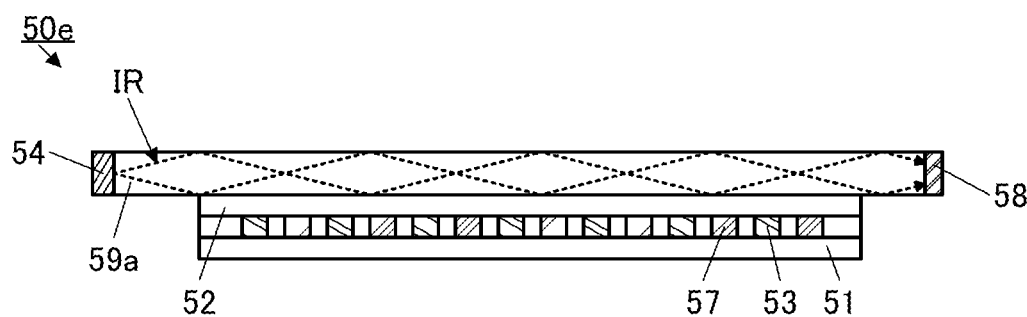
FIG. 4A to FIG. 4C are diagrams illustrating structure examples of a display device.

FIG. 4A illustrates a structure example of a display device 50e. The display device 50e has a structure provided with a light guide plate 59a over the substrate 52. FIG. 4A is an example including the light guide plate 59a having a flat-plate shape.

The light-emitting element 54 that emits the infrared light IR is provided along one end portion of the light guide plate 59a. In addition, a reflective layer 58 is provided on the side opposite to the side provided with the light-emitting element 54 of the light guide plate 59a. The reflective layer 58 has a function of reflecting the infrared light IR. With the reflective layer 58, the intensity distribution of the infrared light IR that diffuses inside the light guide plate 59a can be made uniform.

Figure 4B:
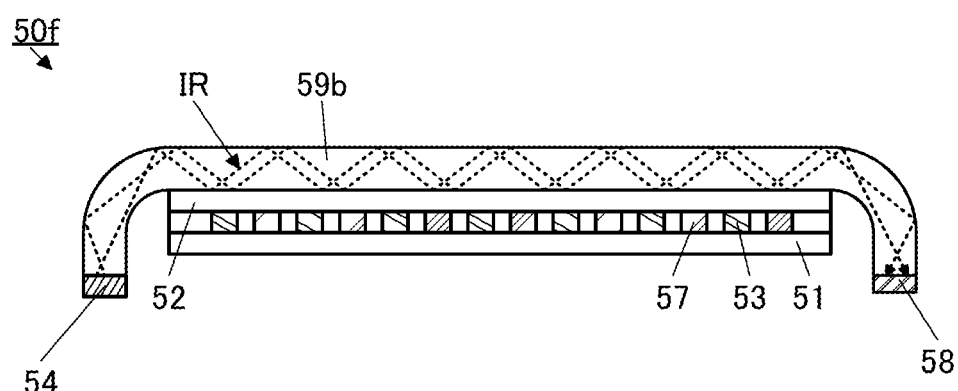

FIG. 4B illustrates a structure example of a display device 50f including a light guide plate 59b whose end portions are both curved.

In a manner similar to that of the light guide plate 59a, the light guide plate 59b is provided with the light-emitting element 54 along its one end portion and is provided with the reflective layer 58 along the other end portion. The infrared light IR diffuses inside the light guide plate 59b.

The structure in which both end portions of the light guide plate 59b are curved and the light-emitting element 54 and the reflective layer 58 are provided along the end portions is preferable in order to reduce the area of a non-display region (also referred to as a bezel) that surrounds a display portion of an electronic device using the display device 50f.

In some cases, part of the infrared light IR is not totally reflected and is delivered to the outside in the curved portions of the light guide plate 59b, and the intensity of the infrared light IR that diffuses inside the light guide plate 59b might be decreased. However, for example, adequately thinning the light guide plate 59b can increase the total reflection rate of the infrared light IR. For example, the thickness of the light guide plate 59b is less than or equal to 2 mm, preferably less than or equal to 1 mm, further preferably less than or equal to 0.8 mm, still further preferably less than or equal to 0.7 mm, and more than or equal to 10 μm, preferably more than or equal to 30 μm, further preferably more than or equal to 50 μm, whereby the reduction in the intensity of the infrared light IR in the light guide plate 59b can be inhibited.

Figure 4C:
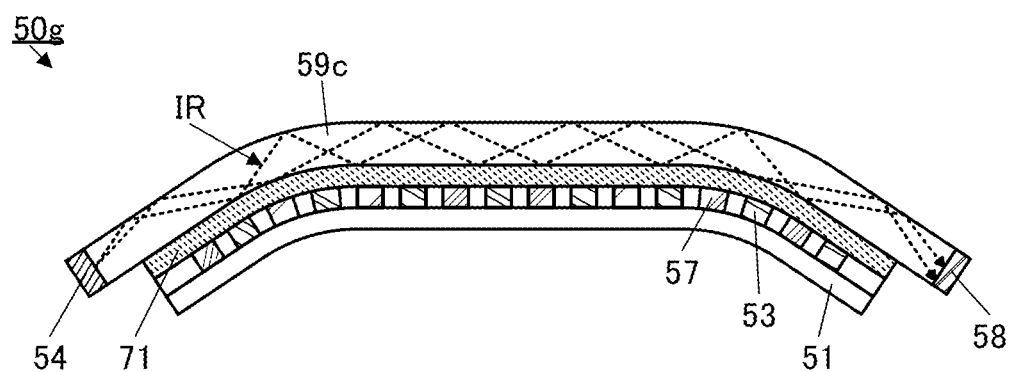

FIG. 4C illustrates a structure example of a display device 50g in which the substrate 51 and the like are provided so as to be curved along a light guide plate 59c that is curved partly.

For the substrate 51, a flexible material can be used. In the case where the radii of curvature of the curved portions of the light guide plate 59c are sufficiently large, an inorganic insulating substrate such as a glass substrate can be used as the substrate 51. Furthermore, a material including an organic resin or the like is preferably used for the substrate 51.

Moreover, FIG. 4C illustrates an example in which the substrate 51 and the light guide plate 59c are attached to each other with the resin layer 71. In the case where the substrate 51 is provided along a curved surface of the light guide plate 59c, such a structure in which the substrate 52 is not provided and attachment is performed with the resin layer 71 is preferable to facilitate bonding between the substrate 51 and the light guide plate 59c. In addition to that, the distance between the light-receiving element 53 and the light guide plate 59c can be made small, producing synergistic effects such as higher accuracy of positional sensing and clear image capturing.

Although an example in which the light guide plate 59c includes a curved portion and a flat portion is illustrated in FIG. 4C, the light guide plate 59c may have an entirely curved shape without including a flat portion.

The above is the description of the structure examples of the light guide plate.

Structure Example 3 of Display Device

More specific examples of the display device of one embodiment of the present invention will be described below.

Structure Example 3-1

Figure 5A:
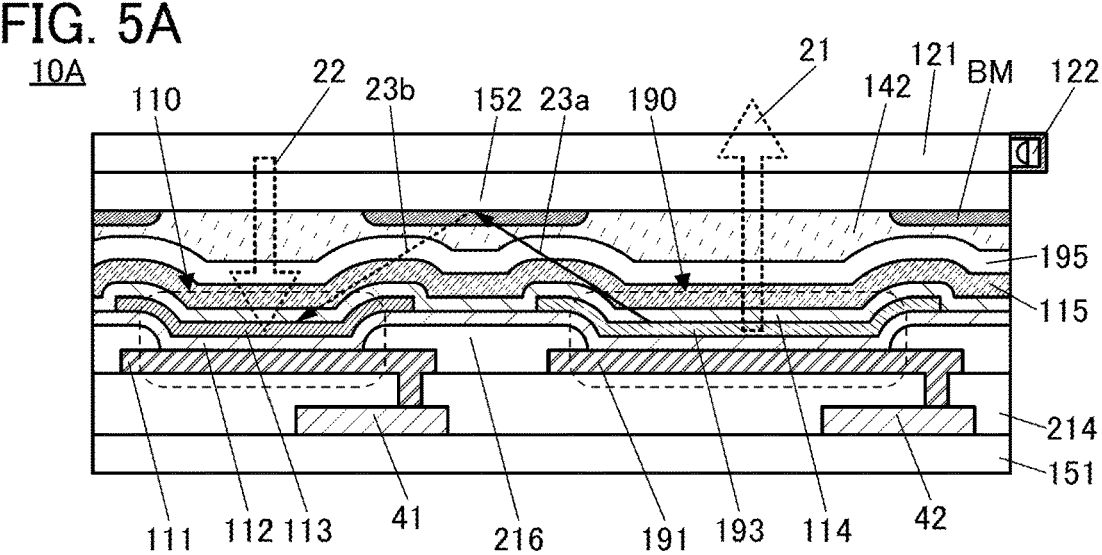
FIG. 5A to FIG. 5C are diagrams illustrating structure examples of a display device.

FIG. 5A illustrates a schematic cross-sectional view of a display device 10A.

The display device 10A includes a light-receiving element 110 and a light-emitting element 190. The light-receiving element 110 includes a pixel electrode 111, a common layer 112, an active layer 113, a common layer 114, and a common electrode 115. The light-emitting element 190 includes a pixel electrode 191, the common layer 112, a light-emitting layer 193, the common layer 114, and the common electrode 115.

The pixel electrode 111, the pixel electrode 191, the common layer 112, the active layer 113, the light-emitting layer 193, the common layer 114, and the common electrode 115 may each have a single-layer structure or a stacked-layer structure.

The pixel electrode 111 and the pixel electrode 191 are positioned over an insulating layer 214. The pixel electrode 111 and the pixel electrode 191 can be formed using the same material in the same step.

The common layer 112 is positioned over the pixel electrode 111 and the pixel electrode 191. The common layer 112 is a layer shared by the light-receiving element 110 and the light-emitting element 190.

The active layer 113 overlaps with the pixel electrode 111 with the common layer 112 therebetween. The light-emitting layer 193 overlaps with the pixel electrode 191 with the common layer 112 therebetween. The active layer 113 includes a first organic compound, and the light-emitting layer 193 includes a second organic compound that is different from the first organic compound.

The common layer 114 is positioned over the common layer 112, the active layer 113, and the light-emitting layer 193. The common layer 114 is a layer shared by the light-receiving element 110 and the light-emitting element 190.

The common electrode 115 includes a portion overlapping with the pixel electrode 111 with the common layer 112, the active layer 113, and the common layer 114 therebetween. The common electrode 115 further includes a portion overlapping with the pixel electrode 191 with the common layer 112, the light-emitting layer 193, and the common layer 114 therebetween. The common electrode 115 is a layer shared by the light-receiving element 110 and the light-emitting element 190.

In the display device of this embodiment, an organic compound is used for the active layer 113 of the light-receiving element 110. In the light-receiving element 110, the layers other than the active layer 113 can have structures in common with the layers in the light-emitting element 190 (EL element). Therefore, the light-receiving element 110 can be formed concurrently with the formation of the light-emitting element 190 only by adding a step of depositing the active layer 113 in the manufacturing process of the light-emitting element 190. The light-emitting element 190 and the light-receiving element 110 can be formed over one substrate. Accordingly, the light-receiving element 110 can be incorporated into the display device without a significant increase in the number of manufacturing steps.

The display device 10A illustrates an example in which the light-receiving element 110 and the light-emitting element 190 have a common structure except that the active layer 113 of the light-receiving element 110 and the light-emitting layer 193 of the light-emitting element 190 are separately formed. Note that the structures of the light-receiving element 110 and the light-emitting element 190 are not limited thereto. The light-receiving element 110 and the light-emitting element 190 may include separately formed layers other than the active layer 113 and the light-emitting layer 193 (see display devices 10D, 10E, and 10F described later). The light-receiving element 110 and the light-emitting element 190 preferably include at least one layer used in common (common layer). Thus, the light-receiving element 110 can be incorporated into the display device without a significant increase in the number of manufacturing steps.

The display device 10A includes the light-receiving element 110, the light-emitting element 190, a transistor 41, a transistor 42, and the like between a pair of substrates (a substrate 151 and a substrate 152).

The display device 10A also includes a light guide plate 121 on the outside of the substrate 152. A light-emitting element 122 that emits infrared light is provided at an end portion of the light guide plate 121.

In the light-receiving element 110, the common layer 112, the active layer 113, and the common layer 114, which are positioned between the pixel electrode 111 and the common electrode 115, can each also be referred to as an organic layer (a layer including an organic compound). The pixel electrode 111 preferably has a function of reflecting visible light and infrared light. An end portion of the pixel electrode 111 is covered with a bank 216. The common electrode 115 has a function of transmitting visible light and infrared light.

The light-receiving element 110 has a function of sensing light. Specifically, the light-receiving element 110 is a photoelectric conversion element that receives light 22 entering through the light guide plate 121 and converts the light 22 into an electric signal.

A light-blocking layer BM is provided on a surface of the substrate 152 that faces the substrate 151. The light-blocking layer BM has an opening in a position overlapping with the light-receiving element 110 and in a position overlapping with the light-emitting element 190. Providing the light-blocking layer BM can control the range where the light-receiving element 110 senses light.

For the light-blocking layer BM, a material that blocks light emitted from the light-emitting element can be used. The light-blocking layer BM preferably absorbs visible light and infrared light. As the light-blocking layer BM, a black matrix can be formed using a metal material or a resin material containing pigment (e.g., carbon black) or dye, for example. The light-blocking layer BM may have a stacked-layer structure of a red color filter, a green color filter, and a blue color filter.

Here, the light-receiving element 110 senses light that is scattered by a surface of the light guide plate 121. However, in some cases, light emitted from the light-emitting element 190 is reflected inside the display device 10A and enters the light-receiving element 110 without via the light guide plate 121 or the like. The light-blocking layer BM can reduce the influence of such stray light. For example, in the case where the light-blocking layer BM is not provided, light 23a emitted from the light-emitting element 190 is reflected by the substrate 152 and reflected light 23b enters the light-receiving element 110 in some cases. Providing the light-blocking layer BM can inhibit the reflected light 23b from entering the light-receiving element 110. Consequently, noise can be reduced, and the sensitivity of a sensor using the light-receiving element 110 can be increased.

In the light-emitting element 190, the common layer 112, the light-emitting layer 193, and the common layer 114, which are positioned between the pixel electrode 191 and the common electrode 115, can each also be referred to as an EL layer. The pixel electrode 191 preferably has a function of reflecting visible light and infrared light. An end portion of the pixel electrode 191 is covered with the bank 216. The pixel electrode 111 and the pixel electrode 191 are electrically insulated from each other by the bank 216. The common electrode 115 has a function of transmitting visible light and infrared light.

The light-emitting element 190 has a function of emitting visible light. Specifically, the light-emitting element 190 is an electroluminescent element that emits light 21 to the substrate 152 side when voltage is applied between the pixel electrode 191 and the common electrode 115.

It is preferable that the light-emitting layer 193 be formed not to overlap with a light-receiving region of the light-receiving element 110. This inhibits the light-emitting layer 193 from absorbing the light 22, increasing the amount of light with which the light-receiving element 110 is irradiated.

The pixel electrode 111 is electrically connected to a source or a drain of the transistor 41 through an opening provided in the insulating layer 214. The end portion of the pixel electrode 111 is covered with the bank 216.

The pixel electrode 191 is electrically connected to a source or a drain of the transistor 42 through an opening provided in the insulating layer 214. The end portion of the pixel electrode 191 is covered with the bank 216. The transistor 42 has a function of controlling the driving of the light-emitting element 190.

The transistor 41 and the transistor 42 are in contact with a top surface of the same layer (the substrate 151 in FIG. 5A).

At least part of a circuit electrically connected to the light-receiving element 110 and a circuit electrically connected to the light-emitting element 190 are preferably formed using the same material in the same step. In that case, the thickness of the display device can be reduced compared with the case where the two circuits are separately formed, resulting in simplification of the manufacturing steps.

The light-receiving element 110 and the light-emitting element 190 are preferably covered with a protective layer 195. In FIG. 5A, the protective layer 195 is provided on and in contact with the common electrode 115. Providing the protective layer 195 can inhibit entry of impurities such as water into the light-receiving element 110 and the light-emitting element 190, so that the reliability of the light-receiving element 110 and the light-emitting element 190 can be increased. The protective layer 195 and the substrate 152 are bonded to each other with an adhesive layer 142.

Figure 6A:
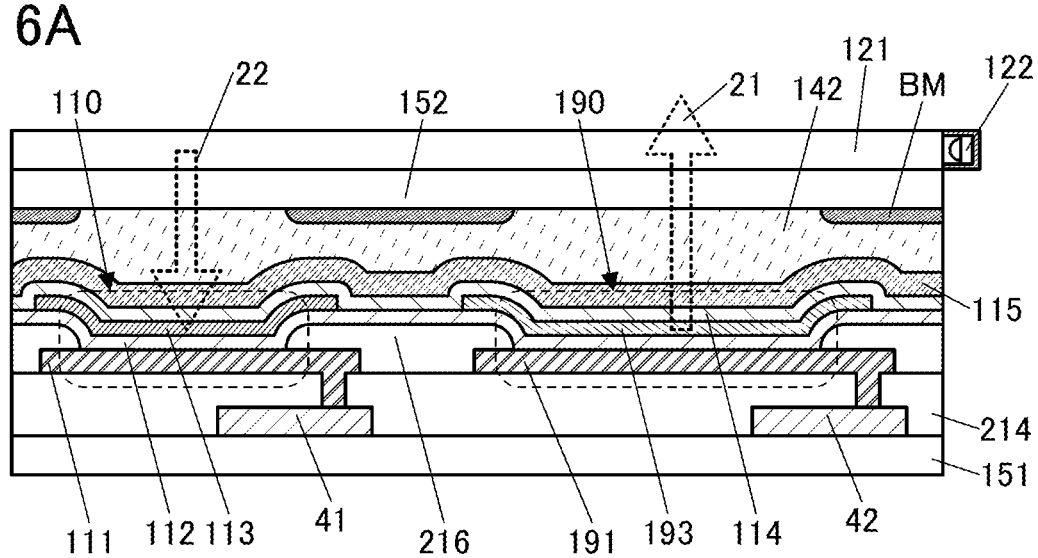
FIG. 6A and FIG. 6B are diagrams illustrating structure examples of a display device.

Note that as illustrated in FIG. 6A, the protective layer over the light-receiving element 110 and the light-emitting element 190 may be omitted. In FIG. 6A, the common electrode 115 and the substrate 152 are bonded to each other with the adhesive layer 142.

Figure 6B:
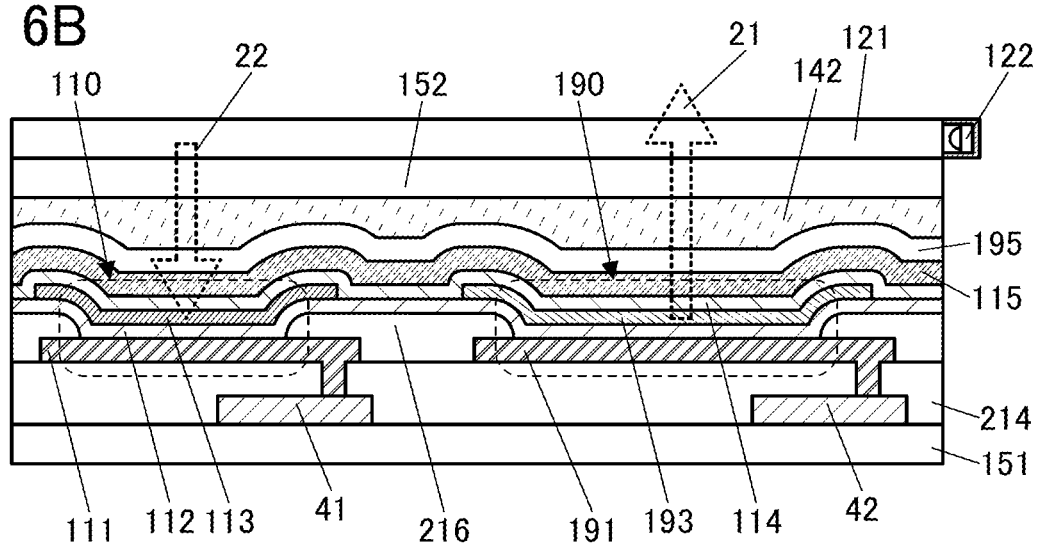

A structure that does not include the light-blocking layer BM as illustrated in FIG. 6B may be employed. This can increase the light-receiving area of the light-receiving element 110, further increasing the sensitivity of the sensor.

Structure Example 3-2

Figure 5B:
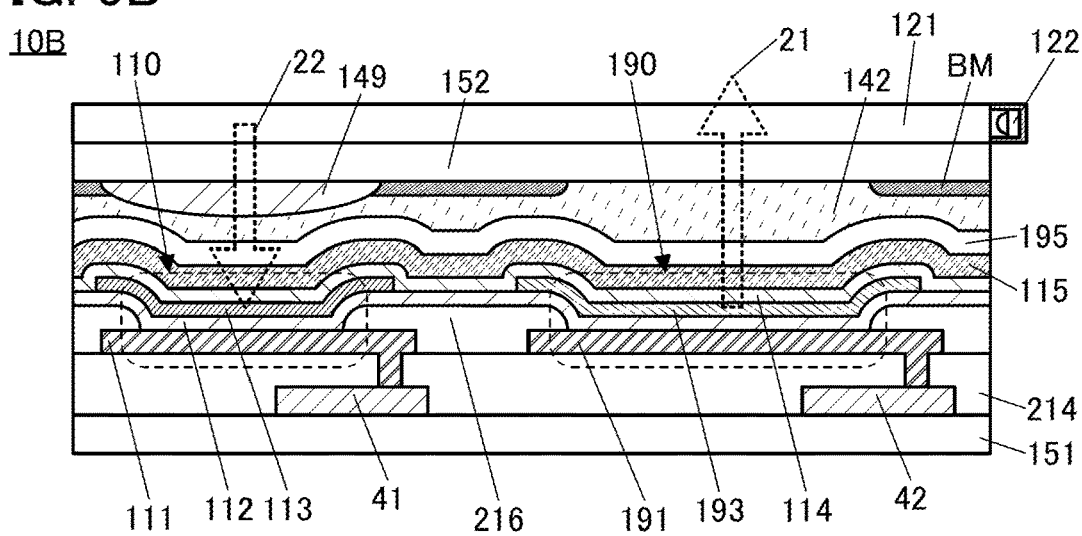

FIG. 5B illustrates a cross-sectional view of a display device 10B. Note that in the description of the display device below, components similar to those of the above-mentioned display device are not described in some cases.

The display device 10B illustrated in FIG. 5B includes a lens 149 in addition to the components of the display device 10A.

The lens 149 is provided in a position overlapping with the light-receiving element 110. In the display device 10B, the lens 149 is provided in contact with the substrate 152. The lens 149 included in the display device 10B is a convex lens having a convex surface on the substrate 151 side. Note that a convex lens having a convex surface on the substrate 152 side may be provided in a region overlapping with the light-receiving element 110.

In the case where the light-blocking layer BM and the lens 149 are formed on the same plane of the substrate 152, their formation order is not limited. FIG. 5B illustrates an example in which the lens 149 is formed first; alternatively, the light-blocking layer BM may be formed first. In FIG. 5B, an end portion of the lens 149 is covered with the light-blocking layer BM.

The display device 10B has a structure in which the light 22 enters the light-receiving element 110 through the lens 149. With the lens 149, the image-capturing range of the light-receiving element 110 can be narrowed as compared to the case where the lens 149 is not provided, thereby inhibiting overlap of the image-capturing ranges between the adjacent light-receiving elements 110. Thus, a clear image with little blurring can be captured. Given that the image-capturing range of the light-receiving element 110 does not change, the lens 149 allows the size of a pinhole (corresponding to the size of an opening in BM that overlaps with the light-receiving element 110 in FIG. 5B) to be increased, compared to the case where the lens 149 is not provided. Hence, providing the lens 149 can increase the amount of light entering the light-receiving element 110.

As a method for forming the lens used in the display device of this embodiment, a lens such as a microlens may be formed directly over the substrate or the light-receiving element, or a lens array formed separately, such as a microlens array, may be bonded to the substrate.

Structure Example 3-3

Figure 5C:
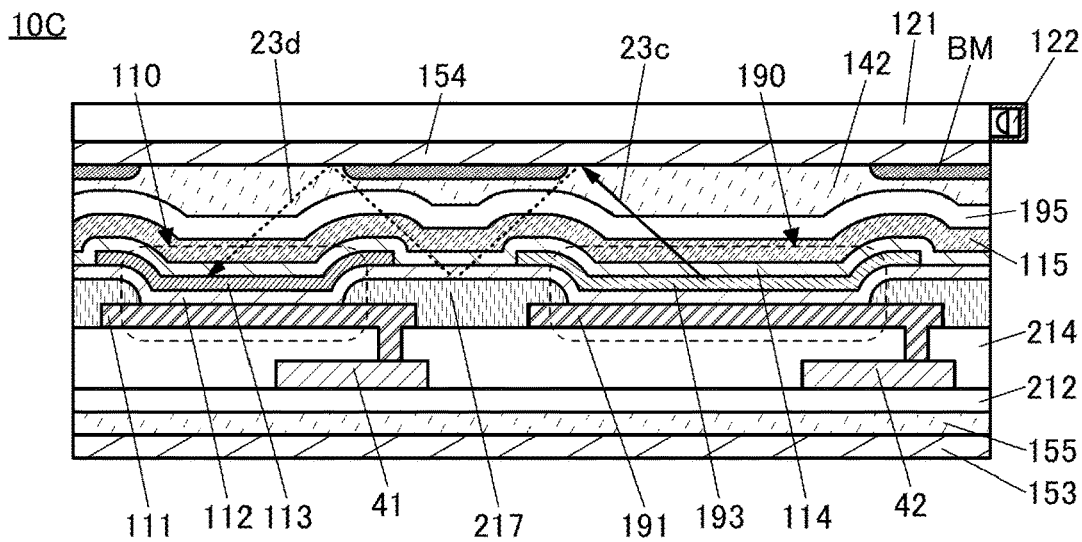

FIG. 5C illustrates a schematic cross-sectional view of a display device 10C. The display device 10C is different from the display device 10A in that the substrate 151, the substrate 152, and the bank 216 are not included but a substrate 153, a substrate 154, an adhesive layer 155, an insulating layer 212, and a bank 217 are included.

The substrate 153 and the insulating layer 212 are bonded to each other with the adhesive layer 155. The substrate 154 and the protective layer 195 are bonded to each other with the adhesive layer 142.

The display device 10C has a structure obtained in such a manner that the insulating layer 212, the transistor 41, the transistor 42, the light-receiving element 110, the light-emitting element 190, and the like are formed over a formation substrate and then transferred onto the substrate 153. The substrate 153 and the substrate 154 preferably have flexibility. Accordingly, the flexibility of the display device 10C can be increased. For example, a resin is preferably used for each of the substrate 153 and the substrate 154.

For each of the substrate 153 and the substrate 154, a polyester resin such as polyethylene terephthalate (PET) or polyethylene naphthalate (PEN), a polyacrylonitrile resin, an acrylic resin, a polyimide resin, a polymethyl methacrylate resin, a polycarbonate (PC) resin, a polyether sulfone (PES) resin, a polyimide resin (e.g., nylon or aramid), a polysiloxane resin, a cycloolefin resin, a polystyrene resin, a polyimide-imide resin, a polyurethane resin, a polyvinyl chloride resin, a polyvinylidene chloride resin, a polypropylene resin, a polytetrafluoroethylene (PTFE) resin, an ABS resin, or cellulose nanofiber can be used, for example. Glass that is thin enough to have flexibility may be used for one or both of the substrate 153 and the substrate 154.

As the substrate included in the display device of this embodiment, a film having high optical isotropy may be used. Examples of the film having high optical isotropy include a triacetyl cellulose (TAC, also referred to as cellulose triacetate) film, a cycloolefin polymer (COP) film, a cycloolefin copolymer (COC) film, and an acrylic film.

The bank 217 preferably absorbs light emitted by the light-emitting element. As the bank 217, a black matrix can be formed using a resin material containing a pigment or dye, for example. Moreover, the bank 217 can be formed of a colored insulating layer by using a brown resist material.

In some cases, light 23c emitted by the light-emitting element 190 is reflected by the substrate 154 and the bank 217 and reflected light 23d enters the light-receiving element 110. In other cases, the light 23c passes through the bank 217 and is reflected by a transistor, a wiring, or the like, and thus reflected light enters the light-receiving element 110. When the bank 217 absorbs the light 23c, the reflected light 23d can be inhibited from entering the light-receiving element 110. Consequently, noise can be reduced, and the sensitivity of a sensor using the light-receiving element 110 can be increased.

The bank 217 preferably absorbs at least light having a wavelength that is sensed by the light-receiving element 110. For example, in the case where the light-receiving element 110 senses red light emitted by the light-emitting element 190, the bank 217 preferably absorbs at least red light. For example, when the bank 217 includes a blue color filter, the bank 217 can absorb the red light 23c and thus the reflected light 23d can be inhibited from entering the light-receiving element 110.

Structure Example 3-4

Although the light-emitting element and the light-receiving element include two common layers in the above examples, one embodiment of the present invention is not limited thereto. Examples in which common layers have different structures are described below.

Figure 7A:
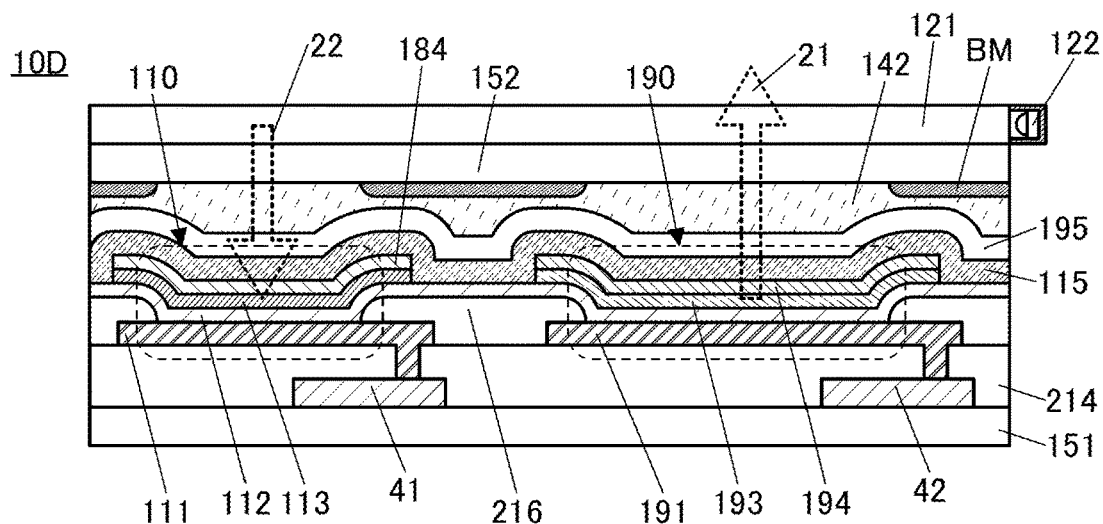
FIG. 7A to FIG. 7C are diagrams illustrating structure examples of a display device.

FIG. 7A illustrates a schematic cross-sectional view of a display device 10D. The display device 10D is different from the display device 10A in that the common layer 114 is not included and a buffer layer 184 and a buffer layer 194 are included. The buffer layer 184 and the buffer layer 194 may each have a single-layer structure or a stacked-layer structure.

In the display device 10D, the light-receiving element 110 includes the pixel electrode 111, the common layer 112, the active layer 113, the buffer layer 184, and the common electrode 115. In the display device 10D, the light-emitting element 190 includes the pixel electrode 191, the common layer 112, the light-emitting layer 193, the buffer layer 194, and the common electrode 115.

The display device 10D shows an example in which the buffer layer 184 between the common electrode 115 and the active layer 113 and the buffer layer 194 between the common electrode 115 and the light-emitting layer 193 are formed separately. As the buffer layer 184 and the buffer layer 194, one or both of an electron-injection layer and an electron-transport layer can be formed, for example.

Figure 7B:
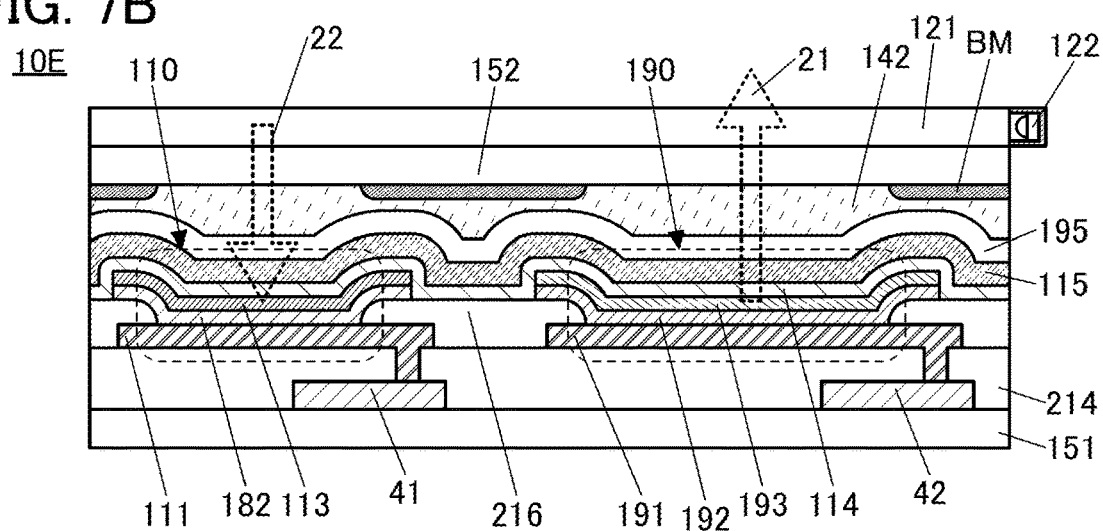

FIG. 7B illustrates a schematic cross-sectional view of a display device 10E. The display device 10E is different from the display device 10A in that the common layer 112 is not included and a buffer layer 182 and a buffer layer 192 are included. The buffer layer 182 and the buffer layer 192 may each have a single-layer structure or a stacked-layer structure.

In the display device 10E, the light-receiving element 110 includes the pixel electrode 111, the buffer layer 182, the active layer 113, the common layer 114, and the common electrode 115. In the display device 10E, the light-emitting element 190 includes the pixel electrode 191, the buffer layer 192, the light-emitting layer 193, the common layer 114, and the common electrode 115.

The display device 10E shows an example in which the buffer layer 182 between the pixel electrode 111 and the active layer 113 and the buffer layer 192 between the pixel electrode 191 and the light-emitting layer 193 are formed separately. As the buffer layer 182 and the buffer layer 192, one or both of a hole-injection layer and a hole-transport layer can be formed, for example.

Figure 7C:
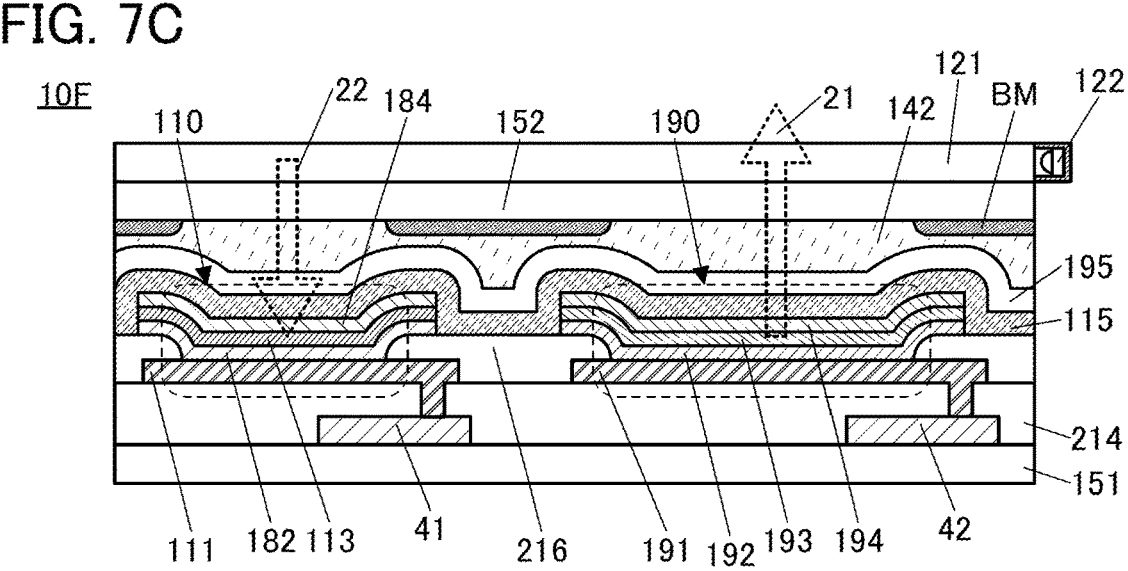

FIG. 7C illustrates a schematic cross-sectional view of a display device 10F. The display device 10F is different from the display device 10A in that the common layer 112 and the common layer 114 are not included and the buffer layer 182, the buffer layer 184, the buffer layer 192, and the buffer layer 194 are included.

In the display device 10F, the light-receiving element 110 includes the pixel electrode 111, the buffer layer 182, the active layer 113, the buffer layer 184, and the common electrode 115. In the display device 10F, the light-emitting element 190 includes the pixel electrode 191, the buffer layer 192, the light-emitting layer 193, the buffer layer 194, and the common electrode 115.

In the formation of the light-receiving element 110 and the light-emitting element 190, not only the active layer 113 and the light-emitting layer 193 but also other layers can be formed separately.

The display device 10F shows an example in which the light-receiving element 110 and the light-emitting element 190 do not have a common layer between the pair of electrodes (the pixel electrode 111 or the pixel electrode 191 and the common electrode 115). The light-receiving element 110 and the light-emitting element 190 included in the display device 10F can be formed in the following manner: the pixel electrode 111 and the pixel electrode 191 are formed over the insulating layer 214 using the same material in the same step; the buffer layer 182, the active layer 113, and the buffer layer 184 are formed over the pixel electrode 111, and the buffer layer 192, the light-emitting layer 193, and the buffer layer 194 are formed over the pixel electrode 191; and then, the common electrode 115 is formed to cover the buffer layer 184, the buffer layer 194, and the like.

Note that the formation order of the stacked-layer structure of the buffer layer 182, the active layer 113, and the buffer layer 184 and the stacked-layer structure of the buffer layer 192, the light-emitting layer 193, and the buffer layer 194 is not particularly limited. For example, after the buffer layer 182, the active layer 113, and the buffer layer 184 are deposited, the buffer layer 192, the light-emitting layer 193, and the buffer layer 194 may be formed. By contrast, the buffer layer 192, the light-emitting layer 193, and the buffer layer 194 may be formed before the buffer layer 182, the active layer 113, and the buffer layer 184 are deposited. Alternate deposition of the buffer layer 182, the buffer layer 192, the active layer 113, the light-emitting layer 193, and the like in this order is also possible.

Structure Example 4 of Display Device

More specific structure examples of the display device of one embodiment of the present invention will be described below.

Structure Example 4-1

Figure 8:
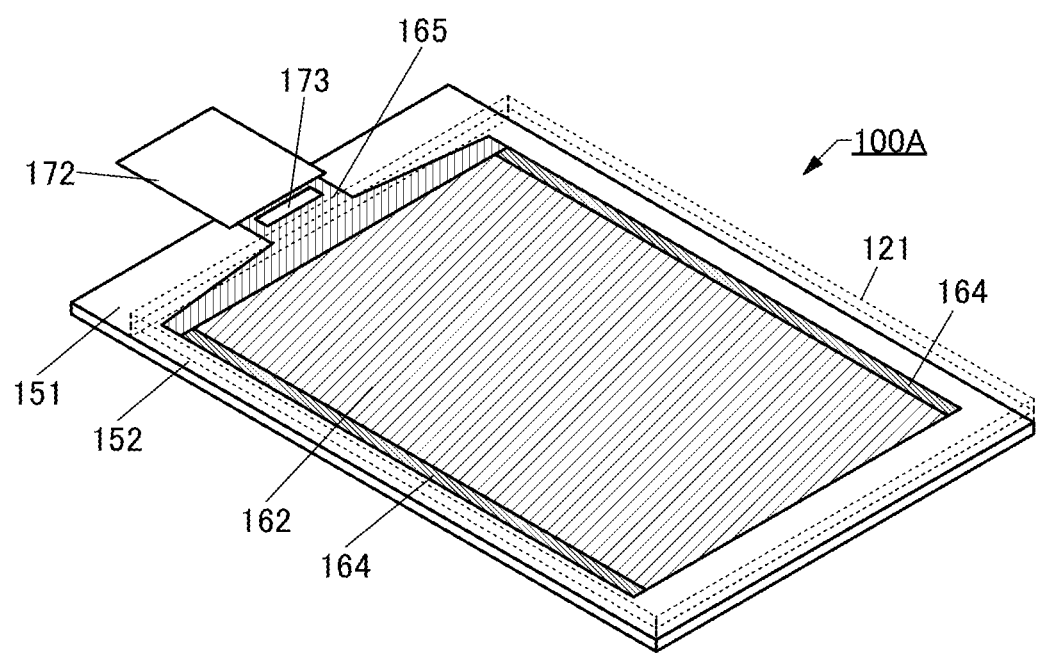
FIG. 8 is a diagram illustrating a structure example of a display device.

FIG. 8 illustrates a perspective view of a display device 100A.

The display device 100A has a structure in which the substrate 151 and the substrate 152 are bonded to each other. The light guide plate 121 is provided over the substrate 152. In FIG. 8, the substrate 152 and the light guide plate 121 are denoted by dashed lines.

The display device 100A includes a display portion 162, a circuit 164, a wiring 165, and the like. FIG. 8 illustrates an example in which the display device 100A is provided with an IC (integrated circuit) 173 and an FPC 172. Thus, the structure illustrated in FIG. 8 can be regarded as a display module including the display device 100A, the IC 173, and the FPC 172.

As the circuit 164, a scan line driver circuit can be used.

The wiring 165 has a function of supplying a signal and power to the display portion 162 and the circuit 164. The signal and power are input to the wiring 165 from the outside through the FPC 172 or from the IC 173.

FIG. 8 illustrates an example in which the IC 173 is provided over the substrate 151 by a COG (Chip On Glass) method, a COF (Chip On Film) method, or the like. An IC including a scan line driver circuit, a signal line driver circuit, or the like can be used as the IC 173, for example. Note that the display device 100A and the display module may have a structure that does not include an IC. The IC may be mounted on the FPC 172 by a COF method or the like.

Figure 9:
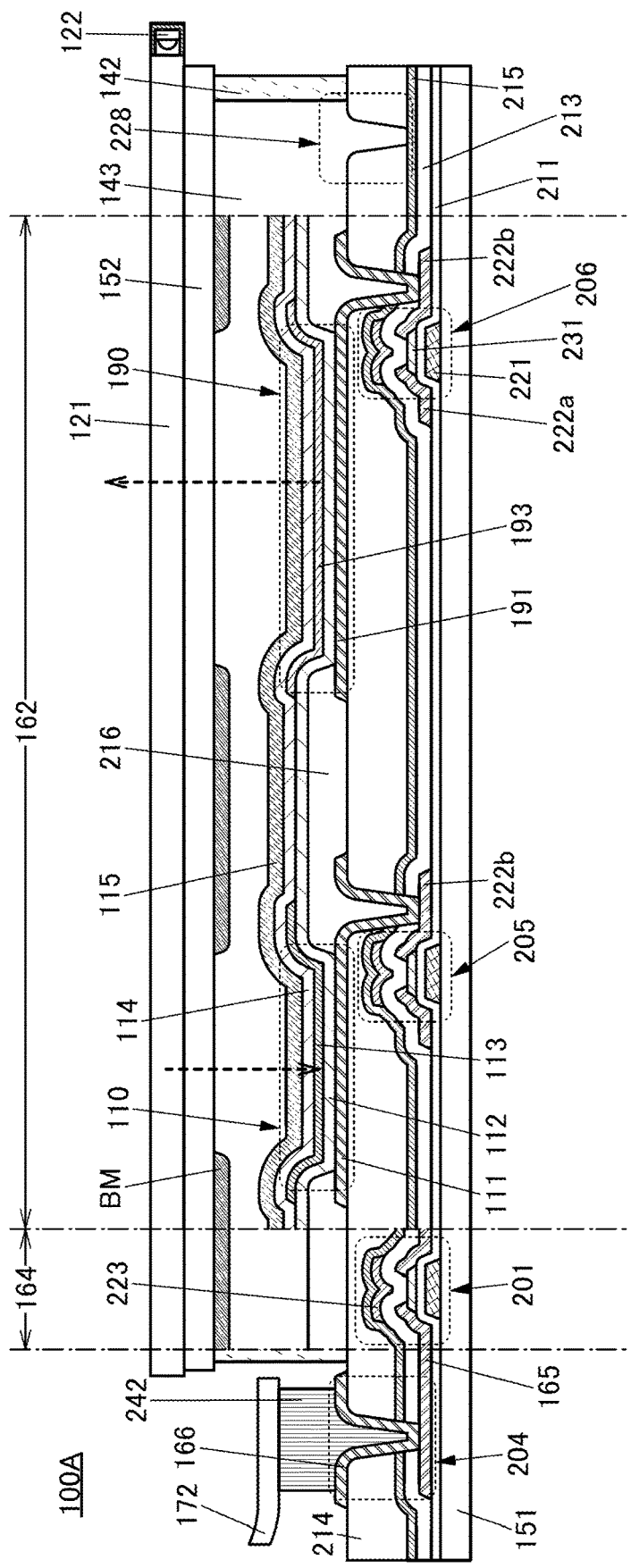
FIG. 9 is a diagram illustrating a structure example of a display device.

FIG. 9 illustrates an example of a cross section of part of a region including the FPC 172, part of a region including the circuit 164, part of a region including the display portion 162, and part of a region including an end portion of the display device 100A illustrated in FIG. 8.

The display device 100A illustrated in FIG. 9 includes a transistor 201, a transistor 205, a transistor 206, the light-emitting element 190, the light-receiving element 110, and the like between the substrate 151 and the substrate 152. The light guide plate 121 is provided over the substrate 152. The light-emitting element 122 is provided at an end portion of the light guide plate 121.

The substrate 152 and the insulating layer 214 are attached to each other with the adhesive layer 142. A solid sealing structure, a hollow sealing structure, or the like can be employed to seal the light-emitting element 190 and the light-receiving element 110. In FIG. 9, a space 143 surrounded by the substrate 152, the adhesive layer 142, and the insulating layer 214 is filled with an inert gas (e.g., nitrogen or argon), that is, a hollow sealing structure is employed. The adhesive layer 142 may be provided to overlap with the light-emitting element 190. The space 143 surrounded by the substrate 152, the adhesive layer 142, and the insulating layer 214 may be filled with a resin different from that of the adhesive layer 142.

The light-emitting element 190 has a stacked-layer structure in which the pixel electrode 191, the common layer 112, the light-emitting layer 193, the common layer 114, and the common electrode 115 are stacked in this order from the insulating layer 214 side. The pixel electrode 191 is connected to a conductive layer 222*b* included in the transistor 206 through an opening provided in the insulating layer 214. The transistor 206 has a function of controlling the driving of the light-emitting element 190. An end portion of the pixel electrode 191 is covered with the bank 216. The pixel electrode 191 includes a material that reflects visible light and infrared light, and the common electrode 115 includes a material that transmits visible light and infrared light.

The light-receiving element 110 has a stacked-layer structure in which the pixel electrode 111, the common layer 112, the active layer 113, the common layer 114, and the common electrode 115 are stacked in this order from the insulating layer 214 side. The pixel electrode 111 is electrically connected to the conductive layer 222*b* included in the transistor 205 through an opening provided in the insulating layer 214. An end portion of the pixel electrode 111 is covered with the bank 216. The pixel electrode 111 includes a material that reflects visible light and infrared light, and the common electrode 115 includes a material that transmits visible light and infrared light.

Light emitted from the light-emitting element 190 is emitted toward the substrate 152 side. Light enters the light-receiving element 110 through the substrate 152 and the space 143. For the substrate 152, a material that has high transmittance with respect to visible light and infrared light is preferably used.

The pixel electrode 111 and the pixel electrode 191 can be formed using the same material in the same step. The common layer 112, the common layer 114, and the common electrode 115 are used in both the light-receiving element 110 and the light-emitting element 190. The light-receiving element 110 and the light-emitting element 190 can have common components except the active layer 113 and the light-emitting layer 193. Thus, the light-receiving element 110 can be incorporated into the display device 100A without a significant increase in the number of manufacturing steps.

The light-blocking layer BM is provided on the surface of the substrate 152 that faces the substrate 151. The light-blocking layer BM has an opening in a position overlapping with the light-receiving element 110 and in a position overlapping with the light-emitting element 190. Providing the light-blocking layer BM can control the range where the light-receiving element 110 senses light. Furthermore, with the light-blocking layer BM, light from the light-emitting element 190 can be inhibited from directly entering the light-receiving element 110. Hence, a sensor with less noise and high sensitivity can be obtained.

The transistor 201, the transistor 205, and the transistor 206 are formed over the substrate 151. These transistors can be formed using the same materials in the same steps.

An insulating layer 211, an insulating layer 213, an insulating layer 215, and the insulating layer 214 are provided in this order over the substrate 151. Parts of the insulating layer 211 function as gate insulating layers of the transistors. Parts of the insulating layer 213 function as gate insulating layers of the transistors. The insulating layer 215 is provided to cover the transistors. The insulating layer 214 is provided to cover the transistors and has a function of a planarization layer. Note that there is no limitation on the number of gate insulating layers and the number of insulating layers covering the transistors, and each insulating layer may have either a single layer or two or more layers.

A material through which impurities such as water and hydrogen do not easily diffuse is preferably used for at least one of the insulating layers that cover the transistors. This allows the insulating layer to serve as a barrier layer. Such a structure can effectively inhibit diffusion of impurities into the transistors from the outside and increase the reliability of the display device.

An inorganic insulating film is preferably used as each of the insulating layer 211, the insulating layer 213, and the insulating layer 215. As the inorganic insulating film, for example, a silicon nitride film, a silicon oxynitride film, a silicon oxide film, a silicon nitride oxide film, an aluminum oxide film, an aluminum nitride film, or the like can be used. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may also be used. A stack including two or more of the above insulating films may also be used.

Here, an organic insulating film often has a lower barrier property than an inorganic insulating film. Therefore, the organic insulating film preferably has an opening in the vicinity of an end portion of the display device 100A. This can inhibit diffusion of impurities from the end portion of the display device 100A through the organic insulating film. Alternatively, in order to prevent the organic insulating film from being exposed at the end portion of the display device 100A, the organic insulating film may be formed such that its end portion is positioned on the inner side compared to the end portion of the display device 100A.

An organic insulating film is suitable for the insulating layer 214 functioning as a planarization layer. Examples of materials that can be used for the organic insulating film include an acrylic resin, a polyimide resin, an epoxy resin, a polyamide resin, a polyimide-amide resin, a siloxane resin, a benzocyclobutene-based resin, a phenol resin, and precursors of these resins.

In a region 228 illustrated in FIG. 9, an opening is formed in the insulating layer 214. This can inhibit diffusion of impurities into the display portion 162 from the outside through the insulating layer 214 even when an organic insulating film is used as the insulating layer 214. Thus, the reliability of the display device 100A can be increased.

Each of the transistor 201, the transistor 205, and the transistor 206 includes a conductive layer 221 functioning as a gate, the insulating layer 211 functioning as the gate insulating layer, a conductive layer 222*a* and the conductive layer 222*b* functioning as a source and a drain, a semiconductor layer 231, the insulating layer 213 functioning as the gate insulating layer, and a conductive layer 223 functioning as a gate. Here, a plurality of layers obtained by processing the same conductive film are shown with the same hatching pattern. The insulating layer 211 is positioned between the conductive layer 221 and the semiconductor layer 231. The insulating layer 213 is positioned between the conductive layer 223 and the semiconductor layer 231.

There is no particular limitation on the structure of the transistors included in the display device of this embodiment. For example, a planar transistor, a staggered transistor, or an inverted staggered transistor can be used. A top-gate or bottom-gate transistor structure may be employed. Alternatively, gates may be provided above and below a semiconductor layer where a channel is formed.

The structure in which the semiconductor layer where a channel is formed is provided between two gates is used for the transistor 201, the transistor 205, and the transistor 206. The two gates may be connected to each other and supplied with the same signal to drive the transistor. Alternatively, a potential for controlling the threshold voltage may be supplied to one of the two gates and a potential for driving may be supplied to the other to control the threshold voltage of the transistor.

There is no particular limitation on the crystallinity of a semiconductor material used for the transistors, and any of an amorphous semiconductor, a single crystal semiconductor, and a semiconductor having crystallinity other than single crystal (a microcrystalline semiconductor, a polycrystalline semiconductor, or a semiconductor partly including crystal regions) may be used. A single crystal semiconductor or a semiconductor having crystallinity is preferably used, in which case deterioration of the transistor characteristics can be suppressed.

A semiconductor layer of a transistor preferably includes a metal oxide (also referred to as an oxide semiconductor). Alternatively, the semiconductor layer of the transistor may include silicon. Examples of silicon include amorphous silicon and crystalline silicon (e.g., low-temperature polysilicon or single crystal silicon).

The semiconductor layer preferably includes indium, M (M is one or more kinds selected from gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more kinds selected from aluminum, gallium, yttrium, and tin.

It is particularly preferable to use an oxide containing indium (In), gallium (Ga), and zinc (Zn) (also referred to as IGZO) for the semiconductor layer.

In the case where the semiconductor layer is an In-M-Zn oxide, the atomic ratio of In to M in a sputtering target used for depositing the In-M-Zn oxide is preferably higher than or equal to 1. Examples of the atomic ratio of the metal elements in such a sputtering target include In:M:Zn=1:1:1, In:M:Zn=1:1:1.2, In:M:Zn=2:1:3, In:M:Zn=3:1:2, In:M:Zn=4:2:3, In:M:Zn=4:2:4.1, In:M:Zn=5:1:6, In:M:Zn=5:1:7, In:M:Zn=5:1:8, In:M:Zn=6:1:6, and In:M:Zn=5:2:5.

A target including a polycrystalline oxide is preferably used as the sputtering target, in which case the semiconductor layer having crystallinity is easily formed. Note that the atomic ratio in the deposited semiconductor layer may vary from the above atomic ratio between metal elements in the sputtering target in a range of ±40%. For example, in the case where the composition of a sputtering target used for the semiconductor layer is In:Ga:Zn=4:2:4.1 [atomic ratio], the composition of the semiconductor layer to be deposited is sometimes in the neighborhood of In:Ga:Zn=4:2:3 [atomic ratio].

Note that when the atomic ratio is described as In:Ga:Zn=4:2:3 or in the neighborhood thereof, the case is included where Ga is greater than or equal to 1 and less than or equal to 3 and Zn is greater than or equal to 2 and less than or equal to 4 with In being 4. When the atomic ratio is described as In:Ga:Zn=5:1:6 or in the neighborhood thereof, the case is included where Ga is greater than 0.1 and less than or equal to 2 and Zn is greater than or equal to 5 and less than or equal to 7 with In being 5. When the atomic ratio is described as In:Ga:Zn=1:1:1 or in the neighborhood thereof, the case is included where Ga is greater than 0.1 and less than or equal to 2 and Zn is greater than 0.1 and less than or equal to 2 with In being 1.

The transistor included in the circuit 164 and the transistor included in the display portion 162 may have the same structure or different structures. A plurality of transistors included in the circuit 164 may have the same structure or two or more kinds of structures. Similarly, a plurality of transistors included in the display portion 162 may have the same structure or two or more kinds of structures.

A connection portion 204 is provided in a region of the substrate 151 that does not overlap with the substrate 152. In the connection portion 204, the wiring 165 is electrically connected to the FPC 172 via a conductive layer 166 and a connection layer 242. On the top surface of the connection portion 204, the conductive layer 166 obtained by processing the same conductive film as the pixel electrode 191 is exposed. Thus, the connection portion 204 and the FPC 172 can be electrically connected to each other through the connection layer 242.

Any of a variety of optical members can be provided between the substrate 152 and the light guide plate 121 or on the outside of the light guide plate 121. Examples of the optical members include a polarizing plate, a retardation plate, a light diffusion layer (a diffusion film or the like), an anti-reflective layer, and a light-condensing film. Furthermore, an antistatic film inhibiting the attachment of dust, a water repellent film suppressing the attachment of stain, a hard coat film inhibiting generation of a scratch caused by the use, a shock absorbing layer, or the like may be provided on the outside of the substrate 152. Note that when a member having high light diffusion properties is provided in contact with the light guide plate 121, infrared light diffusing inside the light guide plate 121 is scattered at the interface therebetween; thus, a member having low light diffusion properties is preferably provided therebetween.

For each of the substrate 151 and the substrate 152, glass, quartz, ceramic, sapphire, a resin, or the like can be used. When a flexible material is used for the substrate 151 and the substrate 152, the flexibility of the display device can be increased.

As the adhesive layer 142, the adhesive layer 155, and the like, a variety of curable adhesives, e.g., a photocurable adhesive such as an ultraviolet curable adhesive, a reactive curable adhesive, a thermosetting adhesive, and an anaerobic adhesive can be used. Examples of these adhesives include an epoxy resin, an acrylic resin, a silicone resin, a phenol resin, a polyimide resin, an imide resin, a PVC (polyvinyl chloride) resin, a PVB (polyvinyl butyral) resin, and an EVA (ethylene vinyl acetate) resin. In particular, a material with low moisture permeability, such as an epoxy resin, is preferred. Alternatively, a two-component resin may be used. An adhesive sheet or the like may be used.

As the connection layer 242, an anisotropic conductive film (ACF), an anisotropic conductive paste (ACP), or the like can be used.

The light-emitting element 190 may be of a top emission type, a bottom emission type, a dual emission type, or the like. A conductive film that transmits visible light is used as the electrode through which light is extracted. A conductive film that reflects visible light is preferably used as the electrode through which light is not extracted.

The light-emitting element 190 includes at least the light-emitting layer 193. The light-emitting element 190 may further include, as a layer other than the light-emitting layer 193, a layer containing a substance with a high hole-injection property, a substance with a high hole-transport property, a hole-blocking material, a substance with a high electron-transport property, a substance with a high electron-injection property, a substance with a bipolar property (a substance with a high electron- and hole-transport property), or the like. For example, the common layer 112 preferably includes one or both of a hole-injection layer and a hole-transport layer. For example, the common layer 114 preferably includes one or both of an electron-transport layer and an electron-injection layer.

The common layer 112, the light-emitting layer 193, and the common layer 114 may use either a low molecular compound or a high molecular compound and may also contain an inorganic compound. The layers that constitute the common layer 112, the light-emitting layer 193, and the common layer 114 can each be formed by a method such as an evaporation method (including a vacuum evaporation method), a transfer method, a printing method, an inkjet method, or a coating method.

The light-emitting layer 193 may contain an inorganic compound such as quantum dots as a light-emitting material.

The active layer 113 of the light-receiving element 110 includes a semiconductor. Examples of the semiconductor include an inorganic semiconductor such as silicon and an organic semiconductor including an organic compound. This embodiment shows an example in which an organic semiconductor is used as the semiconductor included in the active layer. The use of an organic semiconductor is preferable because the light-emitting layer 193 of the light-emitting element 190 and the active layer 113 of the light-receiving element 110 can be formed by the same method (e.g., a vacuum evaporation method) and thus the same manufacturing apparatus can be used.

Examples of an n-type semiconductor material included in the active layer 113 include electron-accepting organic semiconductor materials such as fullerene (e.g., $C_{60}$ and $C_{70}$) and derivatives thereof. As a p-type semiconductor material included in the active layer 113, an electron-donating organic semiconductor material such as copper(II) phthalocyanine (CuPc), tetraphenyldibenzoperiflanthene (DBP), or zinc phthalocyanine (ZnPc) can be given.

For example, the active layer 113 is preferably formed by co-evaporation of an n-type semiconductor and a p-type semiconductor.

As materials that can be used for a gate, a source, and a drain of a transistor and conductive layers such as a variety of wirings and electrodes included in a display device, metals such as aluminum, titanium, chromium, nickel, copper, yttrium, zirconium, molybdenum, silver, tantalum, and tungsten, an alloy containing any of these metals as its main component, and the like can be given. A film containing any of these materials can be used in a single layer or as a stacked-layer structure.

As a light-transmitting conductive material, a conductive oxide such as indium oxide, indium tin oxide, indium zinc oxide, zinc oxide, or zinc oxide containing gallium, or graphene can be used. Alternatively, a metal material such as gold, silver, platinum, magnesium, nickel, tungsten, chromium, molybdenum, iron, cobalt, copper, palladium, or titanium, or an alloy material containing the metal material can be used. Further alternatively, a nitride of the metal material (e.g., titanium nitride) or the like may be used. Note that in the case of using the metal material or the alloy material (or the nitride thereof), the thickness is preferably set small enough to be able to transmit light. A stacked-layer film of any of the above materials can be used as a conductive layer. For example, a stacked-layer film of indium tin oxide and an alloy of silver and magnesium, or the like is preferably used for increased conductivity. These materials can also be used for conductive layers such as a variety of wirings and electrodes that constitute a display device, and conductive layers (conductive layers functioning as a pixel electrode or a common electrode) included in a display element.

As an insulating material that can be used for each insulating layer, for example, a resin such as an acrylic resin or an epoxy resin, and an inorganic insulating material such as silicon oxide, silicon oxynitride, silicon nitride oxide, silicon nitride, or aluminum oxide can be given.

Structure Example 4-2

FIG. 10A illustrates a cross-sectional view of a display device 100B. The display device 100B is different from the display device 100A mainly in that the lens 149 and the protective layer 195 are included.

Providing the protective layer 195 covering the light-receiving element 110 and the light-emitting element 190 can inhibit diffusion of impurities such as water into the light-receiving element 110 and the light-emitting element 190, so that the reliability of the light-receiving element 110 and the light-emitting element 190 can be increased.

In the region 228 in the vicinity of an end portion of the display device 100B, the insulating layer 215 and the protective layer 195 are preferably in contact with each other through an opening in the insulating layer 214. In particular, the inorganic insulating film included in the insulating layer 215 and the inorganic insulating film included in the protective layer 195 are preferably in contact with each other. Thus, diffusion of impurities from the outside into the display portion 162 through the organic insulating film can be inhibited. Thus, the reliability of the display device 100B can be increased.

FIG. 10B illustrates an example in which the protective layer 195 has a three-layer structure. In FIG. 10B, the protective layer 195 includes an inorganic insulating layer 195a over the common electrode 115, an organic insulating layer 195b over the inorganic insulating layer 195a, and an inorganic insulating layer 195c over the organic insulating layer 195b.

An end portion of the inorganic insulating layer 195a and an end portion of the inorganic insulating layer 195c extend beyond an end portion of the organic insulating layer 195b and are in contact with each other. The inorganic insulating layer 195a is in contact with the insulating layer 215 (inorganic insulating layer) through the opening in the insulating layer 214 (organic insulating layer). Accordingly, the light-receiving element 110 and the light-emitting element 190 can be surrounded by the insulating layer 215 and the protective layer 195, whereby the reliability of the light-receiving element 110 and the light-emitting element 190 can be increased.

As described above, the protective layer 195 may have a stacked-layer structure of an organic insulating film and an inorganic insulating film. In that case, an end portion of the inorganic insulating film preferably extends beyond an end portion of the organic insulating film.

The lens 149 is provided on the surface of the substrate 152 that faces the substrate 151. The lens 149 has a convex surface on the substrate 151 side. It is preferable that the light-receiving region of the light-receiving element 110 overlap with the lens 149 and not overlap with the light-emitting layer 193. Thus, the sensitivity and accuracy of a sensor using the light-receiving element 110 can be increased.

The refractive index of the lens 149 with respect to infrared light is preferably greater than or equal to 1.3 and less than or equal to 2.5. The lens 149 can be formed using at least one of an inorganic material and an organic material. For example, a material containing a resin can be used for the lens 149. Moreover, a material containing at least one of an oxide and a sulfide can be used for the lens 149.

Specifically, a resin containing chlorine, bromine, or iodine, a resin containing a heavy metal atom, a resin having an aromatic ring, a resin containing sulfur, or the like can be used for the lens 149. Alternatively, a material containing a resin and nanoparticles of a material having a higher refractive index than the resin can be used for the lens 149. Titanium oxide, zirconium oxide, or the like can be used for the nanoparticles.

In addition, cerium oxide, hafnium oxide, lanthanum oxide, magnesium oxide, niobium oxide, tantalum oxide, titanium oxide, yttrium oxide, zinc oxide, an oxide containing indium and tin, an oxide containing indium, gallium, and zinc, and the like can be used for the lens 149. Alternatively, zinc sulfide or the like can be used for the lens 149.

In the display device 100B, the protective layer 195 and the substrate 152 are bonded to each other with the adhesive layer 142. The adhesive layer 142 is provided to overlap with the light-receiving element 110 and the light-emitting element 190; that is, the display device 100B employs a solid sealing structure.

Structure Example 4-3

Figure 11A:
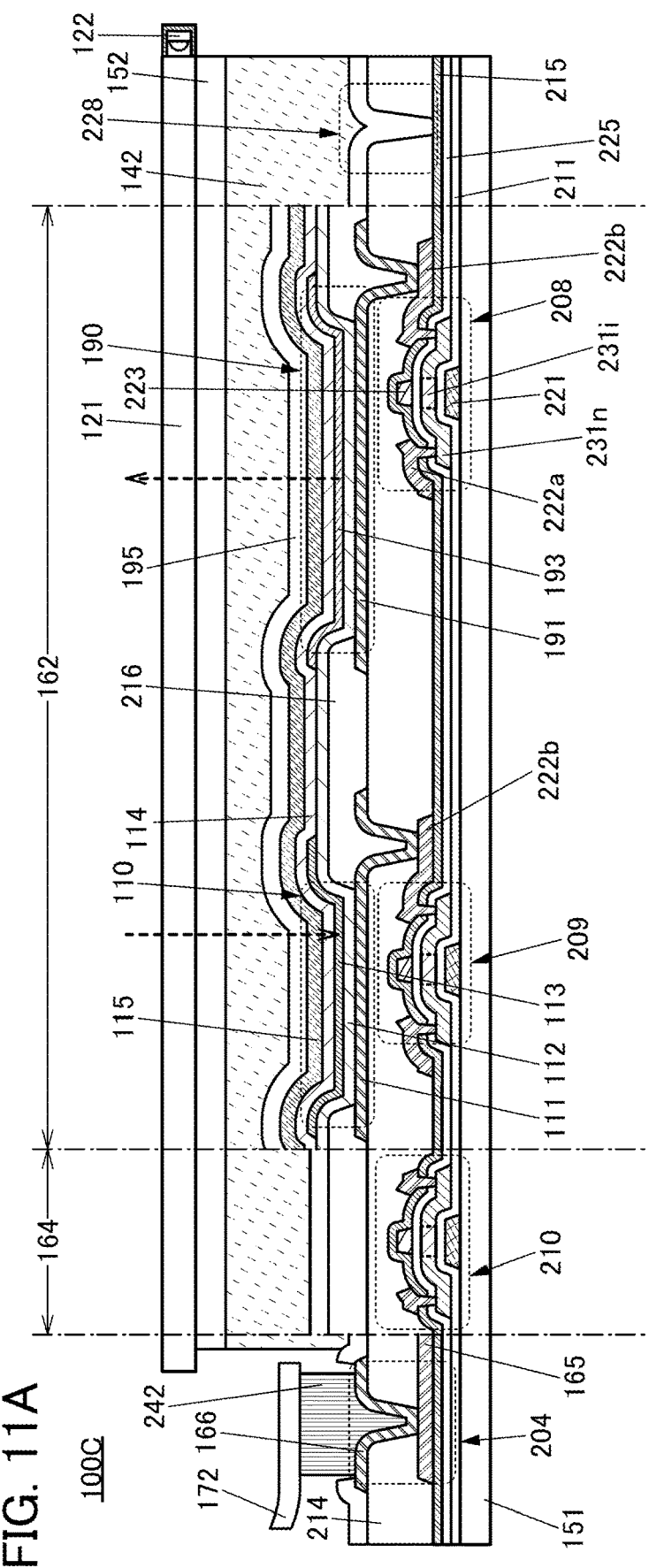
FIG. 11A and FIG. 11B are diagrams illustrating structure examples of a display device.

FIG. 11A illustrates a cross-sectional view of a display device 100C. The display device 100C is different from the display device 100B mainly in the structure of the transistors and including neither the light-blocking layer BM nor the lens 149.

The display device 100C includes a transistor 208, a transistor 209, and a transistor 210 over the substrate 151.

Each of the transistor 208, the transistor 209, and the transistor 210 includes the conductive layer 221 functioning as a gate, the insulating layer 211 functioning as a gate insulating layer, a semiconductor layer including a channel formation region 231$i$ and a pair of low-resistance regions 231$n$, the conductive layer 222$a$ connected to one of the pair of low-resistance regions 231$n$, the conductive layer 222$b$ connected to the other of the pair of low-resistance regions 231$n$, an insulating layer 225 functioning as a gate insulating layer, the conductive layer 223 functioning as a gate, and the insulating layer 215 covering the conductive layer 223. The insulating layer 211 is positioned between the conductive layer 221 and the channel formation region 231$i$. The insulating layer 225 is positioned between the conductive layer 223 and the channel formation region 231$i$.

The conductive layer 222$a$ and the conductive layer 222$b$ are connected to the corresponding low-resistance regions 231$n$ through openings provided in the insulating layer 225 and the insulating layer 215. One of the conductive layer 222$a$ and the conductive layer 222$b$ serves as a source, and the other serves as a drain.

The pixel electrode 191 of the light-emitting element 190 is electrically connected to the other of the pair of low-resistance regions 231$n$ of the transistor 208 through the conductive layer 222$b$.

The pixel electrode 111 of the light-receiving element 110 is electrically connected to the other of the pair of low-resistance regions 231$n$ of the transistor 209 through the conductive layer 222$b$.

Figure 11B:
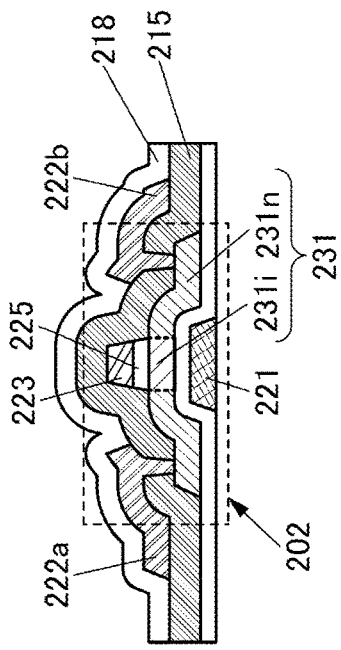

FIG. 11A illustrates an example in which the insulating layer 225 covers a top surface and a side surface of the semiconductor layer. Meanwhile, FIG. 11B illustrates an example of a transistor 202 in which the insulating layer 225 overlaps with the channel formation region 231$i$ of the semiconductor layer 231 and does not overlap with the low-resistance regions 231$n$. The structure shown in FIG. 11B can be manufactured by processing the insulating layer 225 using the conductive layer 223 as a mask, for example. In FIG. 11B, the insulating layer 215 is provided to cover the insulating layer 225 and the conductive layer 223, and the conductive layer 222$a$ and the conductive layer 222$b$ are connected to the low-resistance regions 231$n$ through the openings in the insulating layer 215. Furthermore, an insulating layer 218 covering the transistor may be provided.

Structure Example 4-4

Figure 12:
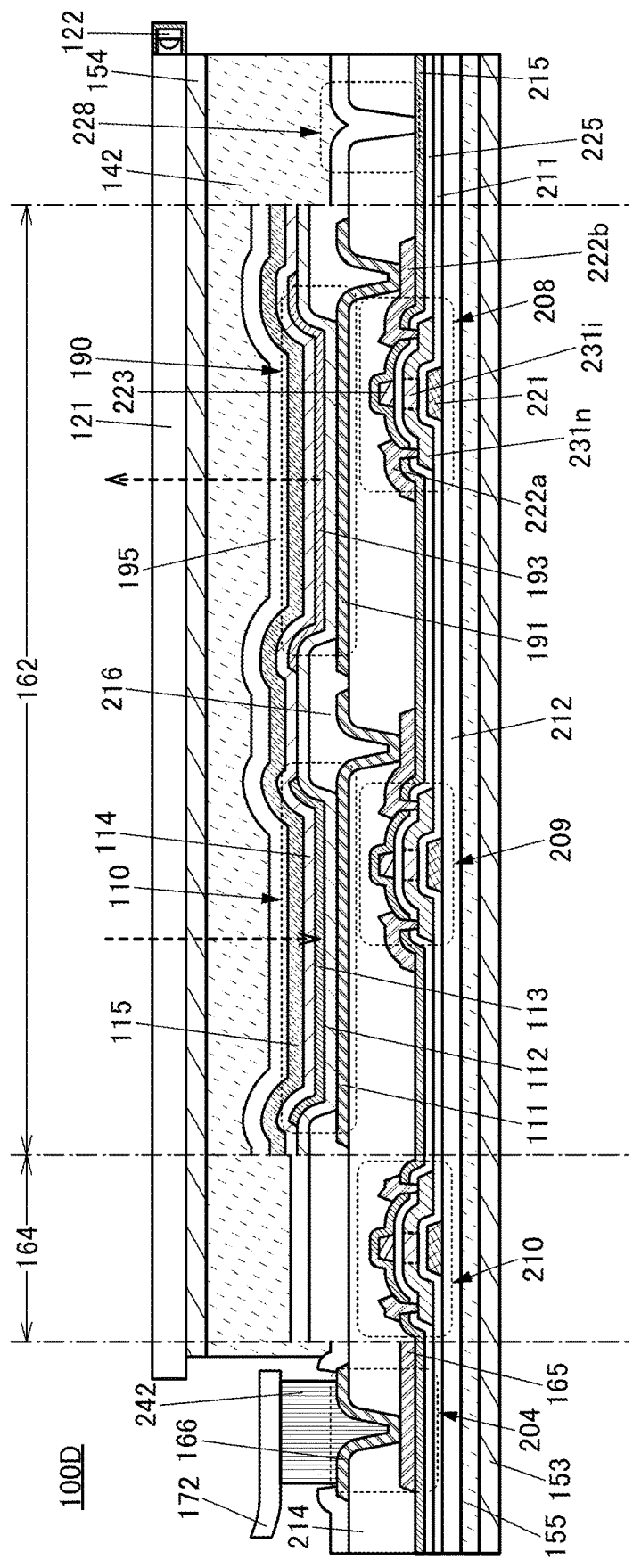
FIG. 12 is a diagram illustrating a structure example of a display device.

FIG. 12 illustrates a cross-sectional view of a display device 100D. The display device 100D is different from the display device 100C mainly in the structure of the substrates.

The display device 100D does not include the substrate 151 and the substrate 152 and includes the substrate 153, the substrate 154, the adhesive layer 155, and the insulating layer 212.

The substrate 153 and the insulating layer 212 are bonded to each other with the adhesive layer 155. The substrate 154 and the protective layer 195 are bonded to each other with the adhesive layer 142.

The display device 100D has a structure obtained in such a manner that the insulating layer 212, the transistor 208, the transistor 209, the light-receiving element 110, the light-emitting element 190, and the like are formed over a formation substrate and then transferred onto the substrate 153. The substrate 153 and the substrate 154 preferably have flexibility. Accordingly, the flexibility of the display device 100D can be increased.

The inorganic insulating film that can be used as the insulating layer 211, the insulating layer 213, and the insulating layer 215 can be used as the insulating layer 212. Alternatively, a stacked-layer film of an organic insulating film and an inorganic insulating film may be used as the insulating layer 212. In that case, a film on the transistor 209 side is preferably an inorganic insulating film.

The above is the description of the structure examples of the display device.

The display device of this embodiment includes a light-receiving element and a light-emitting element in a display portion, and the display portion has both a function of displaying an image and a function of sensing light. Thus, the size and weight of an electronic device can be reduced as compared to the case where a sensor is provided outside a display portion or outside a display device. Moreover, an electronic device having more functions can be achieved by a combination of the display device of this embodiment and a sensor provided outside the display portion or outside the display device.

In the light-receiving element, at least one of the layers other than the active layer can have a structure in common with a layer in the light-emitting element (EL element). Also in the light-receiving element, all of the layers other than the active layer can have structures in common with the layers in the light-emitting element (EL element). For example, the light-emitting element and the light-receiving element can be formed over one substrate only by adding a step of depositing the active layer in the manufacturing process of the light-emitting element. In the light-receiving element and the light-emitting element, their pixel electrodes can be formed using the same material in the same step, and their common electrodes can be formed using the same material in the same step. When a circuit electrically connected to the light-receiving element and a circuit electrically connected to the light-emitting element are formed using the same materials in the same steps, the manufacturing process of the display device can be simplified. In such a manner, a display device that incorporates a light-receiving element and is highly convenient can be manufactured without complicated steps.

Structure Example of Electronic Device

The display device of one embodiment of the present invention can obtain a variety of biological data with the use of infrared light and visible light. Such biological data can be used for both user's personal authentication uses and health care uses.

Typical examples of biological data that can be obtained using the display device of one embodiment of the present invention and can be used for personal authentication include data on a fingerprint, a palm print, a vein, an iris, and the like. Such biological data can be obtained using infrared light or visible light. It is particularly preferable that data on a vein and an iris be obtained using infrared light.

Examples of biological data that can be obtained using the display device of one embodiment of the present invention and can be used for health care uses include data on a pulse wave, a blood sugar level, oxygen saturation, a neutral fat concentration, and the like.

Furthermore, a unit for obtaining another biological data is preferably provided in an electronic device including the display device. Examples of such biological data include internal biological data on an electrocardiogram, blood pressure, a body temperature, and the like and superficial biological data on facial expression, complexion, a pupil, and the like. In addition, data on the number of steps taken, exercise intensity, a height difference in a movement, and a meal (e.g., calorie intake and nutrients) are important for health care. The use of a plurality of kinds of biological data and the like enables complex management of physical conditions, leading to not only daily health management but also early detection of injuries and diseases.

Blood pressure can be calculated from an electrocardiogram and a difference in timing of two pulsations of a pulse wave (a period of pulse wave propagation time), for example. High blood pressure results in a short pulse wave propagation time, whereas low blood pressure results in a long pulse wave propagation time. The body conditions of a user can be estimated from a relationship between the heart rate and blood pressure that is calculated from an electrocardiogram and a pulse wave. For example, when both the heart rate and blood pressure are high, the user can be estimated to be nervous or excited, whereas when both the heart rate and blood pressure are low, the user can be estimated to be relaxed. When the state where blood pressure is low and the heart rate is high is continued, the user might suffer from a heart disease or the like.

The user can check the biological data measured with the electronic device, one's own body conditions estimated on the basis of the data, and the like at any time; thus, health awareness is improved. This may inspire the user to reconsider the daily habits, for example, to avoid over-eating and over-drinking, get enough exercise, and manage one's physical conditions, and to have a medical examination at a medical institution as necessary.

Structure Example 1

Figure 13:
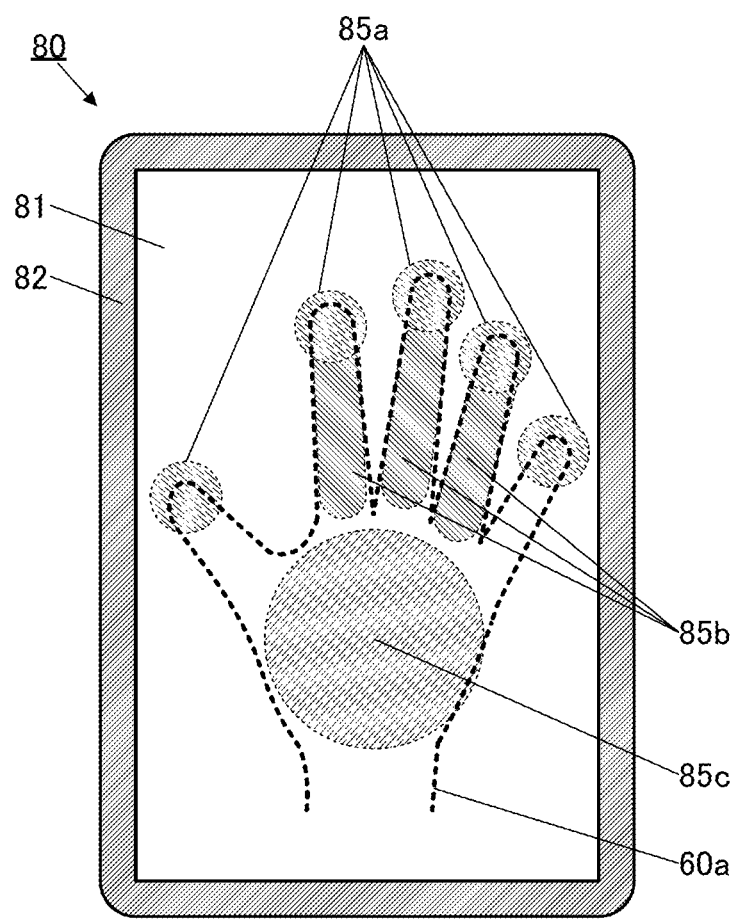
FIG. 13 is a diagram illustrating a structure example of an electronic device.

FIG. 13 is a schematic view of an electronic device 80. The electronic device 80 can be used as a tablet terminal. The electronic device 80 includes at least a housing 82 and a display portion 81. The display portion 81 includes the display device of one embodiment of the present invention.

When a hand 60a of a user is held over or touches the display portion 81, the electronic device 80 can execute personal authentication and obtain biological data of the user.

When the hand 60a of the user is put on the display portion 81, the electronic device 80 can recognize the shape. Then, biological data suitable for regions corresponding to the respective parts of the hand 60a is obtained. For example, in regions 85a corresponding to fingertips of the hand 60a, image capturing of the shapes of fingerprints and veins can be executed. In addition, in regions 85b corresponding to balls of fingers, image capturing of the shapes of veins and arterioles can be executed, for example. Moreover, in a region 85c corresponding to a palm, image capturing of a palm print, a vein, an arteriole, and a dermis can be executed, for example. The images of the fingerprints, the palm print, and the veins can be used for personal authentication. Biological data can be obtained from the images of the arterioles, the veins, and the dermis.

When biological data is to be obtained, an image imitating the shape of a hand may be displayed on the display portion 81 to urge the user to put the hand 60a on the image. This can improve the recognition accuracy of the shape of the hand 60a.

In this manner, the biological data of the user can be obtained every time personal authentication for starting up the electronic device 80 is executed. Thus, the biological data can be accumulated continuously with the user being unconscious, which enables continuous health management to be performed. The above is preferable because the user need not execute application software or the like for health management each time, and obtainment and update of the biological data are not stopped.

Structure Example 2

Figure 14A:
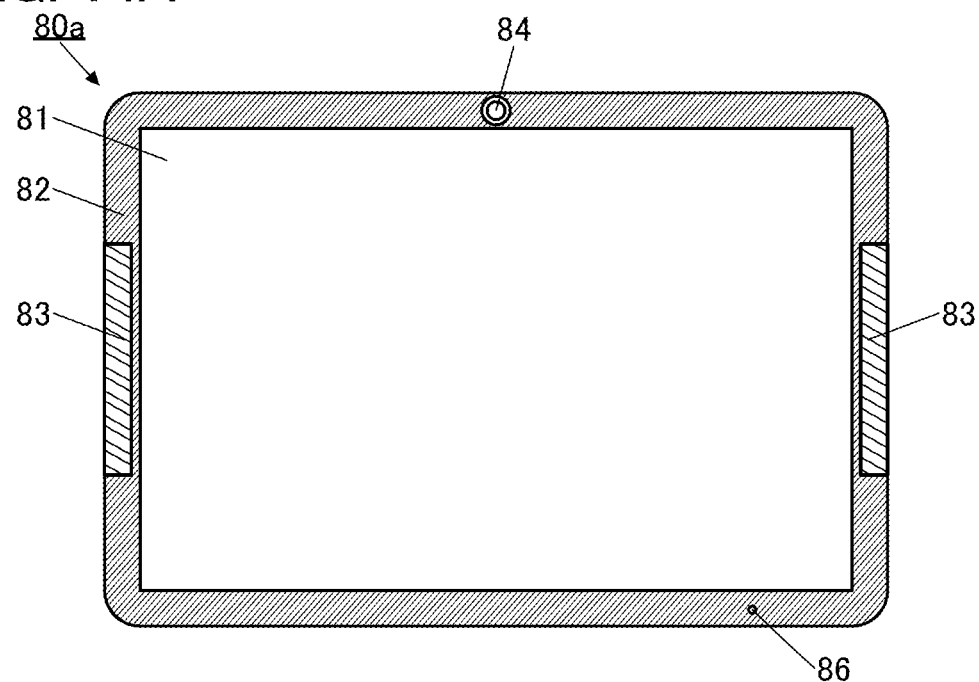
FIG. 14A and FIG. 14B are diagrams illustrating a structure example of an electronic device.

FIG. 14A is a schematic view of an electronic device 80a. The electronic device 80a includes a pair of electrodes 83, a camera 84, and a microphone 86 in addition to the components of the electronic device 80.

The pair of electrodes 83 is provided in parts of the housing 82 with the display portion 81 therebetween. The electrodes 83 function as electrodes for obtaining an electrocardiogram. When the user holds the pair of electrodes 83 with both hands, an electrocardiogram can be measured. Providing the pair of electrodes 83 in the longitudinal direction of the housing 82 as illustrated in FIG. 14A enables an electrocardiogram to be obtained with the user being unconscious when the user uses the electronic device 80a with a landscape screen.

The camera 84 can capture an image of a user's face, for example. Biological data on facial expression, a pupil, an iris, complexion, and the like can be obtained from the image of the user's face.

The microphone 86 can obtain a user's voice. Voiceprint data that can be used for voiceprint authentication can be obtained from the obtained voice data. When voice data is regularly obtained and a change in voice quality is monitored, the voice data can be utilized for health management.

Figure 14B:
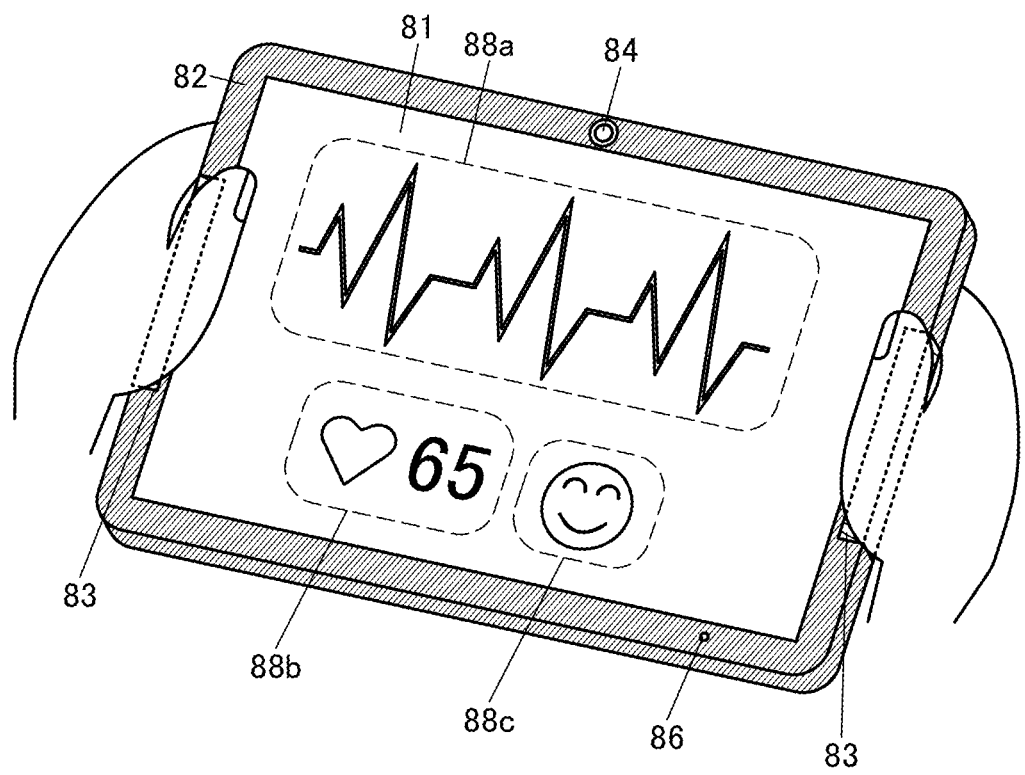

FIG. 14B illustrates an example of a usage state of the electronic device 80a. The display portion 81 displays data 88a on an electrocardiogram obtained by the pair of electrodes 83, data 88b on the heart rate, a character image 88c showing data on the user's health conditions estimated from a variety of biological data, and the like.

Structure Example 3

Figure 15A:
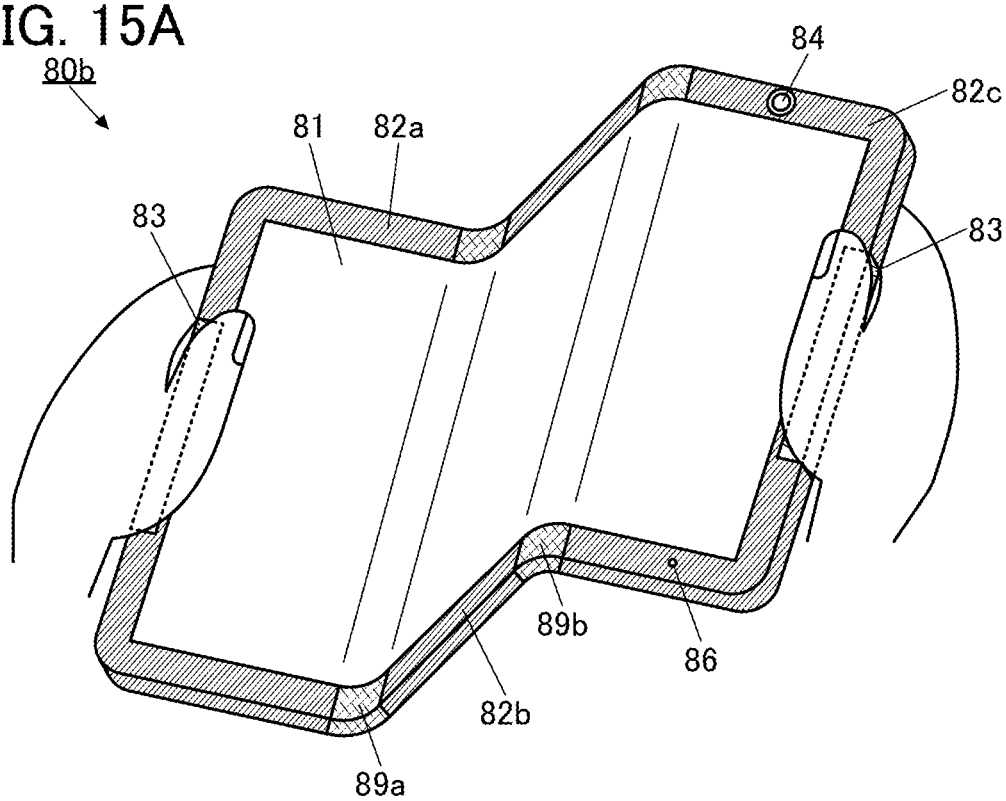
FIG. 15A and FIG. 15B are diagrams each illustrating a structure example of an electronic device.

FIG. 15A illustrates an electronic device 80b in which the display portion 81 can be folded in three. In the electronic device 80b, the display portion 81 is provided across a housing 82a, a housing 82b, and a housing 82c. A flexible display device is used for the display portion 81.

The housing 82a and the housing 82b are connected to each other with a joint portion 89a. The housing 82b and the housing 82c are connected to each other with a joint portion 89b. The electronic device 80b can be changed in shape between a state where the display portion 81 is opened and a state where the display portion 81 is folded in three.

As illustrated in FIG. 15A, the pair of electrodes 83 is provided in positions touched by the user's hands when the shape of the electronic device 80b is changed. This enables biological data (e.g., an electrocardiogram) to be obtained with the user being unconscious when the electronic device 80b is opened or closed.

Figure 15B:
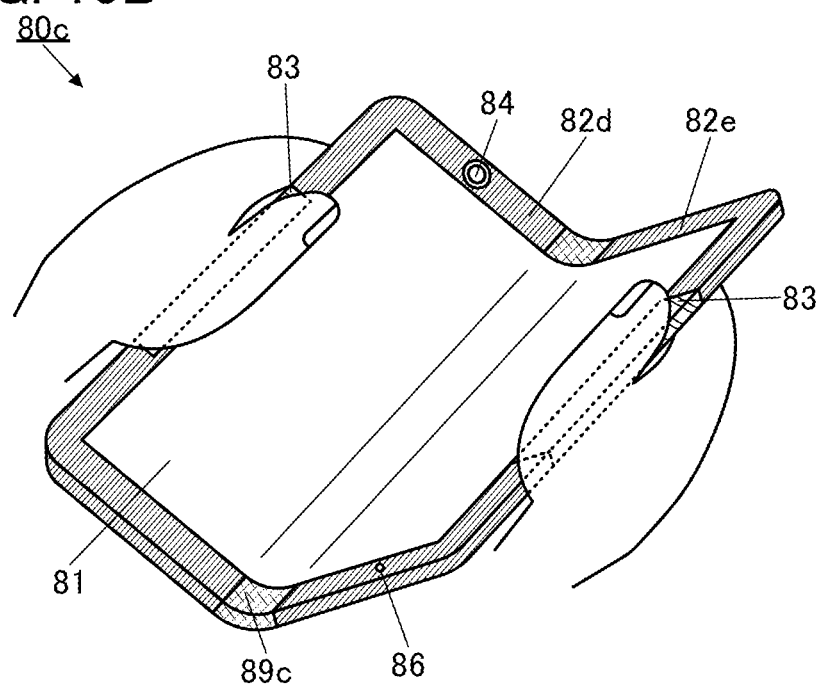

FIG. 15B illustrates an electronic device 80c in which the display portion 81 can be folded in half In the electronic device 80c, the display portion 81 is provided across a housing 82d and a housing 82e connected to each other with a joint portion 89c.

Although an example is shown here in which the electronic device 80c is folded such that the display portion 81 is on the inside, a structure may be employed in which the electronic device 80c is folded such that the display portion 81 is on the outside.

Figure 16A:
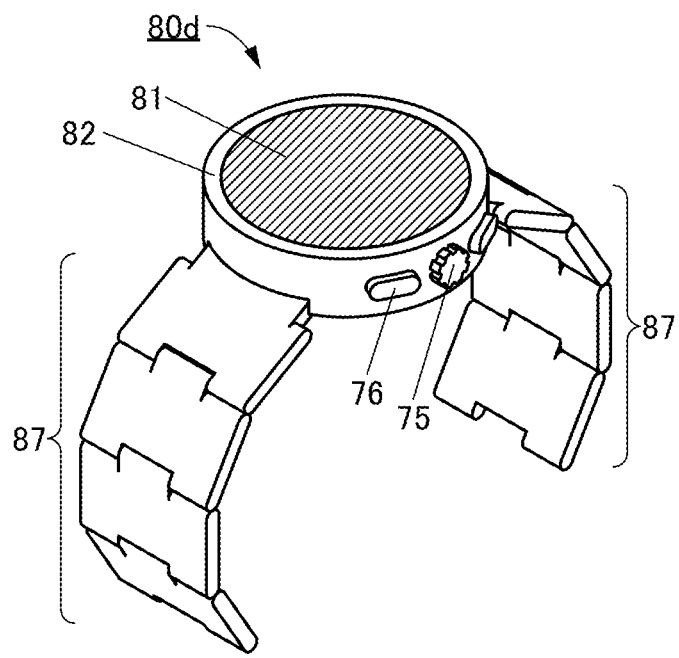
FIG. 16A and FIG. 16B are diagrams illustrating a structure example of an electronic device.
Figure 16B:
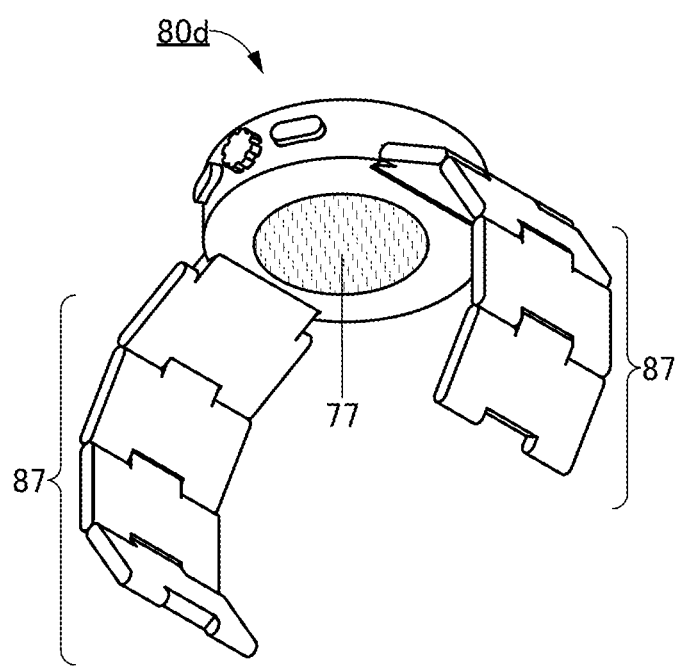

FIG. 16A and FIG. 16B illustrate a watch-type electronic device 80d. The electronic device 80d includes the display portion 81, the housing 82, a pair of bands 87, a sensor 77, a bezel 75, a button 76, and the like.

The above display device can be used for the display portion 81. Fingerprint authentication or the like can be performed by a touch of the fingertip on the display portion 81. In addition, the display portion 81 can function as a touch panel as well.

The sensor 77 is provided on the side opposite to the side provided with the display portion 81 of the housing 82, and is positioned in a portion in contact with the arm. As the sensor 77, a contact-type sensor, an optical sensor, or the like can be used. With the contact-type sensor, biological data on pulsation, a body temperature, and the like can be obtained. The optical sensor can use infrared light or visible light to obtain biological data from a blood vessel, a dermis, or the like.

A variety of sensors such as an acceleration sensor, a magnetic sensor, and a UV sensor may be provided inside the housing 82. These sensors can obtain data on the user's posture, the user's activity history, and the environment.

Structure Example of System

According to one embodiment of the present invention, a variety of biological data can be obtained regularly and continuously, and such biological data can be utilized for personal authentication or health management.

Examples of biological data that can be obtained using visible light and infrared light include data on a fingerprint, a palm print, a shape of a vein, a pulse wave, a respiration rate, a pulse, oxygen saturation, a blood sugar level, a neutral fat concentration, and the like. Other examples include data on facial expression, complexion, a pupil, a voiceprint, and the like. It is preferable to use such a variety of biological data to comprehensively determine the health conditions of the user.

Whether a plurality of pieces of measured biological data each have normal values or abnormal values is determined, and on the basis of a plurality of determination results, the health conditions of the user can be determined. Alternatively, the conditions of the user may be determined from the plurality of pieces of measured biological data (e.g., it is determined that the value of a pulse is high, low, or normal), and on the basis of a plurality of determination results, the health conditions of the user may be determined. These methods have a clear basis for the obtained determination results and thus have an advantage that an improvement plan can be easily presented to the user.

Feature values may be extracted from all the pieces of measured biological data, and the health conditions of the user may be determined from the feature values. This method facilitates determination based on not only individual pieces of biological data but also the correlation between the plurality of pieces of biological data, increasing the sensing accuracy.

As a classifier or an identifier for determining the health conditions of the user from a variety of biological data, a machine learning model that has learned by machine learning is preferably used. The machine learning is roughly classified into supervised machine learning, unsupervised machine learning, outlier detection, and the like.

Examples of the supervised machine learning include k-nearest neighbor, a Naive Bayes classifier, a decision tree, a support vector machine (SVM), a random forest, and a neural network. The neural network is especially suitable for a method for extracting feature values from a plurality of pieces of data because learning during the extraction of feature values is possible in the neural network. The supervised machine learning requires labeled data. In that case, a learning model that has learned in advance using labeled teacher data may be used, or data on the physical conditions, the health conditions, or the like input by the user may be used as a label for learning at the time of obtaining biological data and a learning model may be updated at any time. Alternatively, the health conditions of the user may be estimated from data on facial expression, a voiceprint, activity intensity, and the like, the data may be used as a label for learning, and a learning model may be updated at any time.

Examples of an extraction method of feature values used in the unsupervised machine learning include principal component analysis (PCA) and non-negative matrix factorization (NMF). Examples of the classifier include k-means clustering and DBSCAN (Density-Based Spatial Clustering of Applications with Noise).

A combination of a supervised machine learning model and an unsupervised machine learning model may be used for determination of the obtained plurality of pieces of biological data. In that case, as classification labels classified by the unsupervised machine learning model, labels used in another supervised machine learning model may be used.

In the outlier detection, whether the obtained biological data or feature values obtained from one or more pieces of biological data deviate from the normal area is detected. When the outlier is detected, it is highly probable that the health conditions of the user deviate from the normal conditions.

Examples of a model for detecting the outlier include k-nearest neighbor, LOF (Local Outlier Factor), One class SVM, and Mahalanobis' Distance. The use of multidimensional data combining data for the outlier detection is effective. The above is particularly effective when a strong correlation is established between the state of the user (e.g., the user is standing, sitting, or moving) at the time of obtaining biological data and the obtained biological data, for example. The outlier detection executed on the basis of a plurality of pieces of data enables determination taking the state of the user into account; thus, a detection error can be prevented. In the case where biological data is data that changes over time depending on the state of the user (e.g., a pulse or a respiration rate) or the like, a neighbor method using a sliding window, a dynamic time warping (DTW) method, a singular spectrum transformation method, or the like may be used. In the case of periodically changing biological data, deviation from a prediction model may be detected using LSTM (Long Short Term Memory) or the like.

A structure example of a system of one embodiment of the present invention and an operation example of the system will be described below with reference to drawings.

Figure 17:
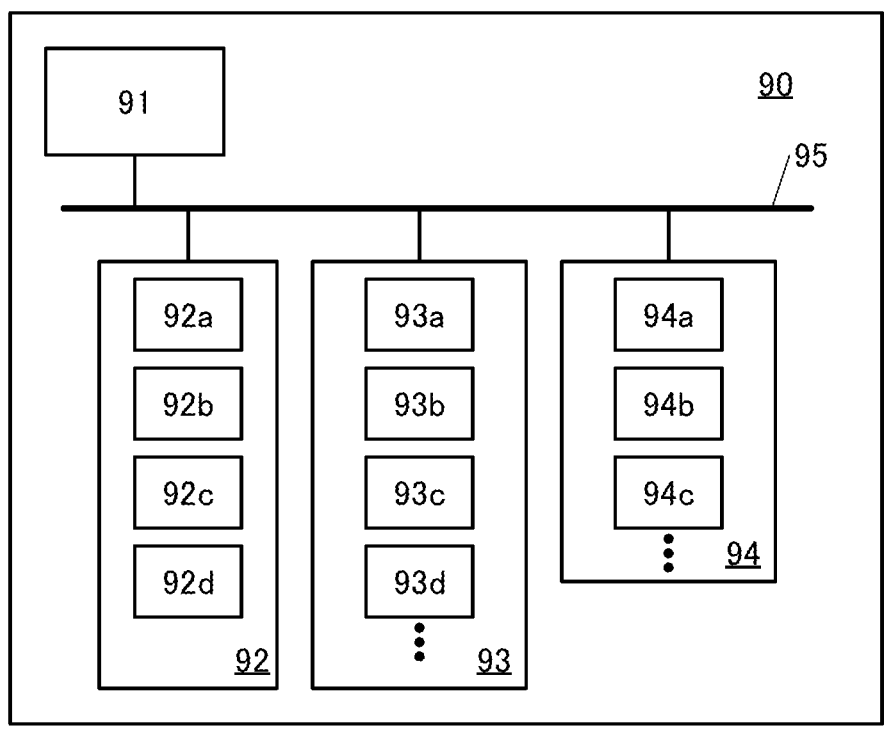
FIG. 17 is a diagram illustrating a structure example of a system.

FIG. 17 is a block diagram of a system 90 including the display device of one embodiment of the present invention. The system 90 includes an arithmetic portion 91, a memory portion 92, an input portion 93, an output portion 94, a bus line 95, and the like. The system 90 can be used for a variety of electronic devices including a display portion, such as the above-described electronic device 80.

The arithmetic portion 91 is connected to the memory portion 92, the input portion 93, the output portion 94, and the like through the bus line 95 and has a function of controlling these portions collectively.

The memory portion 92 has a function of storing data, a program, and the like. Here, the memory portion 92 stores a learning model 92a for fingerprint authentication, a learning model 92b for vein authentication, a learning model 92c for anomaly detection, local data 92d including biological data of the user obtained before or anomaly data stored before, and the like.

The input portion 93 has a function of obtaining a variety of biological data. A variety of sensor devices can be used as the input portion 93. Here, an example is shown in which the input portion 93 includes a photosensor 93a, a camera 93b, a microphone 93c, an electrocardiogram monitor 93d, and the like. The sensor including the light-receiving element in the above-described display device can be used as the photosensor 93a. The electrocardiogram monitor 93d includes, for example, a pair of electrodes for measuring an electrocardiogram and a measuring device that measures voltage between the electrodes, the value of current flowing between the electrodes, and the like.

The output portion 94 has a function of providing the user with data. Here, an example is shown in which the output portion 94 includes a display 94a, a speaker 94b, a vibration device 94c, and the like. The output portion 94 can be used to raise an alert to the user when it is determined that the health conditions are abnormal, for example.

The display device of one embodiment of the present invention includes the light-receiving element functioning as a photosensor and the light-emitting element in the display portion and thus can double as the photosensor 93a in the input portion 93 and the display 94a in the output portion 94 illustrated in FIG. 17. That is, the system 90 can be obtained with a structure including the display device, the arithmetic portion 91, and the memory portion 92.

The display device has a function of obtaining biological data on a fingerprint, a vein, or the like of the user, and the arithmetic portion 91 can execute fingerprint authentication or vein authentication on the basis of the learning model 92a or the learning model 92b stored in the memory portion 92 and the biological data.

In addition, the display device has a function of obtaining other pieces of biological data of the user (e.g., oxygen saturation, a blood sugar level, and a neutral fat concentration), and the arithmetic portion 91 can execute anomaly detection on the basis of the learning model 92c stored in the memory portion 92 and the biological data.

Figure 18:
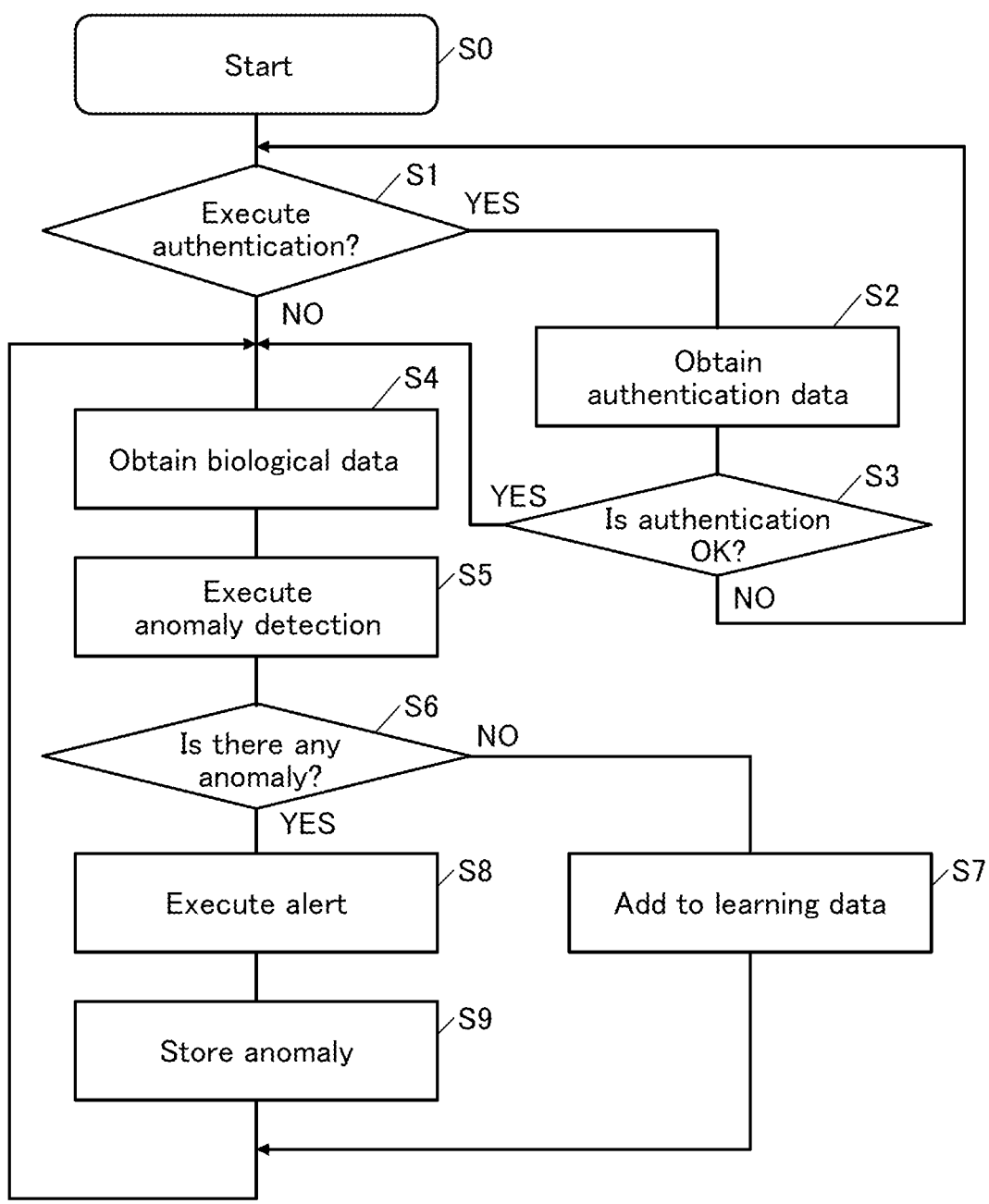
FIG. 18 is a flow chart showing an operation method of a system.

An operation method example of the system of one embodiment of the present invention will be described below. FIG. 18 is a flow chart of an operation method of the system. The flow chart shown in FIG. 18 includes Step S0 to Step S9.

Operation starts in Step S0. The operation starts when power-on of an electronic device, a touch on a display portion, a change in the orientation of the electronic device, or the like is sensed, for example.

In Step S1, the determination whether authentication is needed is performed. In the case where the authentication has already been executed and the system is in the log-in state, it is determined that the authentication is unnecessary and the operation goes to Step S4. On the other hand, in the case where the system is in the log-off state, it is determined that the authentication is necessary and the operation goes to Step S2.

In Step S2, authentication data is obtained. For example, an image of a fingerprint, a palm print, a vein, or the like of the user is captured, and biological data is obtained from the captured image.

In Step S3, whether the authentication is performed correctly is determined. For example, the data on the fingerprint, the palm print, or the vein is compared with the user's data registered in advance, and whether they match each other is determined. The determination may be performed using a machine learning model such as the learning model 92a or the learning model 92b. Alternatively, an authentication method not using a machine learning model, such as a pattern matching method, may be employed. In the case where the authentication is performed correctly, logging in to the system is performed and then the operation goes to Step S4. In the case where the authentication is not performed correctly, the log-off state of the system is kept and the operation returns to Step S1.

In Step S4, biological data used for the determination of the health conditions is obtained. The biological data can be obtained with the components of the input portion 93. As the biological data to be obtained, for example, data on one or more of a fingerprint, a palm print, the shape of a vein, a pulse wave, a respiration rate, oxygen saturation, a blood sugar level, a neutral fat concentration, facial expression, complexion, a pupil, a voiceprint, a body temperature, and the like is preferably obtained.

In Step S5, anomaly detection is executed using the obtained biological data. The anomaly detection can be performed using the above-described learning model 92c for anomaly detection.

In Step S6, the determination whether the results of the anomaly detection are abnormal or not is performed. When it is determined that the results are not abnormal, the operation goes to Step S7. By contrast, when it is determined that the results are abnormal, the operation goes to Step S8.

In Step S7, the obtained biological data or the processed data thereof (e.g., a feature value) is labeled as not abnormal, and is added to the local data 92d stored in the memory portion 92 as learning data. This allows a learning model suitable for each user to be constructed, which can increase the anomaly detection accuracy.

In Step S8, the operation for alerting the user to the abnormal results is executed. For example, the operation for applying a stimulus to the sense of sight, the sense of hearing, the sense of touch, the sense of smell, or the like of the user is performed using the components of the output portion 94. Specifically, an image or text is displayed on the display 94a, the user is notified of the alert as voice data using the speaker 94b, and the electronic device is vibrated with the vibration device 94c, for example. Two or more of these operations are preferably executed at the same time, in which case the user's awareness is easily enhanced.

In Step S9, the obtained biological data or the processed data thereof is labeled as abnormal, and is added to the local data 92d stored in the memory portion 92.

After Step S9, the operation may go to Step S4 as shown in FIG. 18.

In this manner, the system of one embodiment of the present invention can execute the operation for managing the user's health and the authentication operation of the system in combination. This eliminates the necessity of executing application software or the like for health management by the user; thus, the health management can be performed at the time of starting up the electronic device or at the time of log-in operation with the user being unconscious, which enables regular and continuous health management.

The above is the description of the structure example and the operation example of the system of one embodiment of the present invention.

[Metal Oxide]

A metal oxide that can be used for the semiconductor layer will be described below.

Note that in this specification and the like, a metal oxide containing nitrogen is also collectively referred to as a metal oxide in some cases. A metal oxide containing nitrogen may be referred to as a metal oxynitride. For example, a metal oxide containing nitrogen, such as zinc oxynitride (ZnON), may be used for the semiconductor layer.

Note that in this specification and the like, CAAC (c-axis aligned crystal) or CAC (Cloud-Aligned Composite) may be stated. CAAC refers to an example of a crystal structure, and CAC refers to an example of a function or a material composition.

For example, a CAC (Cloud-Aligned Composite)-OS (Oxide Semiconductor) can be used for the semiconductor layer.

A CAC-OS or a CAC-metal oxide has a conducting function in part of the material and has an insulating function in another part of the material; as a whole, the CAC-OS or the CAC-metal oxide has a function of a semiconductor. In the case where the CAC-OS or the CAC-metal oxide is used in a semiconductor layer of a transistor, the conducting function is to allow electrons (or holes) serving as carriers to flow, and the insulating function is to not allow electrons serving as carriers to flow. By the complementary action of the conducting function and the insulating function, a switching function (On/Off function) can be given to the CAC-OS or the CAC-metal oxide. In the CAC-OS or the CAC-metal oxide, separation of the functions can maximize each function.

Furthermore, the CAC-OS or the CAC-metal oxide includes conductive regions and insulating regions. The conductive regions have the above-described conducting function, and the insulating regions have the above-described insulating function. Furthermore, in some cases, the conductive regions and the insulating regions in the material are separated at the nanoparticle level. Furthermore, in some cases, the conductive regions and the insulating regions are unevenly distributed in the material. Furthermore, in some cases, the conductive regions are observed to be coupled in a cloud-like manner with their boundaries blurred.

Furthermore, in the CAC-OS or the CAC-metal oxide, the conductive regions and the insulating regions each have a size greater than or equal to 0.5 nm and less than or equal to 10 nm, preferably greater than or equal to 0.5 nm and less than or equal to 3 nm, and are dispersed in the material, in some cases.

Furthermore, the CAC-OS or the CAC-metal oxide includes components having different band gaps. For example, the CAC-OS or the CAC-metal oxide includes a component having a wide gap due to the insulating region and a component having a narrow gap due to the conductive region. In the case of the structure, when carriers flow, carriers mainly flow in the component having a narrow gap. Furthermore, the component having a narrow gap complements the component having a wide gap, and carriers also flow in the component having a wide gap in conjunction with the component having a narrow gap. Therefore, in the case where the above-described CAC-OS or CAC-metal oxide is used in a channel formation region of a transistor, high current driving capability in an on state of the transistor, that is, a high on-state current and high field-effect mobility can be obtained.

In other words, the CAC-OS or the CAC-metal oxide can also be referred to as a matrix composite or a metal matrix composite.

Oxide semiconductors (metal oxides) are classified into a single crystal oxide semiconductor and a non-single-crystal oxide semiconductor. Examples of a non-single-crystal oxide semiconductor include a CAAC-OS (c-axis aligned crystalline oxide semiconductor), a polycrystalline oxide semiconductor, an nc-OS (nanocrystalline oxide semiconductor), an amorphous-like oxide semiconductor (a-like OS), and an amorphous oxide semiconductor.

The CAAC-OS has c-axis alignment, a plurality of nanocrystals are connected in the a-b plane direction, and its crystal structure has distortion. Note that the distortion refers to a portion where the direction of a lattice arrangement changes between a region with a regular lattice arrangement and another region with a regular lattice arrangement in a region where the plurality of nanocrystals are connected.

The nanocrystal is basically a hexagon but is not always a regular hexagon and is a non-regular hexagon in some cases. Furthermore, a pentagonal or heptagonal lattice arrangement, for example, is included in the distortion in some cases. Note that it is difficult to observe a clear crystal grain boundary (also referred to as grain boundary) even in the vicinity of distortion in the CAAC-OS. That is, formation of a crystal grain boundary is found to be inhibited by the distortion of a lattice arrangement. This is because the CAAC-OS can tolerate distortion owing to a low density of arrangement of oxygen atoms in the a-b plane direction, an interatomic bond length changed by substitution of a metal element, and the like.

The CAAC-OS tends to have a layered crystal structure (also referred to as a layered structure) in which a layer containing indium and oxygen (hereinafter, In layer) and a layer containing an element M, zinc, and oxygen (hereinafter, (M,Zn) layer) are stacked. Note that indium and the element M can be replaced with each other, and when the element M in the (M,Zn) layer is replaced with indium, the layer can also be referred to as an (In,M,Zn) layer. Furthermore, when indium in the In layer is replaced with the element M, the layer can be referred to as an (In,M) layer.

The CAAC-OS is a metal oxide with high crystallinity. On the other hand, a clear crystal grain boundary is difficult to observe in the CAAC-OS; thus, it can be said that a reduction in electron mobility due to the crystal grain boundary is unlikely to occur. Entry of impurities, formation of defects, or the like might decrease the crystallinity of a metal oxide; thus, it can be said that the CAAC-OS is a metal oxide that has small amounts of impurities and defects (e.g., oxygen vacancies (also referred to as $V_O$)). Thus, a metal oxide including a CAAC-OS is physically stable. Therefore, the metal oxide including a CAAC-OS is resistant to heat and has high reliability.

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods.

Note that indium-gallium-zinc oxide (hereinafter, IGZO), which is a kind of metal oxide containing indium, gallium, and zinc, has a stable structure in some cases by being formed of the above-described nanocrystals. In particular, crystals of IGZO tend not to grow in the air and thus, a stable structure might be obtained when IGZO is formed of smaller crystals (e.g., the above-described nanocrystals) rather than larger crystals (here, crystals with a size of several millimeters or several centimeters).

An a-like OS is a metal oxide having a structure between those of the nc-OS and an amorphous oxide semiconductor. The a-like OS includes a void or a low-density region. That is, the a-like OS has low crystallinity as compared with the nc-OS and the CAAC-OS.

An oxide semiconductor (metal oxide) can have various structures that show different properties. Two or more of the amorphous oxide semiconductor, the polycrystalline oxide semiconductor, the a-like OS, the nc-OS, and the CAAC-OS may be included in an oxide semiconductor of one embodiment of the present invention.

A metal oxide film that functions as a semiconductor layer can be deposited using either or both of an inert gas and an oxygen gas. Note that there is no particular limitation on the flow rate ratio of oxygen (the partial pressure of oxygen) at the time of depositing the metal oxide film. However, to obtain a transistor having high field-effect mobility, the flow rate ratio of oxygen (the partial pressure of oxygen) at the time of depositing the metal oxide film is preferably higher than or equal to 0% and lower than or equal to 30%, further preferably higher than or equal to 5% and lower than or equal to 30%, still further preferably higher than or equal to 7% and lower than or equal to 15%.

The energy gap of the metal oxide is preferably 2 eV or more, further preferably 2.5 eV or more, still further preferably 3 eV or more. With use of a metal oxide having such a wide energy gap, the off-state current of the transistor can be reduced.

The substrate temperature during the deposition of the metal oxide film is preferably lower than or equal to 350° C., further preferably higher than or equal to room temperature and lower than or equal to 200° C., still further preferably higher than or equal to room temperature and lower than or equal to 130° C. The substrate temperature during the deposition of the metal oxide film is preferably room temperature because productivity can be increased.

The metal oxide film can be formed by a sputtering method. Alternatively, a PLD method, a PECVD method, a thermal CVD method, an ALD method, or a vacuum evaporation method, for example, may be used.

The above is the description of the metal oxide.

At least part of this embodiment can be implemented in combination with the other embodiments described in this specification as appropriate.

Embodiment 2

In this embodiment, a display device of one embodiment of the present invention will be described with reference to FIG. 19.

A display device of one embodiment of the present invention includes first pixel circuits each including a light-receiving element and second pixel circuits each including a light-emitting element. The first pixel circuits and the second pixel circuits are arranged in a matrix.

Figure 19A:
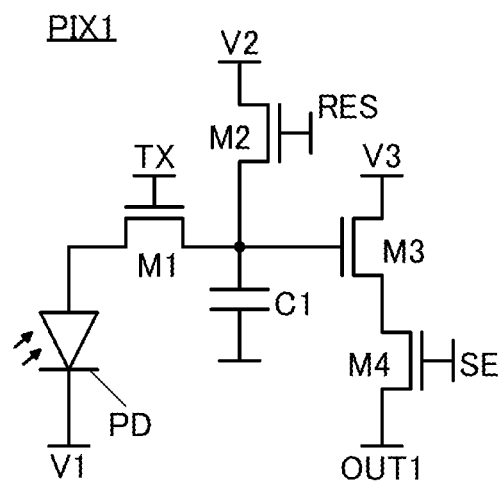
FIG. 19A and FIG. 19B are diagrams illustrating structure examples of pixel circuits.
Figure 19B:
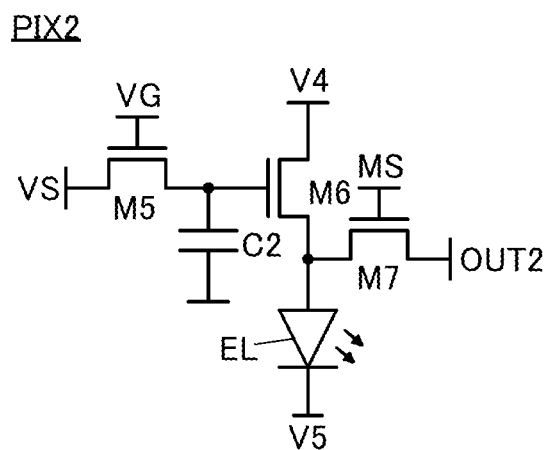

FIG. 19A illustrates an example of the first pixel circuit including a light-receiving element, and FIG. 19B illustrates an example of the second pixel circuit including a light-emitting element.

A pixel circuit PIX1 illustrated in FIG. 19A includes a light-receiving element PD, a transistor M1, a transistor M2, a transistor M3, a transistor M4, and a capacitor C1. Here, an example in which a photodiode is used as the light-receiving element PD is illustrated.

A cathode of the light-receiving element PD is electrically connected to a wiring V1, and an anode thereof is electrically connected to one of a source and a drain of the transistor M1. A gate of the transistor M1 is electrically connected to a wiring TX, and the other of the source and the drain thereof is electrically connected to one electrode of the capacitor C1, one of a source and a drain of the transistor M2, and a gate of the transistor M3. A gate of the transistor M2 is electrically connected to a wiring RES, and the other of the source and the drain thereof is electrically connected to a wiring V2. One of a source and a drain of the transistor M3 is electrically connected to a wiring V3, and the other of the source and the drain thereof is electrically connected to one of a source and a drain of the transistor M4. A gate of the transistor M4 is electrically connected to a wiring SE, and the other of the source and the drain thereof is electrically connected to a wiring OUT1.

A constant potential is supplied to the wiring V1, the wiring V2, and the wiring V3. When the light-receiving element PD is driven with a reverse bias, a potential lower than the potential of the wiring V1 is supplied to the wiring V2. The transistor M2 is controlled by a signal supplied to the wiring RES and has a function of resetting the potential of a node connected to the gate of the transistor M3 to a potential supplied to the wiring V2. The transistor M1 is controlled by a signal supplied to the wiring TX and has a function of controlling the timing at which the potential of the node changes, in accordance with a current flowing through the light-receiving element PD. The transistor M3 functions as an amplifier transistor for performing output in response to the potential of the node. The transistor M4 is controlled by a signal supplied to the wiring SE and functions as a selection transistor for reading an output corresponding to the potential of the node by an external circuit connected to the wiring OUT1.

A pixel circuit PIX2 illustrated in FIG. 19B includes a light-emitting element EL, a transistor M5, a transistor M6, a transistor M7, and a capacitor C2. Here, an example in which a light-emitting diode is used as the light-emitting element EL is illustrated. In particular, an organic EL element is preferably used as the light-emitting element EL.

A gate of the transistor M5 is electrically connected to a wiring VG, one of a source and a drain thereof is electrically connected to a wiring VS, and the other of the source and the drain thereof is electrically connected to one electrode of the capacitor C2 and a gate of the transistor M6. One of a source and a drain of the transistor M6 is electrically connected to a wiring V4, and the other thereof is electrically connected to an anode of the light-emitting element EL and one of a source and a drain of the transistor M7. A gate of the transistor M7 is electrically connected to a wiring MS, and the other of the source and the drain thereof is electrically connected to a wiring OUT2. A cathode of the light-emitting element EL is electrically connected to a wiring V5.

A constant potential is supplied to the wiring V4 and the wiring V5. In the light-emitting element EL, the anode side can have a high potential and the cathode side can have a lower potential than the anode side. The transistor M5 is controlled by a signal supplied to the wiring VG and functions as a selection transistor for controlling a selection state of the pixel circuit PIX2. The transistor M6 functions as a driving transistor that controls a current flowing through the light-emitting element EL, in accordance with a potential supplied to the gate. When the transistor M5 is in an on state, a potential supplied to the wiring VS is supplied to the gate of the transistor M6, and the emission luminance of the light-emitting element EL can be controlled in accordance with the potential. The transistor M7 is controlled by a signal supplied to the wiring MS and has a function of outputting a potential between the transistor M6 and the light-emitting element EL to the outside through the wiring OUT2.

Note that in the display device of this embodiment, the light-emitting element may be made to emit light in a pulsed manner so as to display an image. A reduction in the driving time of the light-emitting element can reduce the power consumption of the display device and suppress heat generation of the display device. An organic EL element is particularly preferable because of its favorable frequency characteristics. The frequency can be higher than or equal to 1 kHz and lower than or equal to 100 MHz, for example.

Here, a transistor using a metal oxide (an oxide semiconductor) in a semiconductor layer where a channel is formed is preferably used as the transistor M1, the transistor M2, the transistor M3, and the transistor M4 included in the pixel circuit PIX1 and the transistor M5, the transistor M6, and the transistor M7 included in the pixel circuit PIX2.

A transistor using a metal oxide having a wider band gap and a lower carrier density than silicon can achieve an extremely low off-state current. Thus, such a low off-state current enables retention of charge accumulated in a capacitor that is connected in series with the transistor for a long time. Therefore, it is particularly preferable to use a transistor using an oxide semiconductor as the transistor M1, the transistor M2, and the transistor M5 each of which is connected in series with the capacitor C1 or the capacitor C2. Moreover, the use of transistors using an oxide semiconductor as the other transistors can reduce the manufacturing cost.

Alternatively, transistors using silicon as a semiconductor where a channel is formed can be used as the transistor M1 to the transistor M7. In particular, the use of silicon with high crystallinity, such as single crystal silicon or polycrystalline silicon, is preferable because high field-effect mobility is achieved and higher-speed operation is possible.

Alternatively, a transistor using an oxide semiconductor may be used as one or more of the transistor M1 to the transistor M7, and transistors using silicon may be used as the other transistors.

Although n-channel transistors are shown as the transistors in FIG. 19A and FIG. 19B, p-channel transistors can alternatively be used.

The transistors included in the pixel circuit PIX1 and the transistors included in the pixel circuit PIX2 are preferably formed side by side over the same substrate. It is particularly preferable that the transistors included in the pixel circuit PIX1 and the transistors included in the pixel circuit PIX2 be periodically arranged in one region.

One or more layers including one or both of the transistor and the capacitor are preferably provided to overlap with the light-receiving element PD or the light-emitting element EL. Thus, the effective area of each pixel circuit can be reduced, and a high-resolution light-receiving portion or display portion can be achieved.

At least part of this embodiment can be implemented in combination with the other embodiments described in this specification as appropriate.

Embodiment 3

In this embodiment, electronic devices of one embodiment of the present invention will be described with reference to FIG. 20 to FIG. 22.

An electronic device in this embodiment includes the display device of one embodiment of the present invention. For example, the display device of one embodiment of the present invention can be used in a display portion of the electronic device. The display device of one embodiment of the present invention has a function of sensing light, and thus can perform biometric authentication on the display portion or sense a touch or a near touch on the display portion. Thus, the electronic device can have improved functionality and convenience, for example.

Examples of the electronic devices include a digital camera, a digital video camera, a digital photo frame, a mobile phone, a portable game console, a portable information terminal, and an audio reproducing device, in addition to electronic devices with a relatively large screen, such as a television device, a desktop or laptop personal computer, a monitor of a computer or the like, digital signage, and a large game machine such as a pachinko machine.

The electronic device in this embodiment may include a sensor (a sensor having a function of measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays).

The electronic device in this embodiment can have a variety of functions. For example, the electronic device can have a function of displaying a variety of data (a still image, a moving image, a text image, and the like) on the display portion, a touch panel function, a function of displaying a calendar, date, time, and the like, a function of executing a variety of software (programs), a wireless communication function, and a function of reading out a program or data stored in a recording medium.

Figure 20A:
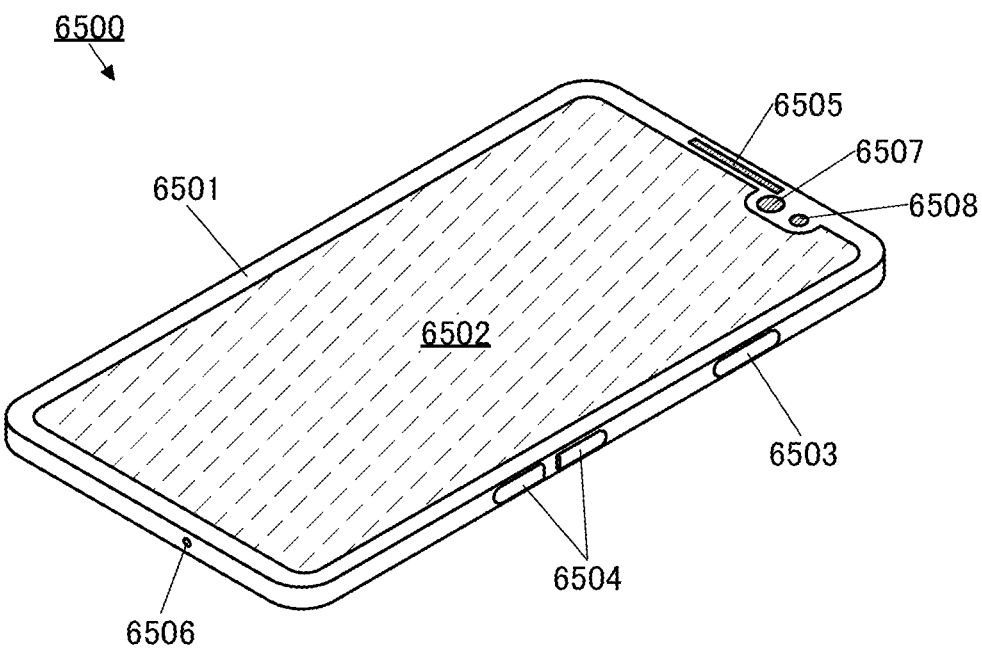
FIG. 20A and FIG. 20B are diagrams illustrating a structure example of an electronic device.

An electronic device 6500 illustrated in FIG. 20A is a portable information terminal that can be used as a smartphone.

The electronic device 6500 includes a housing 6501, a display portion 6502, a power button 6503, buttons 6504, a speaker 6505, a microphone 6506, a camera 6507, a light source 6508, and the like. The display portion 6502 has a touch panel function.

The display device of one embodiment of the present invention can be used in the display portion 6502.

Figure 20B:
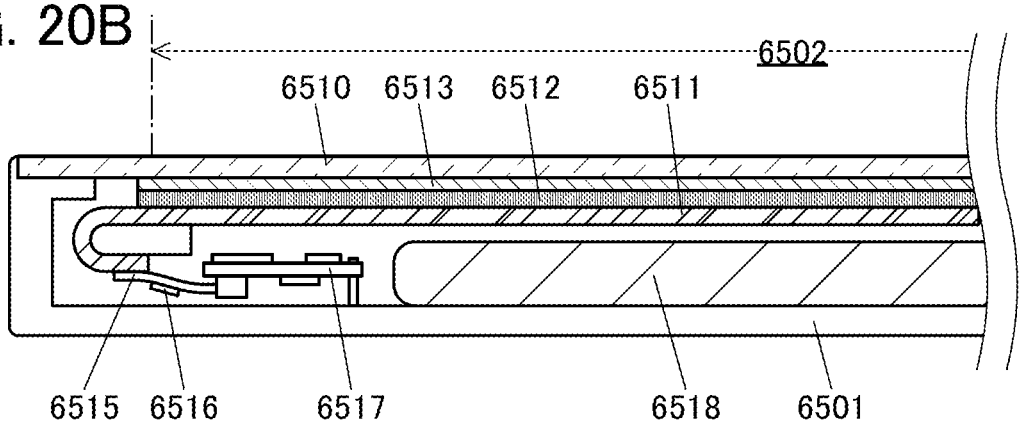

FIG. 20B is a schematic cross-sectional view including an end portion of the housing 6501 on the microphone 6506 side.

A protection member 6510 having a light-transmitting property is provided on the display surface side of the housing 6501, and a display panel 6511, an optical member 6512, a touch sensor panel 6513, a printed circuit board 6517, a battery 6518, and the like are provided in a space surrounded by the housing 6501 and the protection member 6510.

The display panel 6511, the optical member 6512, and the touch sensor panel 6513 are fixed to the protection member 6510 with an adhesive layer (not shown).

Part of the display panel 6511 is folded back in a region outside the display portion 6502, and an FPC 6515 is connected to the part that is folded back. An IC 6516 is mounted on the FPC 6515. The FPC 6515 is connected to a terminal provided on the printed circuit board 6517.

A flexible display of one embodiment of the present invention can be used as the display panel 6511. Thus, an extremely lightweight electronic device can be achieved. Since the display panel 6511 is extremely thin, the battery 6518 with high capacity can be mounted with the thickness of the electronic device controlled. An electronic device with a narrow frame can be achieved when part of the display panel 6511 is folded back so that the portion connected to the FPC 6515 is provided on the rear side of a pixel portion.

Figure 21A:
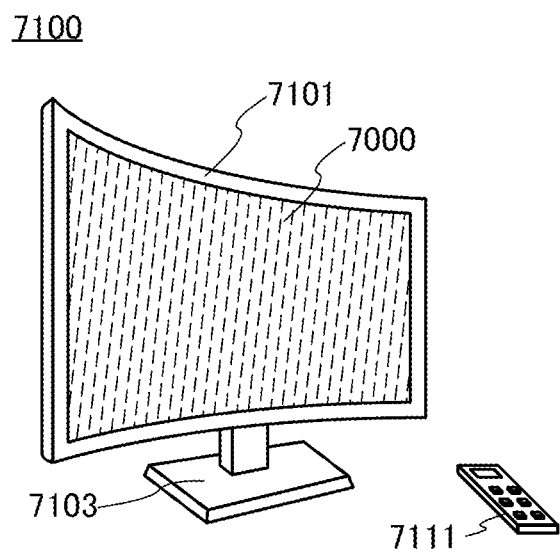
FIG. 21A to FIG. 21D are diagrams illustrating structure examples of electronic devices.

FIG. 21A illustrates an example of a television device. In a television device 7100, a display portion 7000 is incorporated in a housing 7101. Here, a structure in which the housing 7101 is supported by a stand 7103 is illustrated.

The display device of one embodiment of the present invention can be used in the display portion 7000.

Operation of the television device 7100 illustrated in FIG. 21A can be performed with an operation switch provided in the housing 7101 or a separate remote controller 7111. Alternatively, the display portion 7000 may include a touch sensor, and the television device 7100 may be operated by a touch on the display portion 7000 with a finger or the like. The remote controller 7111 may be provided with a display portion for displaying data output from the remote controller 7111. With operation keys or a touch panel provided in the remote controller 7111, channels and volume can be operated and videos displayed on the display portion 7000 can be operated.

Note that the television device 7100 has a structure in which a receiver, a modem, and the like are provided. A general television broadcast can be received with the receiver. When the television device is connected to a communication network with or without wires via the modem, one-way (from a transmitter to a receiver) or two-way (between a transmitter and a receiver or between receivers, for example) data communication can be performed.

Figure 21B:
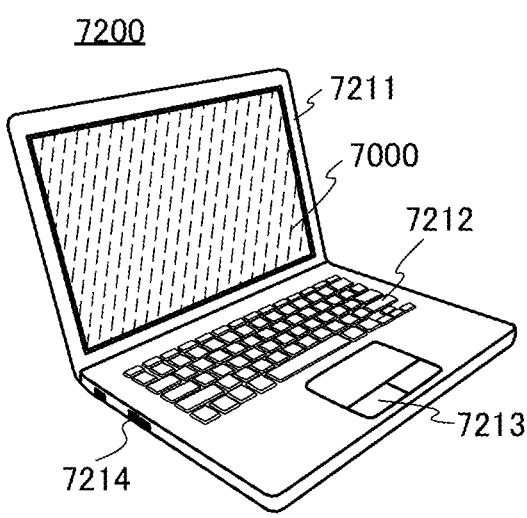

FIG. 21B illustrates an example of a laptop personal computer. A laptop personal computer 7200 includes a housing 7211, a keyboard 7212, a pointing device 7213, an external connection port 7214, and the like. In the housing 7211, the display portion 7000 is incorporated.

The display device of one embodiment of the present invention can be used in the display portion 7000.

Figure 21C:
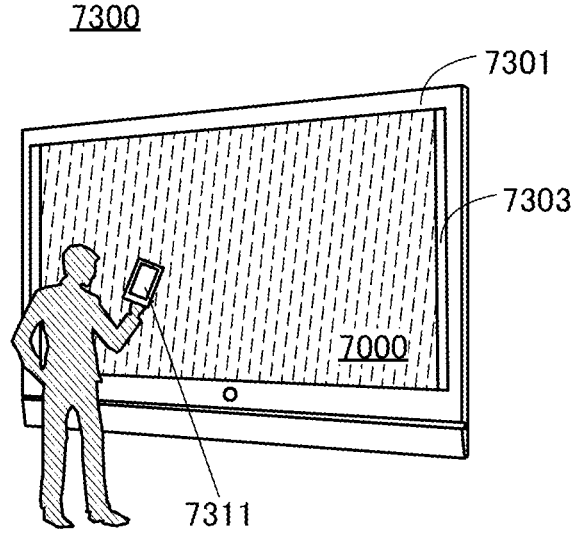
Figure 21D:
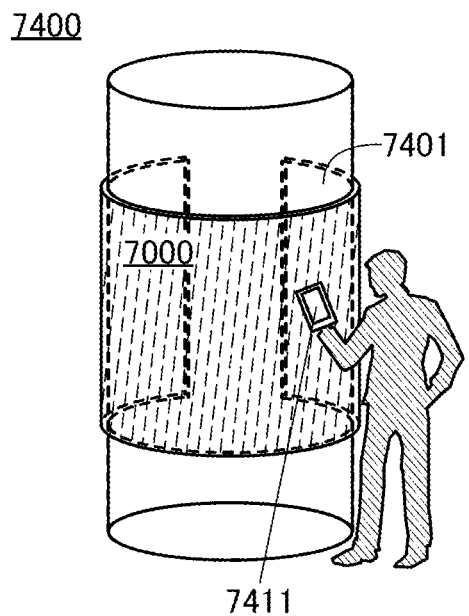

FIG. 21C and FIG. 21D illustrate examples of digital signage.

Digital signage 7300 illustrated in FIG. 21C includes a housing 7301, the display portion 7000, a speaker 7303, and the like. Furthermore, the digital signage can include an LED lamp, operation keys (including a power switch or an operation switch), a connection terminal, a variety of sensors, a microphone, and the like.

FIG. 21D is digital signage 7400 attached to a cylindrical pillar 7401. The digital signage 7400 includes the display portion 7000 provided along a curved surface of the pillar 7401.

The display device of one embodiment of the present invention can be used for the display portion 7000 in FIG. 21C and FIG. 21D.

A larger area of the display portion 7000 can increase the amount of data that can be provided at a time. The larger display portion 7000 attracts more attention, so that the advertising effectiveness can be enhanced, for example.

The use of a touch panel in the display portion 7000 is preferable because in addition to display of an image or a moving image on the display portion 7000, intuitive operation by a user is possible. Moreover, for an application for providing information such as route information or traffic information, usability can be enhanced by intuitive operation.

As illustrated in FIG. 21C and FIG. 21D, the digital signage 7300 or the digital signage 7400 is preferably capable of working with an information terminal 7311 or an information terminal 7411 such as a user's smartphone through wireless communication. For example, information of an advertisement displayed on the display portion 7000 can be displayed on a screen of the information terminal 7311 or the information terminal 7411. By operation of the information terminal 7311 or the information terminal 7411, display on the display portion 7000 can be switched.

It is possible to make the digital signage 7300 or the digital signage 7400 execute a game with use of the screen of the information terminal 7311 or the information terminal 7411 as an operation means (controller). Thus, an unspecified number of users can join in and enjoy the game concurrently.

Electronic devices illustrated in FIG. 22A to FIG. 22F include a housing 9000, a display portion 9001, a speaker 9003, an operation key 9005 (including a power switch or an operation switch), a connection terminal 9006, a sensor 9007 (a sensor having a function of measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays), a microphone 9008, and the like.

The electronic devices illustrated in FIG. 22A to FIG. 22F have a variety of functions. For example, the electronic devices can have a function of displaying a variety of information (a still image, a moving image, a text image, and the like) on the display portion, a touch panel function, a function of displaying a calendar, date, time, and the like, a function of controlling processing with use of a variety of software (programs), a wireless communication function, and a function of reading out and processing a program or data stored in a recording medium. Note that the functions of the electronic devices are not limited thereto, and the electronic devices can have a variety of functions. The electronic devices may include a plurality of display portions. The electronic devices may each include a camera or the like and have a function of taking a still image or a moving image and storing the taken image in a recording medium (an external recording medium or a recording medium incorporated in the camera), a function of displaying the taken image on the display portion, or the like.

The details of the electronic devices illustrated in FIG. 22A to FIG. 22F are described below.

Figure 22A:
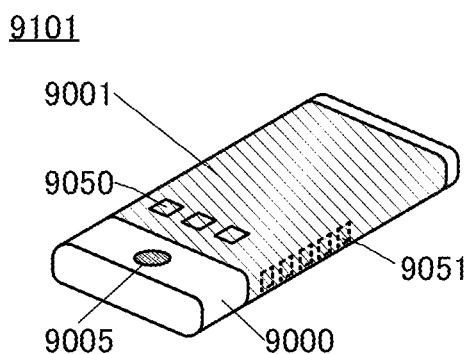
FIG. 22A to FIG. 22F are diagrams illustrating structure examples of electronic devices.

FIG. 22A is a perspective view illustrating a portable information terminal 9101. For example, the portable information terminal 9101 can be used as a smartphone. Note that the portable information terminal 9101 may be provided with the speaker 9003, the connection terminal 9006, the sensor 9007, or the like. The portable information terminal 9101 can display characters and image information on its plurality of surfaces. FIG. 22A shows an example in which three icons 9050 are displayed. Information 9051 indicated by dashed rectangles can be displayed on another surface of the display portion 9001. Examples of the information 9051 include notification of reception of an e-mail, SNS, or an incoming call, the title and sender of an e-mail, SNS, or the like, the date, the time, remaining battery, and the reception strength of an antenna. Alternatively, the icon 9050 or the like may be displayed in the position where the information 9051 is displayed.

Figure 22B:
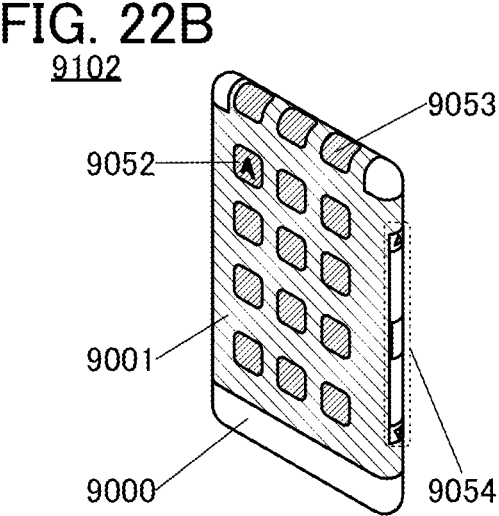

FIG. 22B is a perspective view illustrating a portable information terminal 9102. The portable information terminal 9102 has a function of displaying information on three or more surfaces of the display portion 9001. Here, an example in which information 9052, information 9053, and information 9054 are displayed on different surfaces is shown. For example, a user can check the information 9053 displayed in a position that can be observed from above the portable information terminal 9102, with the portable information terminal 9102 put in a breast pocket of his/her clothes. The user can see the display without taking out the portable information terminal 9102 from the pocket and decide whether to answer the call, for example.

Figure 22C:
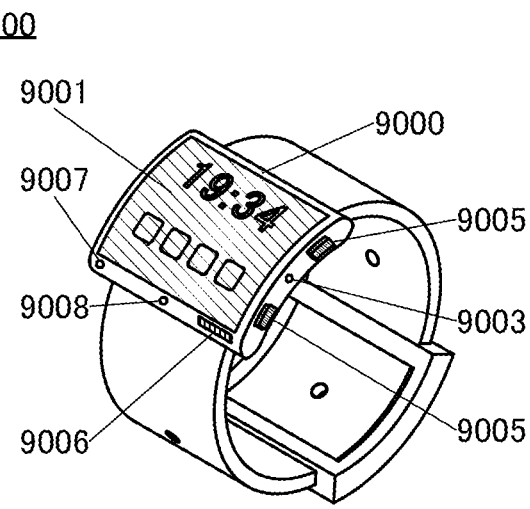

FIG. 22C is a perspective view illustrating a watch-type portable information terminal 9200. For example, the portable information terminal 9200 can be used as a smart watch. The display surface of the display portion 9001 is curved and provided, and display can be performed along the curved display surface. Mutual communication between the portable information terminal 9200 and, for example, a headset capable of wireless communication enables hands-free calling. With the connection terminal 9006, the portable information terminal 9200 can perform mutual data transmission with another information terminal and charging. Note that the charging operation may be performed by wireless power feeding.

Figure 22D:
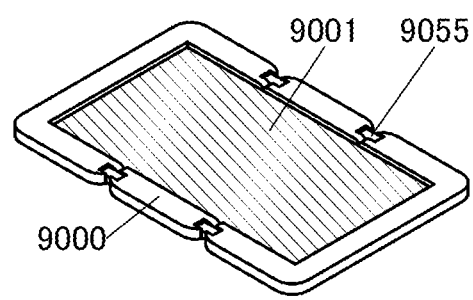
Figure 22E:
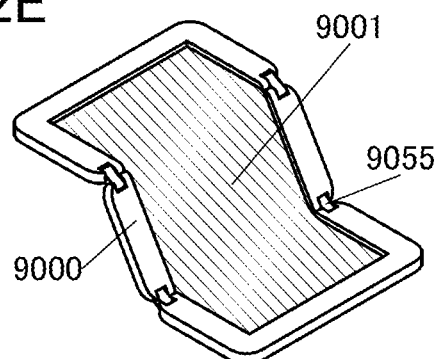
Figure 22F:
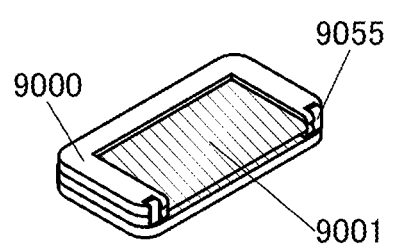

FIG. 22D, FIG. 22E, and FIG. 22F are perspective views illustrating a foldable portable information terminal 9201. FIG. 22D is a perspective view of an opened state of the portable information terminal 9201, FIG. 22F is a perspective view of a folded state thereof, and FIG. 22E is a perspective view of a state in the middle of change from one of FIG. 22D and FIG. 22F to the other. The portable information terminal 9201 is highly portable in the folded state and is highly browsable in the opened state because of a seamless large display region. The display portion 9001 of the portable information terminal 9201 is supported by three housings 9000 joined by hinges 9055. For example, the display portion 9001 can be bent with a radius of curvature greater than or equal to 0.1 mm and less than or equal to 150 mm.

At least part of this embodiment can be implemented in combination with the other embodiments described in this specification as appropriate.

REFERENCE NUMERALS

10A to 10F: display device, 21, 22, 23a, 23c: light, 23b, 23d: reflected light, 30, 31B, 31G, 31R, 31W, 32: pixel, 41, 42: transistor, 50, 50a to 50g: display device, 51, 51a, 51b, 52: substrate, 53: light-receiving element, 54: light-emitting element, 55, 55a, 55b: functional layer, 57, 57B, 57G, 57R: light-emitting element, 58: reflective layer, 59, 59a to 59c: light guide plate, 60: finger, 60a: hand, 61: contact portion, 62: fingerprint, 63: image-capturing range, 65: stylus, 66: path, 67: blood vessel, 71: resin layer, 72: conductive layer, 75: bezel, 76: button, 77: sensor, 80, 80a to 80d: electronic device, 81: display portion, 82, 82a to 82e: housing, 83: electrode, 84: camera, 85a to 85c: region, 86: microphone, 87: band, 88a, 88b: data, 88c: character image, 89a to 89c: joint portion, 90: system, 91: arithmetic portion, 92: memory portion, 92a to 92c: learning model, 92d: local data, 93: input portion, 93a: photosensor, 93b: camera, 93c: microphone, 93d: electrocardiogram monitor, 94: output portion, 94a: display, 94b: speaker, 94c: vibration device, 95: bus line This application is based on Japanese Patent Application Serial No. 2019-076318 filed on Apr. 12, 2019, the entire contents of which are hereby incorporated herein by reference.

The invention claimed is:

1. A display device comprising:
a substrate;
a first pixel electrode over the substrate;
a second pixel electrode over the substrate;
a light-emitting layer over the first pixel electrode;
an active layer over the second pixel electrode;
a common layer over the light-emitting layer and the active layer;
a common electrode over the common layer;
a lens; and
a light guide plate,
wherein the first pixel electrode, the light-emitting layer, the common layer, and the common electrode overlap with each other in a light-emitting element,
wherein the second pixel electrode, the active layer, the common layer, and the common electrode overlap with each other in a light-receiving element,
wherein the lens and the light-receiving element overlap with each other,
wherein the light guide plate and the light-emitting element overlap with each other,
wherein the light guide plate and the light-receiving element overlap with each other,
wherein the light-emitting element emits first light to an outside through the light guide plate,
wherein second light is configured to diffuse inside the light guide plate,
wherein the light-receiving element is configured to receive the first light through the lens,
wherein the light-receiving element is configured to receive the second light,
wherein the first light comprises visible light, and
wherein the second light comprises infrared light.

2. The display device according to claim 1,
wherein the light-emitting layer comprises an organic compound, and
wherein the active layer comprises silicon.

3. The display device according to claim 1, wherein the lens comprises a resin.

4. The display device according to claim 1, wherein the lens comprises an oxide containing indium and tin.

5. The display device according to claim 1, further comprising a second common layer under the light-emitting layer and the active layer.

6. A display device comprising:
- a substrate;
- a first pixel electrode over the substrate;
- a second pixel electrode over the substrate;
- a light-emitting layer over the first pixel electrode;
- an active layer over the second pixel electrode;
- a common layer over the light-emitting layer and the active layer;
- a common electrode over the common layer;
- a light-blocking layer;
- a lens; and
- a light guide plate,
- wherein the first pixel electrode, the light-emitting layer, the common layer, and the common electrode overlap with each other in a light-emitting element,
- wherein the second pixel electrode, the active layer, the common layer, and the common electrode overlap with each other in a light-receiving element,
- wherein the lens and the light-receiving element overlap with each other,
- wherein an end portion of the lens is covered with the light-blocking layer,
- wherein the light guide plate and the light-emitting element overlap with each other,
- wherein the light guide plate and the light-receiving element overlap with each other,
- wherein the light-emitting element emits first light to an outside through the light guide plate,
- wherein second light is configured to diffuse inside the light guide plate,
- wherein the light-receiving element is configured to receive the first light through the lens, and
- wherein the light-receiving element is configured to receive the second light.

7. The display device according to claim 6,
- wherein the light-emitting layer comprises an organic compound, and
- wherein the active layer comprises silicon.

8. The display device according to claim 6, wherein the lens comprises a resin.

9. The display device according to claim 6, wherein the lens comprises an oxide containing indium and tin.

10. The display device according to claim 6,
- wherein the first light comprises visible light, and
- wherein the second light comprises infrared light.

11. The display device according to claim 6, further comprising a second common layer under the light-emitting layer and the active layer.

12. A display device comprising:
- a substrate;
- a first pixel electrode over the substrate;
- a second pixel electrode over the substrate;
- a light-emitting layer over the first pixel electrode;
- an active layer over the second pixel electrode;
- a common layer over the light-emitting layer and the active layer;
- a common electrode over the common layer; and
- a lens,
- wherein the first pixel electrode, the light-emitting layer, the common layer, and the common electrode overlap with each other in a light-emitting element,
- wherein the second pixel electrode, the active layer, the common layer, and the common electrode overlap with each other in a light-receiving element,
- wherein the lens and the light-receiving element overlap with each other,
- wherein the light-emitting element emits first light to an outside, and
- wherein the light-receiving element is configured to receive the first light through the lens.

13. The display device according to claim 12,
- wherein the light-emitting layer comprises an organic compound, and
- wherein the active layer comprises silicon.

14. The display device according to claim 12, wherein the lens comprises a resin.

15. The display device according to claim 12, wherein the lens comprises an oxide containing indium and tin.

16. The display device according to claim 12, further comprising a light-blocking layer,
- wherein an end portion of the lens is covered with the light-blocking layer.

17. The display device according to claim 12, further comprising a second common layer under the light-emitting layer and the active layer.

* * * * *